US008277497B2

(12) United States Patent
Noel

(10) Patent No.: US 8,277,497 B2
(45) Date of Patent: *Oct. 2, 2012

(54) METHOD AND THERMALLY ACTIVE MULTI-PHASE HEAT TRANSFER APPARATUS AND METHOD FOR ABSTRACTING HEAT FROM INDIVIDUAL'S WRIST

(76) Inventor: Thomas P. Noel, West Warwick, RI (US)

( * ) Notice: Subject to any disclaimer, the term of this patent is extended or adjusted under 35 U.S.C. 154(b) by 836 days.

This patent is subject to a terminal disclaimer.

(21) Appl. No.: 12/284,859

(22) Filed: Sep. 25, 2008

(65) Prior Publication Data

US 2009/0076574 A1    Mar. 19, 2009

Related U.S. Application Data

(63) Continuation-in-part of application No. 12/215,225, filed on Jun. 26, 2008, which is a continuation-in-part of application No. 11/809,205, filed on May 31, 2007, now abandoned, which is a continuation of application No. 11/209,354, filed on Aug. 23, 2005, now Pat. No. 7,240,720, which is a continuation-in-part of application No. 10/751,061, filed on Jan. 2, 2004, now abandoned, which is a continuation-in-part of application No. 10/463,055, filed on Jun. 17, 2003, now Pat. No. 7,055,575, which is a continuation-in-part of application No. 10/274,161, filed on Oct. 18, 2002, now Pat. No. 6,904,956.

(60) Provisional application No. 60/997,096, filed on Sep. 28, 2007, provisional application No. 61/188,594, filed on Aug. 11, 2008.

(51) Int. Cl.
*A61F 7/00* (2006.01)

(52) U.S. Cl. ....................................................... 607/111

(58) Field of Classification Search .................... 607/96, 607/108, 111, 114; 165/46
See application file for complete search history.

(56) References Cited

U.S. PATENT DOCUMENTS

| | | | | |
|---|---|---|---|---|
| 5,476,491 A | * | 12/1995 | Mayn | 607/111 |
| 6,083,256 A | * | 7/2000 | Der Ovanesian | 607/114 |
| 6,755,852 B2 | * | 6/2004 | Lachenbruch et al. | 607/114 |

* cited by examiner

*Primary Examiner* — Nicholas Lucchesi
*Assistant Examiner* — Nathan R Price
(74) *Attorney, Agent, or Firm* — Tod R. Nissle, P.C.

(57) ABSTRACT

Cold pack apparatus for abstracting heat comprises a container charged with a first liquid and with small auxiliary containers free to circulate in the first liquid. Each of the small auxiliary containers is charged with a second liquid. The first and second liquids each have a selected temperature of transformation that facilitates use of the apparatus to heat or cool a substance contacted by the apparatus. The cold pack apparatus reduces pain at a joint or at a diseased area in the epithelium by producing spaced apart points of cold at the joint or diseased area for an extended period of time of one hours or more.

3 Claims, 26 Drawing Sheets

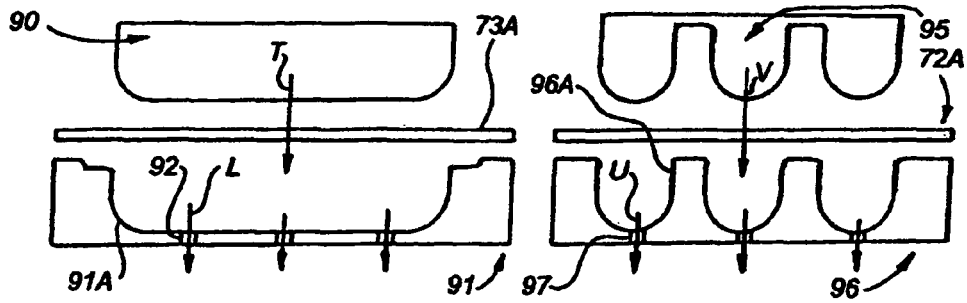
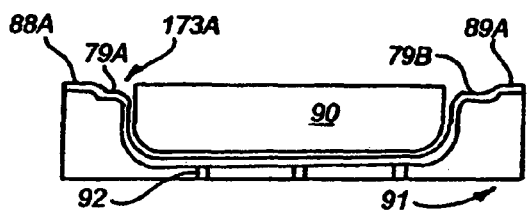
FIG. 10A
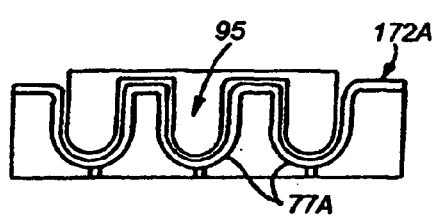
FIG. 11A
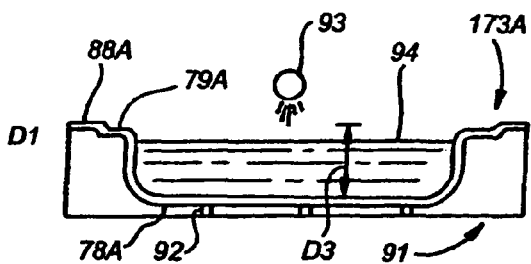
FIG. 10B
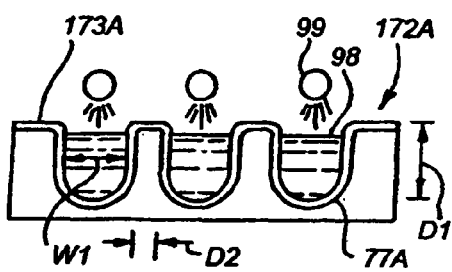
FIG. 11B
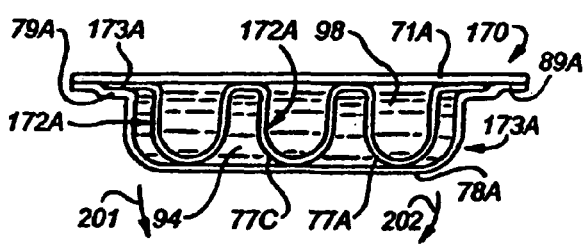
FIG. 10C
FIG. 11C
FIG. 10D

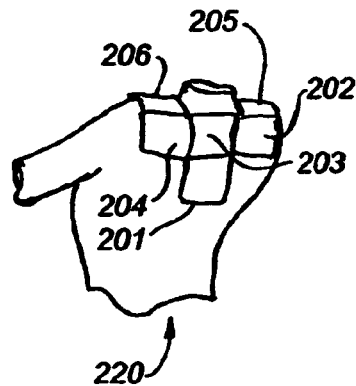
FIG. 15
FIG. 16
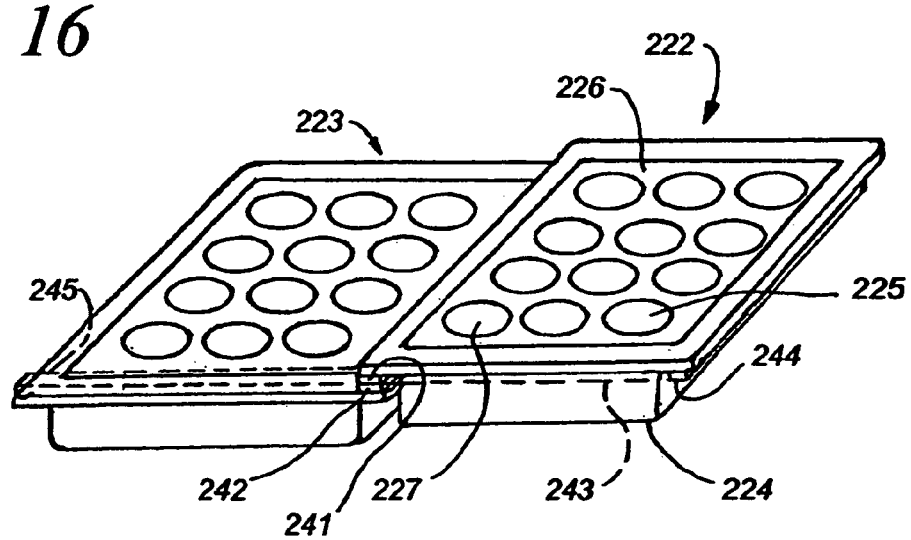
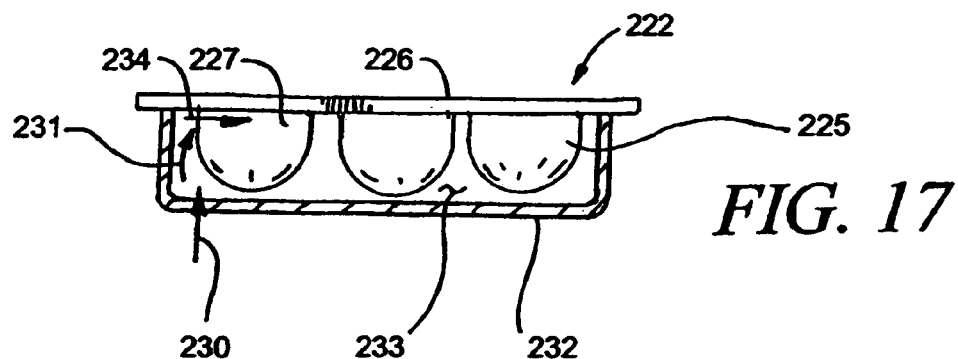
FIG. 17

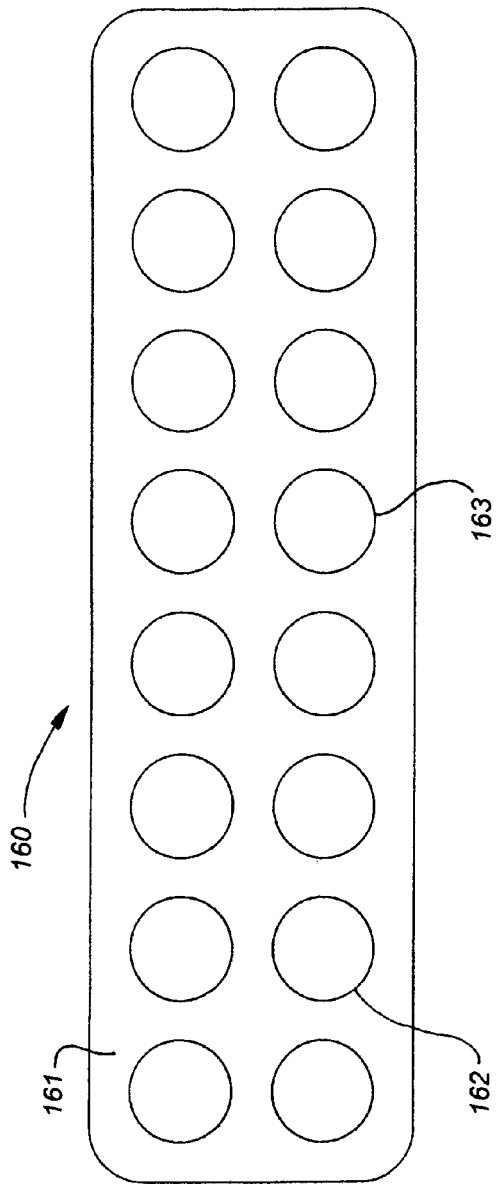
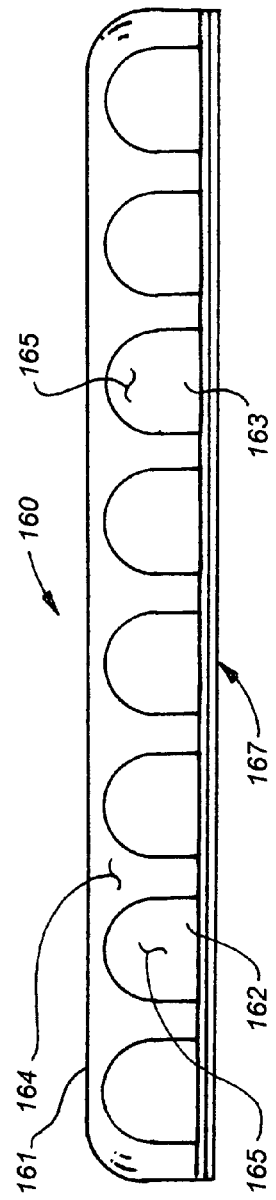
FIG. 29
FIG. 30

METHOD AND THERMALLY ACTIVE MULTI-PHASE HEAT TRANSFER APPARATUS AND METHOD FOR ABSTRACTING HEAT FROM INDIVIDUAL'S WRIST

This application claims priority based on provisional applications 60/997,096 filed Sep. 28, 2007, and, 61/188,594 filed Aug. 11, 2008, and is a continuation-in-part of application Ser. No. 12/215,225 filed Jun. 26, 2008, which is a continuation-in-part of application Ser. No. 11/809,205, filed May 31, 2007, which is a continuation of application Ser. No. 11/209,354 filed Aug. 23, 2005; which is a continuation-in-part of application Ser. No. 10/751,061, filed Jan. 2, 2004, which is a continuation-in-part of application Ser. No. 10,463,055, filed Jun. 17, 2003, which is a continuation-in-part of application Ser. No. 10/274,161, filed Oct. 18, 2002.

This invention pertains to apparatus and methods for abstracting heat from a substance.

More particularly, the invention pertains to an improved apparatus and method which utilizes a matrix comprised of liquids and solids to abstract, over an extended period of time, heat from a substance.

In a further respect, the invention pertains to an improved apparatus of the type described which utilizes a plurality of heat transfer elements having three dimensional parity.

In another respect, the invention pertains to an improved heat abstracting apparatus of the type described which convects heat along paths intermediate spaced apart heat transfer elements.

In still a further respect, the invention pertains to an improved apparatus and method of the type described in which heat transfer elements are shaped to absorb heat along vertical and lateral paths.

In still another respect, the invention pertains to an improved simplified method of manufacturing a heat transfer device.

In yet a further respect, the invention pertains to an improved heat abstracting apparatus of the type described which provides efficient transfer using a single heat transfer element-liquid interface.

So called "cold packs" are well known and typically, for example, comprise pliable, hollow, vinyl containers filled with a gelatin. In use, the cold pack is frozen and is placed against an individual's neck or other part of the individual's body to cool the individual. One such conventional cold pack is marketed under the trademark "THERAPAC" and comprises a twelve inch-by-twelve inch two ply vinyl container filled with a white odorless insoluble gelatin. Another conventional cold pack is marketed under the trademark "COLPAC" and comprises a twelve inch-by-twelve inch single ply polymer container filled with a gray odorless soluble gelatin. Such conventional cold packs are widely disseminated and effectively absorb heat. One principal disadvantage of such cold packs is that they have a relatively short-lived ability to stay cold. For example, when the THERAPAC and COLPAC cold packs noted above are removed from a freezer, the temperature on the outer surface of the cold pack can be five degrees F. After about an hour, the temperature can be about forty-five to fifty degrees F. After about two hours, the temperature on the outer surface of the cold packs can be about fifty-two to fifty-eight degrees F. After about three hours, the temperature can be about sixty-five to seventy degrees F. Consequently, after only an hour the temperature of the outer surface of each of the cold packs is well above freezing.

Accordingly, it would be highly desirable to provide an improved cold pack which would, after being exposed to ambient temperature, maintain a low temperature for an extended period of time.

Therefore, it is a principal object of the invention to provide an improved apparatus for abstracting heat from a solid, liquid, gas or other substance.

A further object of the instant invention is to provide an improved cold pack which will maintain a cold temperature for an extended period of time after being exposed to a temperature greater than that of the cold pack.

Another object of the invention is to provide an improved method for manufacturing a cold pack.

Still a further object of the invention is to provide a heat transfer device that facilitates conforming the device to the contour of the body.

Still another object of the invention is to provide an improved heat transfer device with a module matrix that facilitates folding the device and partitioning the device.

Yet another object of the invention is to provide an improved heat transfer device with a module matrix that facilitates pressure equalization and convection and the uniform transfer of heat.

These and other, further and more specific objects and advantages of the invention will be apparent to those skilled in the art from the following detailed description thereof, taken in conjunction with the drawings, in which:

FIG. 10A is a front section view illustrating the first step in a method for making a pan member used in the invention;

FIG. 10B is a front section view illustrating the second step in a method for making a pan member used in the invention;

FIG. 10C is a front section view illustrating the administration of fluid to the pan member of FIG. 10B;

FIG. 10D is a front section view illustrating the incorporation and sealing of a module matrix into the pan member-fluid system of FIG. 10C;

FIG. 11A is a front section view illustrating the first step in producing a module matrix used in the invention;

FIG. 11B is a front section view illustrating the second step in producing a module matrix used in the invention;

FIG. 11C is a front section view illustrating charging a module matrix with fluid;

FIG. 15 is a perspective view illustrating the mode of operation of the heat transfer device of the invention;

FIG. 16 is a perspective view illustrating a further embodiment of the heat transfer device of the invention;

FIG. 17 is a side partial section view of a heat transfer device of the invention illustrating the multi-phase heat transfer mechanism of the invention;

FIG. 29 is a top view of the modular cooling device utilized in apparatus for cooling an individual's wrists while the individual is typing on a computer key board;

FIG. 30 is a side view illustrating the modular cooling device of FIG. 29;

Figure 1:
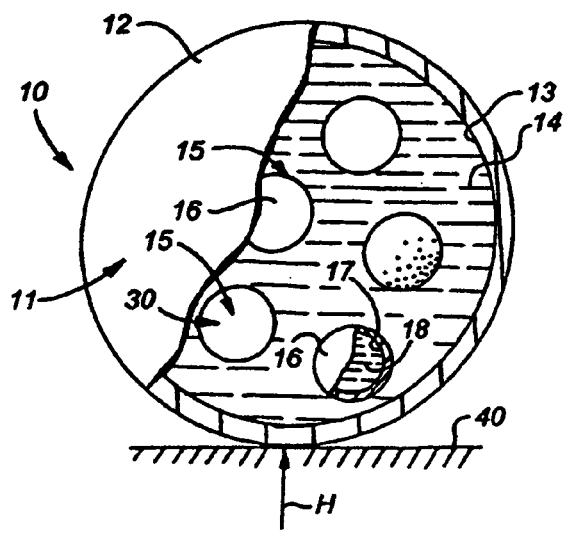
FIG. 1 is an elevation view illustrating a heat transfer device constructed in accordance with the principles of the invention.

Briefly, in accordance with the invention, I provide an improved heat transfer device for use in contacting and drawing heat away from a substance. The heat transfer device includes a hollow primary container including a wall, and a first liquid housed in the container; and, includes at least one hollow auxiliary container in the first liquid and including a wall, and a second liquid housed in the auxiliary container. The second liquid has a freezing point less than the freezing point of the first liquid.

In another embodiment of the invention, I provide an improved method for cooling a substance. The method includes the steps of providing a heat transfer device. The heat transfer device includes a hollow primary container including a wall, and a first liquid housed in the container. The primary container also includes at least one hollow auxiliary container in the first liquid. The auxiliary container includes a wall, and a second liquid housed in the auxiliary container. The second liquid has a freezing point less than the freezing point of the first liquid. The method also includes the steps of cooling the heat transfer device to freeze the second liquid; and, contacting the substance with the heat transfer device.

In a further embodiment of the invention, I provide an improved method for cooling a substance. The method includes the step of providing a heat transfer device. The heat transfer device includes a hollow primary container. The primary container includes a wall, and a first liquid housed in the container. The primary container also includes at least one hollow auxiliary container in the first liquid. The hollow auxiliary container includes a wall, and a second liquid housed in the wall of the auxiliary container. The second liquid has a freezing point less than the freezing point of the first liquid. The method also includes the steps of cooling the heat transfer device to freeze the second liquid; and, contacting the substance with the heat transfer device such that heat is abstracted from the substance into the first liquid by conduction through the wall of the primary container, such that heat abstracted into the first liquid by conduction through the wall of the primary container causes the liquid to have a nonuniform temperature and produces circulatory motion in the liquid due to variation in the density of the liquid and the action of gravity, and such that heat is abstracted from the first liquid by the conduction through the wall of the auxiliary container.

In still another embodiment of the invention, I provide an improved two phase single wall heat transfer device for use in contacting and drawing heat away from a substance. The heat transfer device includes an outer wall circumscribing and enclosing an inner space; a plurality of hollow fluid tight containers connected to a portion of said wall and extending from the wall into the inner space; a first heat-exchange composition in the inner space contacting each of the fluid tight containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation.

In still a further embodiment of the invention, I provide an improved two phase single wall bi-directional heat transfer device for use in contacting and drawing heat away from a substance. The heat transfer device includes an outer wall circumscribing and enclosing an inner space; a plurality of hollow fluid containers mounted on the outer wall in the inner space, each of the containers including a top and at least one side; a first heat-exchange composition in the inner space contacting each of the fluid containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation. The side of each of the hollow fluid tight containers is substantially normal to the top such that heat traveling through the hollow fluid container between the first and second heat-exchange compositions travels in a first direction through the top and in a second direction through the side. The first direction is substantially normal to the second direction.

In yet another embodiment of the invention, I provide an improved two phase single wall heat transfer device for use in contacting and drawing heat away from a substance. The heat transfer device includes an outer wall circumscribing and enclosing an inner space; a plurality of spaced apart hollow fluid containers mounted in said inner space above said outer wall, each of said containers including a top and at least one side; a floor interconnecting the hollow fluid tight containers; a first heat-exchange composition in the inner space contacting each of the fluid containers and comprising a liquid which undergoes a change of state from the liquid phase to the solid phase at a selected temperature of transformation; a second heat-exchange composition in each of said hollow containers comprising a liquid which undergoes a change of state from the liquid phase to the solid phase at a selected temperature of transformation; the wall, floor, and fluid containers being shaped and dimensioned such that heat absorbed through the wall by the first heat-exchange composition is carried by convection intermediate the hollow fluid containers and into contact with the sides of the containers and with the floor.

In yet a further embodiment of the invention, I provide an improved two phase single wall heat transfer device for use in contacting and drawing heat away from a substance. The heat transfer device includes an outer wall circumscribing and enclosing an inner space; a plurality of hollow fluid containers mounted in the inner space; a first heat-exchange composition in the inner space contacting each of the fluid containers and comprising a liquid which undergoes a change of state from the liquid phase to the solid phase at a selected temperature of transformation; a second heat-exchange composition in each of hollow containers comprising a liquid which undergoes a change of state from the liquid phase to the solid phase at a selected temperature of transformation; and, a pump for circulating the first heat-exchange composition into contact with the fluid containers.

In still yet another embodiment of the invention I provide an improved pliable two phase single wall heat transfer device for use in contacting and drawing heat away from a substance. The heat transfer device comprises an outer wall circumscribing and enclosing an inner space; a plurality of spaced apart hollow fluid tight containers connected to a portion of the wall, extending from the wall into the inner space, and including rounded bottoms to facilitate folding adjacent ones of the fluid containers against one another; a first heat-exchange composition in the inner space contacting each of the fluid tight containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation.

In yet still a further embodiment of the invention, I provide an improved method for manufacturing a two phase single wall bi-directional heat transfer device for use in contacting and drawing heat away from a substance. The improved method includes the steps of providing a first sheet of pliable material; forming a pan with the sheet of material, the pan including a peripheral lip extending around the pan; charging the pan with a first heat-exchange composition comprising a liquid which undergoes a change of state from the liquid phase to the solid phase at a selected temperature of transformation; providing a second sheet of pliable material; forming a module matrix with the second sheet of material, the module matrix including a peripheral edge and including a plurality of modules each with a bottom and an open top; placing the module matrix in the pan such that the bottom of each module extends into the first heat-exchange composition; administering a second heat-exchange composition to each of the modules comprising a liquid which undergoes a change of state from the liquid phase to the solid phase at a selected temperature of transformation liquid; and, sealing the first composition in the pan and the second composition in the module matrix.

In another embodiment of the invention I provide an improved pliable two phase single wall heat transfer device for use in contacting and drawing heat away from a substance. The heat transfer device comprises an outer wall circumscribing and enclosing an inner space; a plurality of spaced apart hollow fluid tight containers connected to a portion of the wall, extending from the wall into the inner space, and including rounded bottoms to facilitate folding adjacent ones of the fluid containers against one another; a first heat-exchange composition in the inner space contacting each of the fluid tight containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation. A plurality of channels interconnects pairs of the hollow containers to promote the flow of liquid therebetween.

In a further embodiment of the invention, I provide an improved pliable two phase single wall heat transfer device for use in contacting and drawing heat away from a substance. The heat transfer device comprises a plurality of matrix units each including an outer wall circumscribing and enclosing an inner space; a plurality of spaced apart hollow fluid tight containers connected to a portion of the wall, extending from the wall into the inner space; a first heat-exchange composition in the inner space contacting each of the fluid tight containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation. The heat transfer device also includes a fastening system for interconnecting the matrix units along at least a pair of separate spaced apart lines of weakening to enable the heat transfer device to be mounted over the shoulders and around the neck of an individual.

In still another embodiment of the invention, I provide an improved pliable two phase single wall heat transfer device for use in contacting and drawing heat away from a substance. The heat transfer device comprises plurality of matrix units each including an outer wall circumscribing and enclosing an inner space; a plurality of spaced apart hollow fluid tight containers connected to a portion of the wall, extending from the wall into the inner space; a first heat-exchange composition in the inner space contacting each of the fluid tight containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation. The heat transfer device also includes a fastening system for detachably interconnecting the matrix units in a plurality of different configurations along at least a pair of separate spaced apart lines of weakening to enable the heat transfer device to conform to different portions of an individual's body.

In still a further embodiment of the invention, I provide a method for drawing heat away from a substance. The method comprises the steps of conducting heat from the substance through a first sheet into a first fluid reservoir; moving heat by liquid convection in the reservoir; conducting through a second sheet into a second fluid reservoir heat transported by liquid convection in the first fluid reservoir; and, moving heat by liquid convection from the second fluid reservoir to the first fluid reservoir.

In yet still another embodiment of the invention, I provide an improved method of treating tissue to reduce inflammation and promote healing. The method comprises the steps of providing cooling apparatus that maintains a temperature in the range of thirty-three degrees F. to forty degrees F. for at least four hours when contacting the epithelium; and, contacting the epithelium adjacent the tissue with the cooling apparatus to provide a temperature in the range of thirty-three degrees F. to forty degrees F. continuously for a period of time of at least four hours.

In yet still a further embodiment of the invention, I provide an improved method of treating tissue to reduce inflammation and promote healing. The method comprises the steps of providing cooling apparatus with spaced apart modules that each have a bottom and maintain a temperature in the range of thirty-three to forty degrees F. for at least four hours when contacting the epithelium, the modules being spaced apart a distance in the range of eight mm to twelve mm and having a width and height each in the range of eighteen mm to thirty-two millimeters; and, of contacting the epithelium adjacent the tissue with the bottoms of the spaced apart modules for a continuous period of time of at least four hours.

In another embodiment of the invention, I provide an improved method of treating carpal tunnel syndrome in the wrists of an individual. The method comprises the steps of providing a computer keyboard; providing an elongate cooling wrist support comprising a heat conductive metal including a hollow inner space; and, providing a cooling apparatus that maintains a temperature in the range of thirty-three degrees F. to forty degrees F. for at least thirty minutes, the cooling apparatus shaped and dimensioned to slide into at least a portion of the hollow inner space. The cooling apparatus comprises a pan housing with a rounded top and a substantially flat bottom; a plurality of spaced apart modules inside said pan housing, each with a rounded top and a substantially flat bottom, and detached from the pan housing; a first fluid in the modules having a first freezing temperature; and, a second fluid in the pan housing intermediate the housing and the modules, the second fluid having a second freezing temperature different from the first freezing temperature. The method also includes the steps of cooling the elongate cooling unit to freeze at least one of the first and second fluids; placing the cooled cooling unit in the hollow inner space of the wrist support to contact and cool the wrist support; placing the wrist support generally adjacent the key board such that an individual can place his wrists on the wrist support and operate with his hands the keyboard; and, positioning the wrists of the individual on the wrist support such that the individual can operate the keyboard with the individual's hands.

In a further embodiment of the invention, I provide an improved method of treating carpal tunnel syndrome in the wrist of an individual. The method comprises the steps of providing a mouse stand with a mouse pad and a stand; providing an elongate cooling wrist support comprising a heat conductive metal including a hollow inner space; providing a cooling apparatus that maintains a temperature in the range of thirty-three degrees F. to forty degrees F. for at least thirty minutes. The cooling apparatus is shaped and dimensioned to slide into at least a portion of the hollow inner space and comprises a pan housing with a rounded top and a substantially flat bottom; a plurality of spaced apart modules inside said pan housing, each with a rounded top and a substantially flat bottom, and detached from the pan housing; a first fluid in the modules having a first freezing temperature; and, a second fluid in the pan housing intermediate the housing and the modules, the second fluid having a second freezing temperature different from the first freezing temperature. The method also includes the steps of cooling the elongate cooling unit to freeze at least one of the first and second fluids; placing the cooled cooling unit in the hollow inner space of the wrist support to contact and cool the wrist support; placing the wrist support on the step of the stand such that an individual can place a wrist on the wrist support and operate with his hand a mouse on the mouse pad; and, positioning the wrist of the individual on the wrist support such that the individual can operate the mouse with the individual's hand.

In still another embodiment of the invention, I provide an improved method of stabilizing the wrist and hand of an individual. The hand has an upper knuckle side and a lower palm side. The wrist has a top adjacent the upper side of the hand; a bottom side adjacent the palm side of the hand; and, sides extending between the top side and bottom side. The method comprises the steps of providing an elongate cooling wrist support. The wrist support comprises a first elongate splint panel having a first edge and a second edge; a second elongate splint panel generally parallel to the first elongate splint panel and having a third edge and a fourth edge; a first section of elastic material interconnecting the first edge of the first splint panel and the third edge of the second splint panel and sized to stretch when the wrist support is mounted on the individual's wrist and hand; a second section of elastic material interconnecting the second edge of the first splint panel and the third edge of the second splint panel and sized to stretch when said wrist support is mounted on the individual's wrist and hand; an opening; a cold pack housing extending over the opening; and, a cold pack shaped and dimensioned to be inserted in the cold pack housing. The method includes the further steps of cooling the cold pack in a refrigerator or freezer; placing the cold pack in the cold back housing; and, sliding the individual's wrist and hand into the wrist support such that the first elongate splint panel extends over the top of the wrist; the second elongate splint panel extends over the bottom of the wrist; the first and second sections of elastic material elastically stretch; and, the cold pack is adjacent the individual's wrist.

In still a further embodiment of the invention, I provide an improved method of cooling the head of an individual. The method comprises the steps of providing a plurality of cold packs each having a longitudinal axis; and, providing a flow wrap machine. The flow wrap machine has a roll of a strip of heat-sealable fabric; a first processing station to wrap the strip of fabric around one of the cold packs and heat seal the strip of fabric along a line generally parallel to the longitudinal axis; a second processing station to heat seal the strip of fabric at spaced apart intervals therealong; apparatus to feed the cold packs sequentially into the first processing station; and, apparatus to move the strip of fabric from the roll through the first and second processing stations to form a strip of separate interconnected sealed packets, and insert the cold packs in selected ones of the sealed packets to produce a headband with the selected ones of the sealed packets containing said cold packs and with others of said sealed packets empty and functioning as ties. The method also includes the steps of producing a headband with the flow wrap machine; placing the headband in a freezer to cool the cold packs; removing the headband from the freezer; and, mounting the headband on the individual's head with said ties.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates a heat transfer device generally identified by reference character 10. Device 10 includes a spherical hollow primary container having a wall 11 including spherical outer surface 12 and spherical inner surface 13. A liquid 14 is housed inside the primary container. At least one auxiliary spherical hollow container 15 is in and free to move and circulate about the reservoir formed by liquid 14. Each hollow container 15 includes a spherical wall 30 having a spherical outer surface 16 and a spherical inner surface 17. A liquid 18 is housed inside each auxiliary container 15. Liquid 14 has a lower (cooler) freezing point than liquid 18, and preferably, but not necessarily, has a freezing point lower than the coldest temperatures found in conventional household or commercial freezers. By way of example, and not limitation, liquid 14 presently comprises propylene glycol and liquid 18 comprises water. Liquid 18 preferably has a freezing point greater or equal to the coldest temperature found in conventional household or commercial freezers.

Other examples of compositions that can be utilized as liquid 14 or liquid 18 include aqueous solutions of ethyl alcohol, methyl alcohol, PRESTONE, iso-propyl alcohol, and glycerol. Magnesium chloride, sodium chloride, and calcium chloride brines can be utilized. Refrigerants which can be utilized as liquid 14 include ammonia, ethyl chloride, and methyl chloride.

The wall 11 is preferably, although not necessarily, fabricated from a pliable vinyl or other pliable material so that wall 11 will conform to a part of an individual's body or will conform to some other object that is contacted by heat transfer device 10. Similarly, the wall 30 is preferably, although not necessarily, fabricated from a pliable vinyl or other pliable material so that wall 30 will conform to a part of an individual's body or will conform to some other object. As would be appreciated by those of skill in the art, device 10 and walls 11 and 15 need not be spherical and can be made to have any desired shape, contour, and dimension. Walls 11 and 15 need not be pliable and can be substantially rigid.

In use of the heat transfer device 10, device 10 is placed in a freezer. Liquid 18, being water, freezes. Liquid 14, being propylene glycol, does not freeze. After liquid 18 freezes, device 10 is removed from the freezer and placed against a portion 40 of an individual's body or against some other object or substance so that device 10 absorbs heat H. Heat is absorbed through wall 11 and into liquid 14 by the transfer of kinetic energy from particle to particle. When heat is absorbed by liquid 14, liquid 14 has a non-uniform temperature, i.e., liquid near wall 11 is warmer and has a greater enthalpy than liquid farther away from wall 11. If liquid near wall 11 has a different temperature, the density of the liquid near wall 11 is different than the density of cooler liquid farther away from wall 11. This density differential, along with the force of gravity, causes circulation and movement of liquid 14. When, during this circulation and movement, warmed liquid 14 passes by and contacts an auxiliary spherical hollow container 15, heat is absorbed through wall 30 and into frozen liquid 18 by the transfer of kinetic energy from particle to particle.

Figure 2:
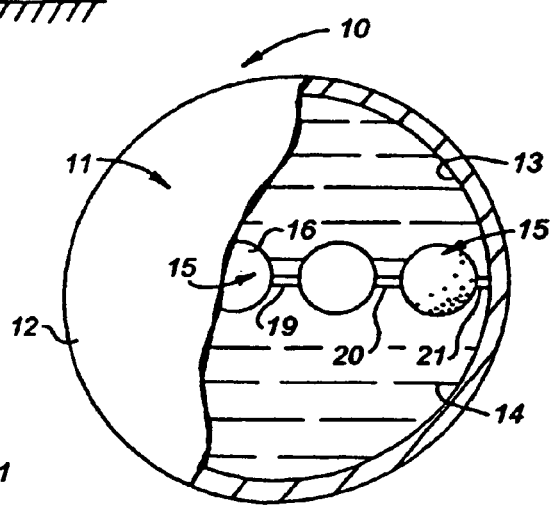
FIG. 2 is an elevation view illustrating an alternate embodiment of the invention.

The heat transfer device of FIG. 2 is identical to that of FIG. 1 except that auxiliary containers 15 are connected in a chain to each other and to the inner surface of wall 13 by links 19, 20, and 21, respectively. This chain can be slack so that containers 15 can, to a degree, move about in liquid 14, or, the chain can be substantially rigid so it maintains its shape and dimension even if pliable wall 11 is displaced.

Figure 3:
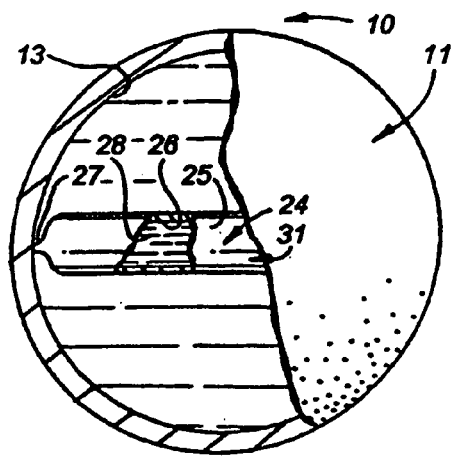
FIG. 3 is an elevation view illustrating yet another embodiment of the invention.

The heat transfer device of FIG. 3 is identical to that of FIG. 1 except that auxiliary containers 15 are removed and replaced by an elongate hollow auxiliary container 31 having a cylindrical wall 24 with a cylindrical outer surface 25 and a cylindrical inner surface 26. Container 31 is filled with a liquid 28 which, like liquid 18, has a freezing point which is greater (warmer) than that of liquid 14. In another embodiment of the invention, liquids 18 and/or 28 have a freezing point which is less than that of liquid 14. This embodiment of the invention is particularly desirable if liquid 14, when frozen, is malleable or is readily broken into pieces which permit a pliable wall 13 to be displaced and manipulated like the pliable rubber wall of a hot water bottle can be manipulated when the water bottle is filled with water In a further embodiment of the invention, liquids 18 and/or 28 have a freezing point equivalent to that of liquid 14.

The use of the devices of FIGS. 2 and 3 is comparable to that of the heat transfer device of FIG. 1. In FIG. 2, auxiliary containers 15 absorb heat from liquid 14. In FIG. 3, auxiliary container 31 absorbs heat from liquid 14.

The ratio of the mass of liquid 14 with respect to the mass of liquid 18 (or 28) in a device 10 can vary as desired, but is presently preferably about 1:1. As the mass of liquid 18 with respect to the mass of liquid 14 increases, the heat absorbing capacity of liquid 18 increases, but there is less of liquid 14 to circulate to containers 15 heat which is absorbed from wall 11. It is believed that if the mass of liquid 18 greatly exceeds that of liquid 14 (e.g., the ratio of liquid 18 to liquid 14 is, for example, 8:1), then heat will tend to be absorbed directly by containers 15 instead of first being absorbed by liquid 14 and transferred to containers 15. This would defeat a primary feature of the invention. The use of liquid 14 to circulate heat to containers 15 is believed central to the invention and is believed, at least in part, responsible for why the heat transfer apparatus of the invention stays cold for unusually long periods of time. The ratio of liquid 18 to liquid 14 is preferably, but not necessarily, in the range of 3:1 to 1:3, most preferably in the range of 2:1 to 1:2.

The materials utilized to construct walls 11 and 30 and 24 affect the rate of heat transfer. Thicker walls normally transfer heat at a slower rate; thinner walls at a faster rate. While polymer material is desirable in walls 11, 24, 30 because pliable polymer materials are readily available, incorporating metal or other materials which facilitate the transfer of heat is also desirable.

When a device 10 is placed in a freezer to solidify liquid 18, liquid 14 can have a composition which permits it to turn to a gel, but preferably does not solidify. It is preferred that liquid 14 remain a liquid or become a gel so that device 10 remains pliable after being frozen. Similarly, when liquid 18 is frozen, it may turn to a gel and may not completely solidify.

The following example is given by way of demonstration and not limitation of the scope of the invention.

EXAMPLE I

The following were obtained:
1. A twelve inch long by twelve inch wide "THERA-PAC"™ two ply vinyl "cold pack" containing a white odorless insoluble gelatin. This cold pack was identified as "A".
2. A twelve inch long by twelve inch wide "COLPAC" ™ single ply plastic "cold pack" filled with a gray odorless soluble gelatin. This cold pack was identified as "B".
3. A cold pack was constructed in accordance with the invention and comprised a ten inch long by ten inch wide two ply plastic container filled with one and three-fourths pounds of propylene glycol and a plurality of small elastic liquid-filled rubber containers each having a diameter in the range of one inch to one and one-quarter inches. The liquid in each of the small rubber containers was water. One and three-fourths pounds of water was used to fill the small rubber containers, i.e., each small rubber container contained significantly less than one and three-fourths pounds of water, and, if all the water in all of the small rubber containers were poured in a container, the water would have weighed one and three-fourth pounds. The rubber containers could move about freely in the propylene glycol. Each ply in the plastic bag had a thickness of about two to three mils. The wall thickness of each rubber container was about two to three mils. This cold pack was identified as "C".

Cold packs A, B, C were all placed at the same time in a freezer. After several hours, cold packs A, B, C were removed at the same time from the freezer and placed on a flat table top in a room. The room temperature was eighty degrees and was maintained at eighty degrees while the following measurements were made. Measurements were made when the cold packs were removed from the freezer and at hourly intervals thereafter up to four hours. Each time measurements were taken, a measurement was taken on the outer surface of each cold pack and on the interior of each cold pack. The results are summarized below in Tables I and II.

TABLE I

Surface Temperature Measurements of Cold Packs A, B, C

| | Temperature Measurements (Degrees F.) | | | | |
|---|---|---|---|---|---|
| Cold Pack | At removal | 1 hour | 2 hours | 3 hours | 4 hours |
| A | 5 | 48 | 56 | 72 | 77 |
| B | 5 | 47 | 55 | 73 | 80 |
| C | 10 | 39 | 39 | 40 | 42 |

TABLE II

Interior Temperature Measurements of Cold Packs A, B, C

| | Temperature Measurements (Degrees F.) | | | | |
|---|---|---|---|---|---|
| Cold Pack | At removal | 1 hour | 2 hours | 3 hours | 4 hours |
| A | 0 | 47 | 55 | 65 | 75 |
| B | 0 | 49 | 57 | 65 | 75 |
| C | 15 | 15 | 32 | 34 | 36 |

The above results demonstrate that the cold pack of the invention (identified as "C") remained much colder for much longer than the conventional cold packs identified as "A" and "B". These results were surprising and unexpected and are believed to demonstrate the utility and novelty of the heat transfer device of the invention.

Figure 4:
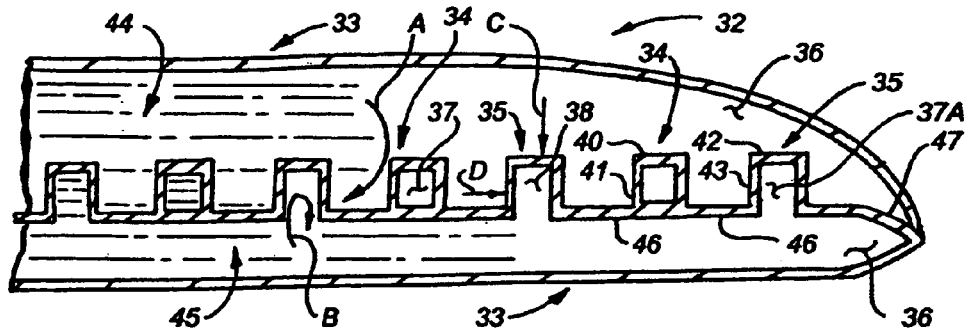
FIG. 4 is a side section elevation view illustrating still a further embodiment of the invention.

Another heat transfer device of the invention is illustrated in FIG. 4 and is generally indicated by reference character 32. Device 32 includes outer wall 33. The material(s) used to fabricate wall 33 can vary as desired. Wall 33 presently preferably comprises a pliable water impermeable material like rubber or plastic. Wall 33 circumscribes and encloses inner space 36. Cylindrical hollow fluid containers 34 and 35 are mounted in inner space 36. The shape and dimension of each container 34, 35 can vary as desired. Each container 34 is fluid tight and completely encloses a space 37. Each container 35 partially encloses a space 38 and opens into the lower portion of inner space 36 in FIG. 4. Each container 35 can be mounted on floor 46 in an inverted configuration in which space 38 opens into the upper portion—instead of the lower portion—of space 36. Each container 34 includes a top 40 and side 41. The thickness of top 40 and side 41 can vary as desired to vary the ability of heat to traverse and pass through top 40 and side 41.

Containers 34, 35 are mounted on a floor 46 that extends across and bifurcates inner space 36 into two separate chambers or spaces. The outer peripheral edge of floor 46 is attached to wall 33. A first heat-exchange composition 44 is in the upper chamber created in space 36 by floor 46. A second heat-exchange composition 45 is in the lower chamber created in space 36 by floor 46. Floor 46 and containers 34 and 35 prevent composition 44 from intermixing with composition 45, and vice-versa. If desired, floor 46 can be perforated to allow the flow of fluid 44 into fluid 45, and vice-versa.

The freezing point of composition 44 can vary as desired and can be equal to that of composition 45, greater than that of composition 45, or less than that of composition 45. In one presently preferred embodiment, the freezing point of composition 44 is lower than that of composition 45. Composition 44 can be the same as composition 45. It is presently preferred, although not necessary, that compositions 44 and 45 be in a liquid phase when heated to normal room temperature of 76 degrees F.; that composition 45 freeze at temperatures in the range of fifteen degrees Fahrenheit to thirty-two degrees Fahrenheit; and, that composition 44 freeze at temperatures less than fifteen degrees Fahrenheit. In this configuration, composition 45 normally freezes when placed in a conventional residential freezer while composition 44 does not. Since composition 44 then remains in a liquid state and since wall 33 normally is pliable, wall 33 and composition 44 can readily conform to a surface (i.e., the body of a human being or other animal) even if composition 45 is, when frozen, rigid.

A third heat-exchange chemical composition can be in space 37 in each fluid tight container 34. The third composition can be a gas, liquid, or solid and can have any desired phase transformation temperatures. Practically speaking, however, the third composition is, as are the first and second heat-exchange compositions, preferably a fluid at room temperature because the heat-exchange compositions preferred in the practice of the invention either remain in a fluid form or transform between only two phases, the liquid phase and the solid phase of the heat-exchange composition. Gases have minimal thermal capacity and ordinarily are difficult to transform into liquids or solids at normal ambient, freezing or heating temperatures.

When the upper portion of wall 33 in FIG. 4 is placed against a substance having a temperature cooler than that of an aqueous liquid composition 44, heat from composition 44 travels outwardly through wall 33 causing the temperature of the portion of composition 44 adjacent wall 33 to cool. When the composition 44 cools, the density of the cooled liquid increases, causing the liquid to move downwardly under gravity in a convection current in the direction of arrow A.

When the lower portion of wall 33 in FIG. 4 is placed against a substance having a temperature warmer than that of a liquid composition 45, heat from the substance is absorbed by composition 45 through the lower portion of wall 33. The warmed portion of composition 45 typically carries the heat by convection upwardly in the direction indicated by arrow B. Fluid circulating in the manner indicated by arrows A and B travels adjacent the sides 41, 43 and tops 40, 42 of containers 34 and 35, permitting heat to travel through the containers between compositions 44 and 45. The shape and configuration of containers 34 and 35 is important in this respect. A plurality of spaced apart containers 34 and 35 is preferred because the upstanding sides 41, 43 significantly increase the surface area available to compositions 44 and 45. Further, when sides 41 and 43 are substantially normal to floor 46 and top 40 or 42, heat can be absorbed substantially vertically through a top 40, 42 or floor 46 in the direction indicated by arrow C and can be absorbed substantially laterally through a side 41 and 43. A side 41, 43 is substantially normal to floor 46 or top, 40, 42 if the side is at an angle in the range of sixty to one-hundred and twenty degrees, preferably in the range of seventy-five to one-hundred and five degrees, to floor 46 or top 40, 42. In FIG. 4, sides 41 and 43 are normal to tops 40, 42 and floor 46. Another reason containers 34 and 35 are preferred is that when fluid flows between containers 34 and 35 or into a container 35, turbulent flow and eddy currents are believed more likely to occur, particularly if the distance between adjacent containers is one inch or less. Turbulent flow and eddy currents facilitate the intermixing of warmed fluid 44 (or 45) with cooler fluid 44 (or 45). This intermixing of fluid 44 having different temperatures facilitates the efficient transfer of heat from a substance to fluid 44 and from fluid 44 either through containers 34, 35 to composition 45 or to a third composition in spaces 37 in containers 34. Heat can also, if desired, transfer from composition 45 to fluid 44 in the event that composition 45 is used to absorb heat.

Another preferred feature of containers 34 and 35 is that each container have substantial dimensional parity. Dimension parity is important because it slows the absorption of heat by the container 34 and 35. Slowing the absorption of heat tends to extend the useful life of device 32 as a cooling device. If containers 34 and 35 do not have dimensional parity and instead take on the configuration of a sheet or panel, the composition in each container 34, 35 tends to more rapidly absorb heat. A container 34, 35 has dimensional parity when the height and width of a cross-section taken through the center (or estimated center) of the container and normal to the length (i.e., normal to the greatest dimension of the container) are substantially equal. The height and width of such a cross-section of the container are substantially equal when the ratio of the height to the width is in the range of 5:1 to 1:5, preferably 3:1 to 1:3. A sphere has substantial dimensional parity because the height and width of a cross-section through the center of the sphere are equal, i.e., are each equal the diameter of the sphere. Therefore, for a sphere, the ratio of the height of the cross-section to the width of the cross-section is 1:1. A cube has substantial dimensional parity because the ratio of the height to the width of a cross-section that passes through the center of the cube, passes through four of the corners of the cube, and is normal to a centerline passing through two corners of the cube is 1:1.

A parallelepiped that is 4 cm high, 6 cm wide, and 8 cm long has substantial dimensional parity because the ratio of height to the width of a cross-section taken through the center and normal to the longitudinal centerline of the parallelepiped 1:1.5.

A parallelepiped which is in the shape of a panel and has a length of 8 cm, height of 4 cm, and a width of 0.5 cm does not have substantial dimensional parity because the ratio of the height to the width of a cross-section taken through the center and normal to the longitudinal centerline of the parallelepiped is 8:1 (i.e., is 4 to 0.5). This parallelepiped would, because of its narrow width, more rapidly absorb heat and dissipate the thermal absorption capacity of the composition in or comprising the parallelepiped.

Figure 5:
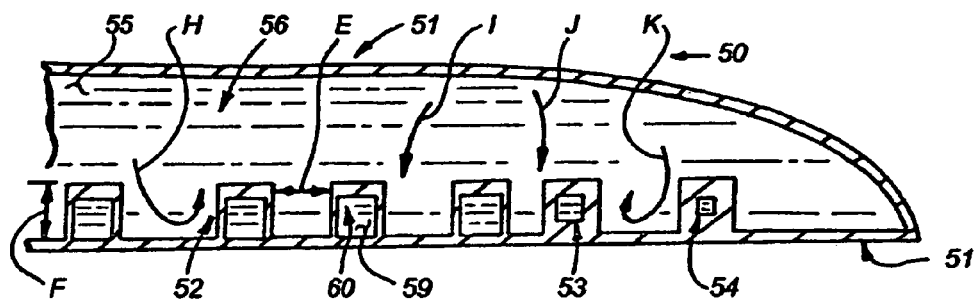
FIG. 5 is a side section elevation view illustrating still another embodiment of the invention.

When the side 41, 43 and top 40, 42 of a container 34, 35 are thin-walled, i.e., are less than about two millimeters (mm) thick (i.e., having a thickness of two mm plus or minus 10%), and have a substantially uniform thickness (i.e., the thickness of the side(s), top, and, if appropriate, bottom, walls at all points varies by no more than about two millimeters), then the outer dimensions of the container provide a good indication of whether the container has substantial dimensional parity. If, however, the thickness of a wall(s) of the container is greater than about two mm and/or the thickness of the walls is not substantially uniform, then the outer dimensions of the container may not provide a good indication of whether the container has substantial dimensional parity, and the configuration of the space 37, 37A inside the container 34, 35 needs to be taken into account to determine if there is substantial dimensional parity. The same criteria used to evaluate the dimensional parity of the outside shape and dimension of a container 34, 35 can be utilized to evaluate the dimensional parity of the space 37, 37A inside a container 34, 35. If the space 37, 37A is the shape of a cube, then the space has dimensional parity. If the space 37, 37A is the shape of a sphere, then the space has dimensional parity. If the space 37, 37A is the shape of a parallelepiped having a length of 8 cm, a height of 4 cm, and a width of 0.5, then the space does not have substantial dimensional parity. In FIG. 5, containers 53 and 54 are not thin-walled. Since, however, the cross-sections of the spaces inside containers 53 and 54 have the shape of a cube, containers 53 and 54 have substantial dimensional parity. The heat transfer container illustrated in U.S. Pat. No. 2,595,328 to Bowen does not appear to have substantial dimensional parity.

Figure 6:
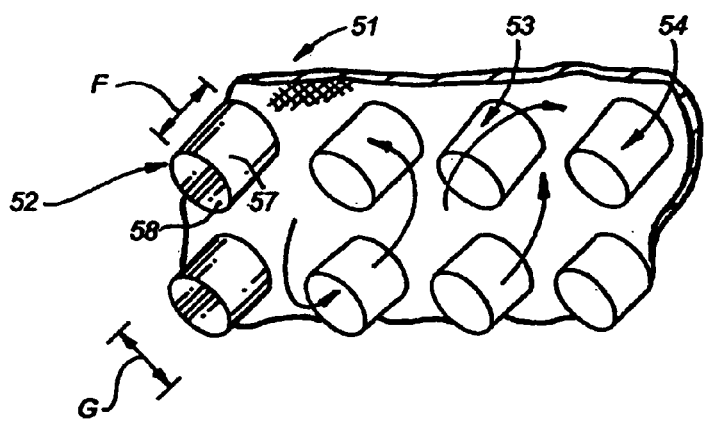
FIG. 6 is a perspective view illustrating a portion of the invention of FIG. 5.

Another heat transfer device 50 is illustrated in FIGS. 5 and 6 and is similar to heat transfer device 32. A particular advantage of device 50 is that it only requires outer liquid impermeable wall 51 and does not require a floor 46 because containers 52, 53, 54 are connected to a portion of wall 51 and extend into space. This makes device 50 inexpensive to manufacture. Each container 52, 53, 54 includes a fluid tight wall 57, a top 58, and a bottom that comprises a portion of wall 51. The inner space 60 of each container includes a heat-exchange composition 60. Inner space 55 is circumscribed and enclosed by wall 51 and includes heat-exchange composition

56. The freezing point of composition 56 can be greater than, less than, or equal to the freezing point of composition 60. In one presently preferred embodiment, the freezing point of composition 60 is a higher temperature than the freezing point of composition 56.

The distance, indicated by arrows E, between an adjacent pair of containers 52 can vary as desired, as can the height, indicated by arrows F, and the width, indicated by arrows G, of a container 52. To facilitate the transfer of heat between compositions 56 and 60, it is preferred that a plurality of containers 52 be provided. As the number of containers 52 increases, the available surface area increases. By way of example, and not limitation, containers 52 presently preferably have a width G in the range of one-quarter to one inch, and a height G in the range of one-quarter to one inch. This distance E between adjacent containers is in the range of one-quarter to three-quarters of an inch. Arrows H to K in FIG. 5 illustrate possible liquid flow paths. Liquid traveling along these flow paths transports heat by convection away from wall 51 toward containers 52, 53, 54.

Figure 7:
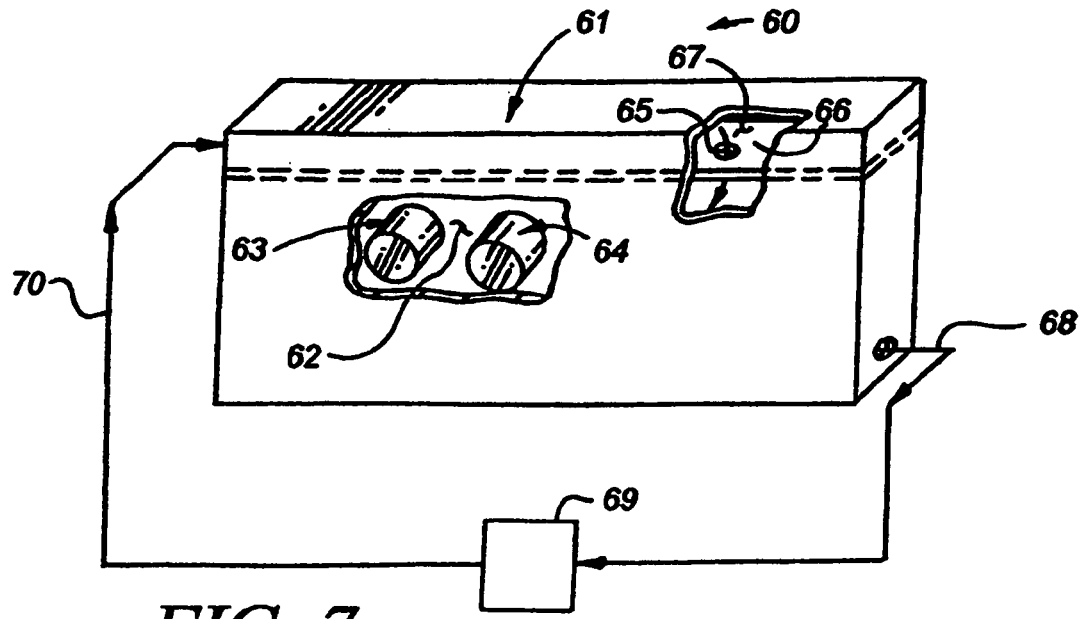
FIG. 7 is a perspective view illustrating yet a further embodiment of the invention.

Heat transfer device 60 in FIG. 7 includes parallelepiped wall 61 circumscribing and enclosing inner spaces 62 and 67 and hollow fluid tight containers 63, 64 mounted on wall 62. A heat-exchange fluid or solid is in each container 63, 64. Rectangular plate 66 separates spaces 62 and 67. Pump 69 circulates a heat-exchange liquid. The liquid flows out of space 62 in the direction of arrows 68, through pump 69, and back into space 67 in the direction of travel indicated by arrows 70. Liquid flowing into space 67 flows through perforations 65 back into space 62.

Figure 8:
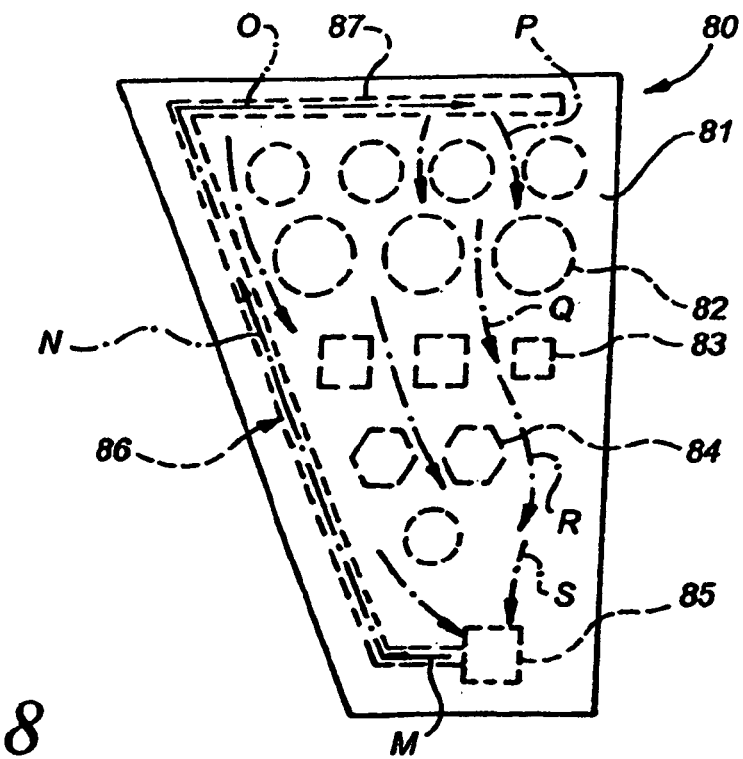
FIG. 8 is a top view illustrating yet another embodiment of the invention.

Heat transfer device 80 in FIG. 8 includes outer wall 81. Walls 61, 81 normally, but not necessarily, are liquid impermeable. Hollow fluid tight containers 82, 83, 84 are housed within wall 81, are mounted on wall 81, and extend into the inner space circumscribed by wall 81 in the same manner that containers 52, 53, 54 are attached to wall 51 and extend into space 55 in FIGS. 5 and 6. The inner space circumscribed by wall 81 is filled with a first heat-exchange composition. Each container 82 to 84 is filled with a second heat-exchange composition. When the first heat-exchange composition is in a fluid phase, pump 85 circulates the first heat-exchange composition. The first heat-exchange composition exits pump 85 and travels through conduit 86 in the manner indicated by arrows M, N, O. The upper arm 87 of conduit 86 is perforated such that fluid exits arm 87 under pressure in the direction indicated by arrow P. The perforations are shaped and spaced to facilitate a uniform rate of dispersal of fluid out of arm 87 along the length of arm 87, or along a selected portion of the length of arm 87. The first heat-exchange composition flows around and between containers 82, 38, 84 in the manner indicated by arrows Q, R, S and re-enters pump 85, which again directs the composition into conduit 86 under pressure.

Walls 33 and 51 and 61 and 81, floor 46, and containers 34, 35, 52, 53, 54, 63, 64, 82, 83, 84 can be rigid or flexible or pliable, elastic or non-elastic, porous or non-porous, fluid tight or not fluid tight, have one or more layers, and can be constructed from any desired material including, without limitation, resin, metal, glass, concrete, plaster, porcelain, and paper.

As earlier noted, fluid can be circulated in the heat transfer device of the invention by convection and by the use of a pump. Fluid can also be circulated by shaking the heat transfer device and by, when the outer wall 33, 51, 61, 81 is pliable, manually kneading or displacing the wall to move the heat-exchange composition 44, 56 in the device.

As will be appreciated by those of skill in the art, in FIG. 4 either the top or bottom of wall 33 can be placed against a surface to be heated or cooled. In FIG. 4, only containers 34 or only containers 35 can, if desired, be utilized and mounted on floor 46.

In one embodiment of the invention, the containers 52 in FIG. 5 each are cylindrically shaped, are of equivalent shape and dimension, have a diameter and height of about one-half inch, are equidistant from other adjacent containers, and are spaced apart about one-half inch in a checker board array similar to that shown in FIG. 6.

In FIG. 4, containers 34, 35 approximately double the surface area exposed to composition 44. If containers 34, 35 are not utilized and floor 46 is a flat, continuous member extending completely across device 32, then the surface area exposed to composition 44 is about equal to the sum of the area of the tops 40, 42 of the containers 34, 35 and the area of the portions of floor 46 extending intermediate containers 34, 35 in the manner shown in FIG. 4. When containers 34, 35 are utilized, the surface area exposed to composition 44 equals the sum of the area of tops 40, 42 plus the area of the portions of floor 46 extending intermediate containers 34, 35 plus the sum of the cylindrical surface areas of each side 41, 43. 100% of the surface area of each container 35 is in contact with composition 44. All of the surface area of each container 34 is in contact with composition 44 excepting the circular base, which is in contact with composition 45. The proportion of the surface area of each container 34, in contact with composition 44 or 45 is in the range of 20% to 100%, preferably in the range of 55% to 100%, most preferably in the range of 70% to 100%. In U.S. Pat. No. 2,595,328 to Bowen, only 50% of each receptacle 8 is in contact with material 7 positioned above receptacle 8. The more desirable embodiments of the invention illustrated in FIGS. 4 and 5 herein utilize containers 34, 35 having well over 50% of the containers in contact with composition 44 and/or 45.

The use of containers 34, 35, 52, etc. that remain in fixed position comprises one preferred embodiment of the invention because the containers 34, 35, 52 are prevented from bunching together. This insures that the heat transfer characteristics of the heat transfer device remain fixed and more evenly distributed throughout the device.

Another important feature of the invention is the proportion of the surface area of floor 46 (or of the bottom area of a wall 51 on which containers 52, 53, 54 are mounted in FIG. 5) intermediate containers 34, 35 with respect to the surface area of floor 46 occupied by the base of each container 52, 53. This is important because there must be sufficient space intermediate containers 52, 53 to permit fluid to circulate in the manner indicated by arrows A and B (and arrows H to K in FIG. 5) so heat can be transferred through floor 46 to fluid 45 and/or through walls 41 and 43 to fluid 45 or to fluid in spaces 37. U.S. Pat. No. 2,595,328 discloses a heat transfer device which has little floor space (zones 9 in Bowen) and, consequently, which permits little lateral heat transfer and little heat transfer through zones 9. The ratio of the surface area of floor 46 intermediate containers 34, 35 to the surface area of the bases of containers 35, 35 (where in FIG. 4 the surface area of each base of a cylindrical containers 34, 35 is equal to the surface area of the top 40, 42 of the container) is in the range of 1:3.5 to 10:1, preferably 1:2 to 10:1.

Similarly the proportion of the surface area of containers 34, 35 that permits lateral heat transfer D is important in the practice of the invention. The proportion of the surface area of the side(s) of a container 34, 35 to the total surface area of the container is in the range of 1:4 to 10:1. The receptacles 8 in U.S. Pat. No. 2,595,328 to Bowen are not constructed to significantly utilize lateral heat transfer. The total surface area of container 35 herein includes the area of top 42 plus the area of side 43. The total surface area of container 34 includes the surface area of circular top 40, the surface area of cylindrical side 41, and the area of the circular base of container 34. If the proportion of the surface area of the side(s) of a container 34, 35 with respect to the total surface area of the container is too great (i.e., is, for example, 12:1), then it is likely the container is either losing dimensional parity or is so tall that it interferes with proper fluid circulation. Similarly if the proportion of the surface area of the side(s) of a container 34, 35 with respect to the total surface area of the container is too small (i.e., is for example 1:6), then it is also likely the container is losing dimensional parity and/or is so short that the lateral heat absorption D is adversely affected.

In one preferred embodiment of the invention, fluid 56 has a lower freezing point than the fluid in containers 52. For example, fluid 56 is glycol and the fluid 60 in containers 52 is water. Device 50 is placed in a conventional residential freezer in a refrigerator. Fluid 60 freezes. Fluid 56 does not. The upper portion of wall 51 in FIG. 5 is placed against the back of the neck of an individual. Since fluid 56 is in a liquid state, fluid 56 and the upper portion of pliable wall 51 readily conform to the shape of individual's neck (or shoulder, or arm, etc.). Fluid 56 absorbs heat. Convection currents H to K carry heat toward containers 52. The shape and dimension and spacing of containers 52 cause turbulent flow and eddy current when the convection currents flow into, past, and between containers 52. Frozen fluid 60 absorbs heat. Eventually a large enough quantity of heat is absorbed to cause frozen fluid 60 to undergo a phase transformation from a solid to a liquid.

Figure 9:
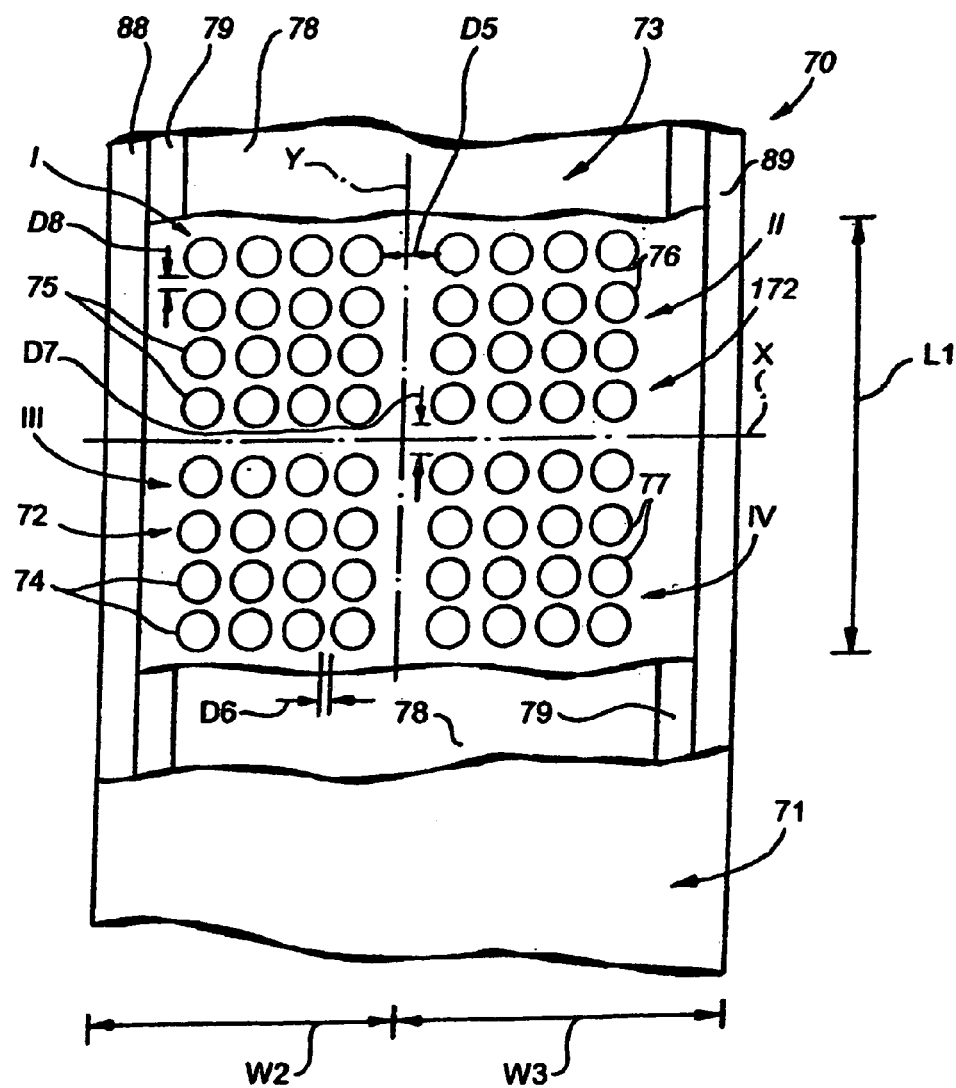
FIG. 9 is a top view illustrating still a further embodiment of the invention.

FIG. 9 illustrates another heat transfer device 70 constructed in accordance with the principles of the invention. Device 70 includes a pan 73, a module matrix 72, and a seal layer 71.

Pan 73 includes bottom 78 and includes outer parallel elongate planar lips or edges 88 and 89 and includes inner parallel inset elongate planar lips or edges 79. The construction of lips or edges 88, 89, 79 is similar to the construction of lips or edges 88A, 89A, 79A and 79B in pan 173A in FIG. 10C. The construction of pan 73 is similar to that of pan 173A.

Module matrix 72 includes a plurality of modules 74, 75, 76, 77. In FIG. 9 there are sixteen equal sized modules 75 in an upper left hand quadrant I, sixteen equal sized modules 76 in an upper right hand quadrant II, sixteen modules 74 in a lower left hand quadrant III, and sixteen modules 77 in a lower right hand quadrant IV. The shape and dimension of each module can, if desired, vary. However, in FIG. 9 each module 74, 75, 76, 77 has an equivalent shape and dimension. Adjacent modules 75 in the upper left hand quadrant are spaced equal distances apart, as are adjacent modules 75 to 77 in the remaining three quadrant illustrated in FIG. 9. If desired, module matrix 72 can, and likely would, include additional modules, preferably, but not necessarily, in submatrix groupings of four by four (or sixteen total) modules.

One particular advantage of module matrix 172 is that each quadrant I, II, III, IV of sixteen modules is spaced apart from any adjacent modules such that the distance indicated by arrows D5 and D7 is greater than the distance D6 between modules in a quadrant. This facilitates folding or cutting device 70 along axis X and/or Y.

Another advantage of module matrix 172 is that each module 74 to 77 has a semi-spherical, cylindrical, semi-ellipsoidal, semi-spheroidal or other arcuate bottom like modules 77A in FIGS. 11B and 11C. Providing modules 74 to 77 with arcuate bottoms facilitates pliably bending or deforming device 70 in the manner indicated by arrows 201 and 202 in FIG. 10D for heat transfer device 170. The arcuate bottoms of each module 74 to 77 also facilitate the flow of fluid around the bottoms.

The peripheral edges of seal layer 71 are fixedly sealingly connected to lips 88, 89 to seal liquid (not visible in FIG. 9) that fills pan 73 and surrounds modules 74, 75, 76, 77 and that fills each module 74, 75, 76, 77. Layer 71 is sealingly affixed to edges 88 and 89 in the same manner that layer 71A is affixed to edges 89A and 88A in FIG. 10D.

While distance D5 can vary as desired, D5 is presently preferably in the range of 16 mm to 24 mm. The distance D6, D2, D8 between a pair of adjacent modules 74 in a quadrant can vary but is presently preferably eight millimeters to twelve millimeters. The diameter or width W1 (FIG. 11C) of a module can vary but is presently preferably in the range of 20 mm to 40 mm. The depth D1 (FIG. 11C) of a module is preferably equal to or about equal to the width of the module. The bottom 77C (FIG. 10D) of a module can contact or need not contact the bottom 78, 78A of a pan 73, 173A.

A procedure for fabricating a heat transfer device similar to that depicted in FIG. 9 is illustrated FIGS. 10A to 10D and 11A to 11C.

In FIG. 10A, a deformable pliable sheet 73A of a polymer or some other material is provided along with a mold 91. Mold 91 includes apertures 92. Apparatus (not shown) draws air out from the inside of mold 91 through apertures 92 in the direction indicated by arrow L to draw sheet 73A into the mold and to contour sheet 73A to the inner surface 91A of the mold. A follower 90 is also provided to assist sheet 73A in contouring to surface 91A. After suction is applied to draw air in the direction of arrow L and follower 90 is simultaneously moved downwardly in the direction of arrow T, sheet 73A contours to inner surface 91A in the manner illustrated in 10B and a pan 173A is formed.

In FIG. 10B, pan 173A includes bottom 78A, includes elongate, parallel spaced apart inset edges 79A and 79B, and includes elongate, parallel, spaced apart outer edges 88A and 89A.

In FIG. 10C, follower 90 has been removed and nozzle 93 is utilized to inject fluid into pan 173A to form a reservoir 94.

The module matrix 172A produced using the steps illustrated in FIGS. 11A to 11C is inserted in pan 173A in FIG. 10D.

In FIG. 11A, a deformable pliable sheet 72A of a polymer or some other material is provided along with a mold 96. Mold 96 includes openings 97. Each opening 97 includes an upright cylindrical wall and a semi-spherical bottom. Apparatus (not shown) draws air out from the inside of mold 96 through apertures 97 in the direction indicated by arrow U to draw sheet 72A into the mold and to contour sheet 72A to the inner surfaces 96A of the mold. A follower 95 is also provided to assist sheet 72A in contouring to cupped surfaces 96A. After suction is applied to draw air in the direction of arrow U and follower 95 is simultaneously moved downwardly in the direction of arrow V, sheet 72A is contoured to inner surfaces 96A in the manner illustrated in 11B and a module matrix 172A is formed.

In FIG. 11B, module matrix 172A includes modules 77A.

In FIG. 11C, follower 95 has been removed and nozzles 99 are utilized to inject fluid into modules 77A to form a reservoir 98 in each module 77A. The fluid charged module matrix 172A is inserted in the pan 173A of FIG. 10 to produce the module matrix 172A—pan 173A combination illustrated in FIG. 10D. After the module matrix 172A is inserted in pan 173A in the manner illustrated in FIG. 10D, a layer 71A is applied to seal the fluid reservoirs 98, 94 to complete the production of a heat transfer device in accordance with the invention. Layer 71A is continuously sealed to outer edges 88A and 89A.

If desired, module matrix 172A can be inserted in the pan 173A of FIG. 10C before each module 77A is charged with fluid to form reservoirs 98. Or, a auxiliary layer similar to layer 71A can be applied to module matrix 172A before matrix 172 A is inserted in pan 173A. This auxiliary layer would seal fluid reservoirs 98 in the matrix 172A. After this sealed matrix 172A is inserted in pan 173A, then layer 71A is applied to seal matrix 172A and reservoir 94 in pan 173A.

As earlier discussed, the fluid in reservoirs 98 normally preferably has a different freezing tempering than the fluid in reservoir 94.

In FIG. 9, the fluid in pan 73 and the fluid in each module 74 to 77 has been omitted for the sake of clarity. The structure of the heat transfer device 70 of FIG. 9 is generally equivalent to the structure of the heat transfer device illustrated in FIG. 10D except, of course, that the heat transfer device in FIG. 10D includes fewer modules than the heat transfer device 70.

Figure 12:
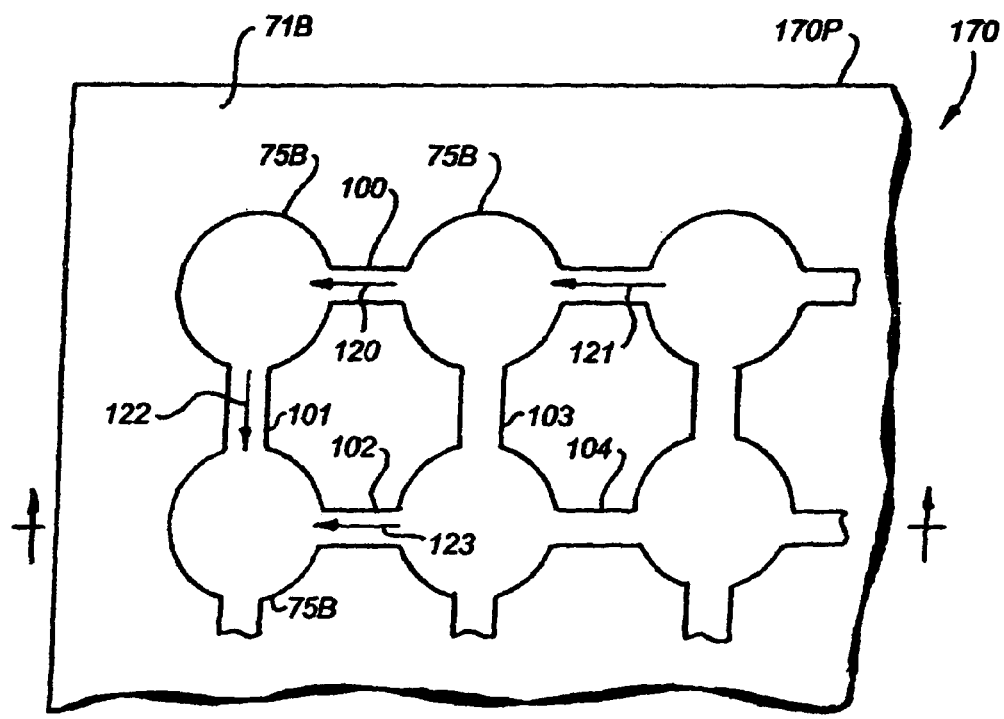
FIG. 12 is a top view illustrating still another embodiment of the invention.
Figure 13:
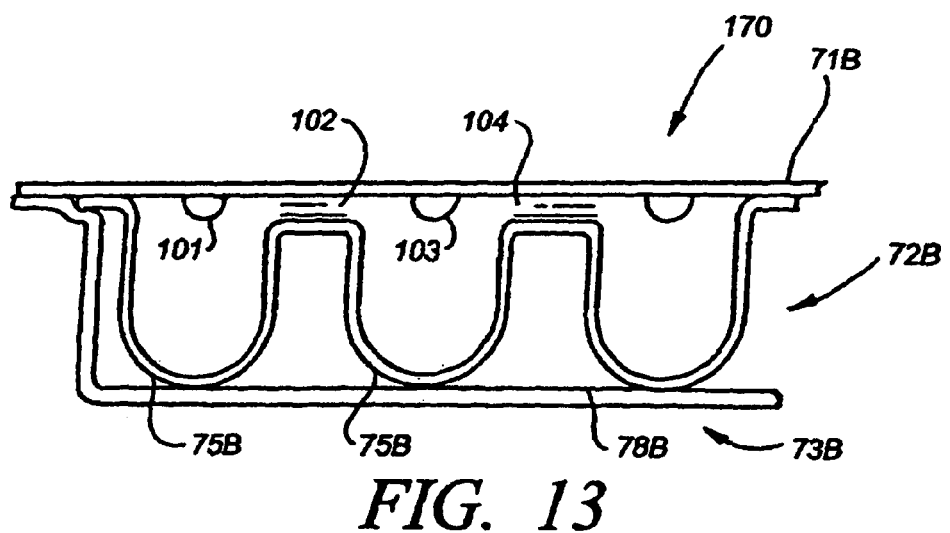
FIG. 13 is a side section view of the apparatus of FIG. 12 and illustrating additional construction features thereof.

FIGS. 12 and 13 illustrate another heat transfer device 170 constructed in accordance with the invention. Device 170 is generally equivalent in structure to heat transfer device 70 and to the heat transfer device of FIG. 10D except that modules 75B in the module matrix 72B are interconnected by semi-cylindrical channels 100, 102, 104. Device 170 includes sealing layer 71B and pan 73B with bottom 78B. The bottom of each module 75B contacts bottom 78B as illustrated in FIG. 13. It is not, however, necessary that the bottom of each module 75B contact bottom 78B. Each module 75B is charged with a liquid (not shown), and pan 73B is charged with a liquid (not shown). The liquid in modules 75B has a different freezing temperature than the liquid in pan 73B. When device 170 is utilized, the liquid in modules 75B near the peripheral edge 170P of device 170 tends to melt first. Since channels 100, 102, 104 permit fluid to flow between modules 75B, channels 100, 102, 104 are believed to facilitate a more uniform distribution of heat into or from device 170. As would be appreciated by those of skill in the art, in FIG. 11A, mold 96 can be shaped and dimensioned to produce a module matrix 172A that would include channels 100, 102, 104.

Figure 14:
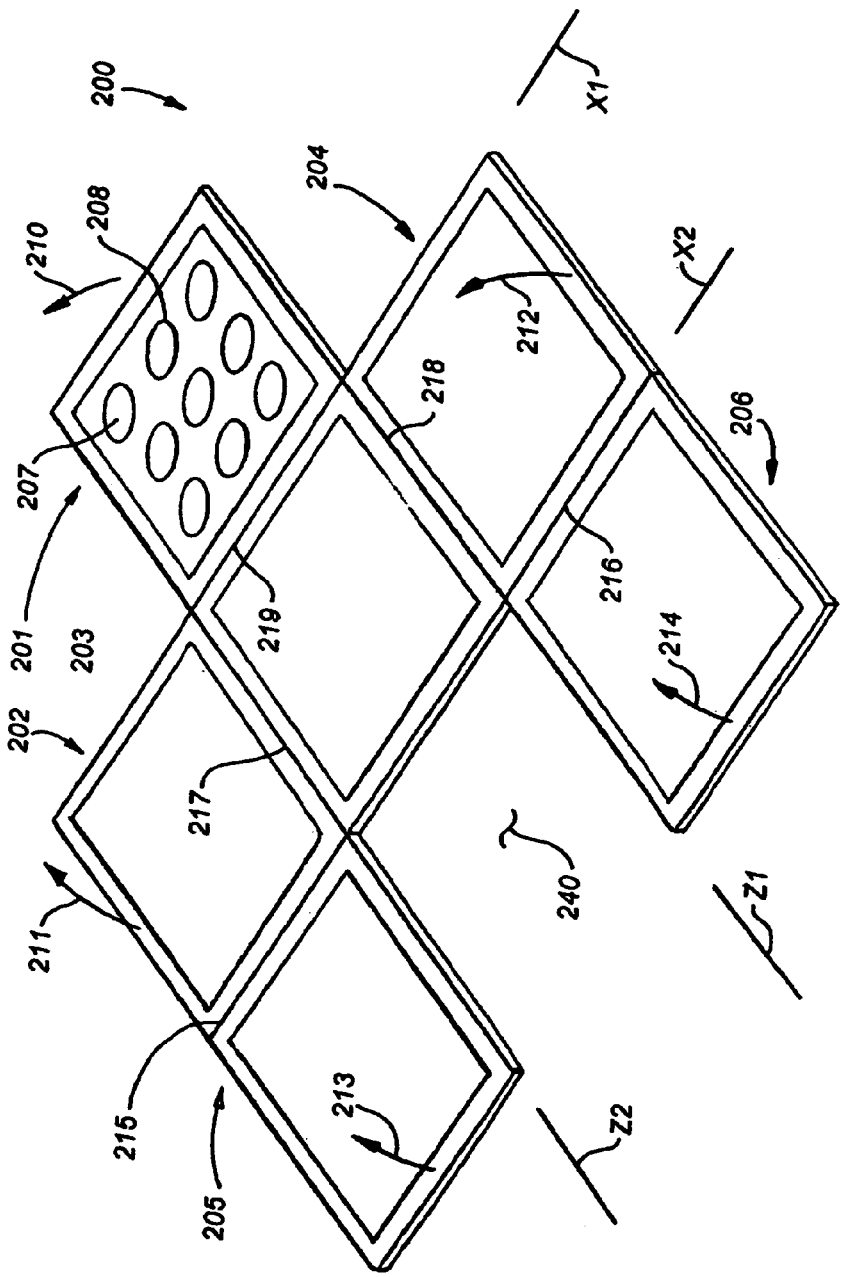
FIG. 14 is a perspective view illustrating an alternate embodiment of the heat transfer device of the invention.

FIG. 14 illustrates a heat transfer device 200 that includes a plurality of module matrices 201, 202, 203, 204, 205, 206. Each matrix 201 to 206 is constructed in a manner similar to that of heat transfer device 170 and includes a plurality of liquid filled modules 207, 208. The modules 207, 208 are not, for sake of clarity, illustrated in matrices 202 to 206. Matrix 201 is attached to matrix 203 along fold line or line of weakening 219. Matrix 204 is attached to matrix 203 along fold line or line of weakening 218. Matrix 202 is attached to matrix 203 along fold line or line of weakening 217. Matrix 205 is attached to matrix 202 along fold line or line of weakening 215. Matrix 206 is attached to matrix 204 along fold line or line of weakening 216.

One important feature of the heat transfer device of FIG. 14 is that adjacent matrices are attached to matrix 203 (and to matrices 202 and 204) along at least two different and separate lines of weakening and extend outwardly from matrix 203 in different directions. This facilitates wrapping the heat transfer device of FIG. 14 around a portion of an individual's body.

Another important feature of the heat transfer device of FIG. 14 is that matrices 202 to 206 form and partially circumscribe an opening 240 shaped to receive the neck or another portion of an individual's body. This construction of the heat transfer device 200 facilitates positioning device 200 in the manner illustrated in FIG. 15 over the shoulders and around the base or back of the neck of an individual 220.

Any desired configuration of matrices 201 to 206 can be employed. Each matrix 210 to 206 may, if desired, be round or triangular or some shape other than the square shape of each matrix 210 to 206 illustrated in FIG. 14. The number of matrices utilized in a heat transfer device 200 can vary. For example, a heat transfer device can be utilized in which matrices 205 and 206 are moved and only matrices 201 to 204 remain in the "T" shape illustrated in FIG. 14.

Any desired means can be provided to detachably secure matrices 200 to 206 to each other. In FIG. 16, a matrix 223 a "hook" VELCRO™ strip 241 is fixedly attached to an edge of matrix 22. A "loop" VELCRO strip 242 is fixedly attached to an edge of matrix 223. Strip 241 is detachably secured to strip 242 to secure matrix 222 to 223 and to form a line along which matrix 222 can be folded or moved with respect to matrix 223. VELCRO strips 243, 244, 245 can be fixedly attached at any desired location(s) on a matrix 222, 223 to facilitate the attachment of the matrix to one or more adjacent matrices. The matrices 201 to 206 in FIG. 14 can, for example, be detachably secured to one another in the configuration shown by using VELCRO, snaps, or any other desired fastening system.

FIG. 17 is a partial section view of the heat transfer matrix 222. The construction of matrix 22 is similar to that of device 170 (FIG. 10D). Matrix 222 includes a pan 232 that presently preferably is fabricated from a pliable polymer. A plurality of modules 225, 227 extend downwardly into pan 232. The modules 225, 227 are presently preferably fabricated from a pliable polymer. Each modules includes an upper circular mouth and a lower end that has the general shape that corresponds to the surface of one-half of a sphere. Each modules 225, 227 is filled with a first heat transfer fluid and is sealed by upper polymer layer 226. The inner space 233 of pan 232 is filled with a second heat transfer fluid. In use, the bottom of pan 232 is placed against a portion of an individual's body. Heat is conducted in the manner indicated by arrow 230 through the bottom of pan 232 and into heat transfer fluid in pan 232. Heat is absorbed by the heat transfer fluid and travels, as indicated by arrow 231, in pan 232 by fluid convection to an area adjacent one of modules 225, 227. Heat is conducted from fluid in pan 232 through a module 227 in the manner indicated by arrow 234 to the heat transfer fluid in the module. Heat is absorbed by fluid in the module 227. The heat absorbed by fluid in module 227 can, if the matrix is constructed in the manner shown in FIG. 12, travel by convection in the manner indicated by arrows 120, 121, 123 from one module (75B in FIG. 12) to another module (75B in FIG. 12). Consequently, a matrix 222 can provide four heat transfer mechanisms, two by conduction and two by convention. The use of four heat transfer mechanisms is important because it facilitate the uniform distribution of heat (and therefore the uniform melting) throughout the matrix 22

I have discovered that particular embodiments of the cooling pack of the invention have usefulness in healing and preventing bodily injuries. These embodiments can be constructed and used according to principles described earlier herein; however, some structural features described below are believed to facilitate use of the cooling pack in healing and preventing injury.

EXAMPLE II

Figure 18:
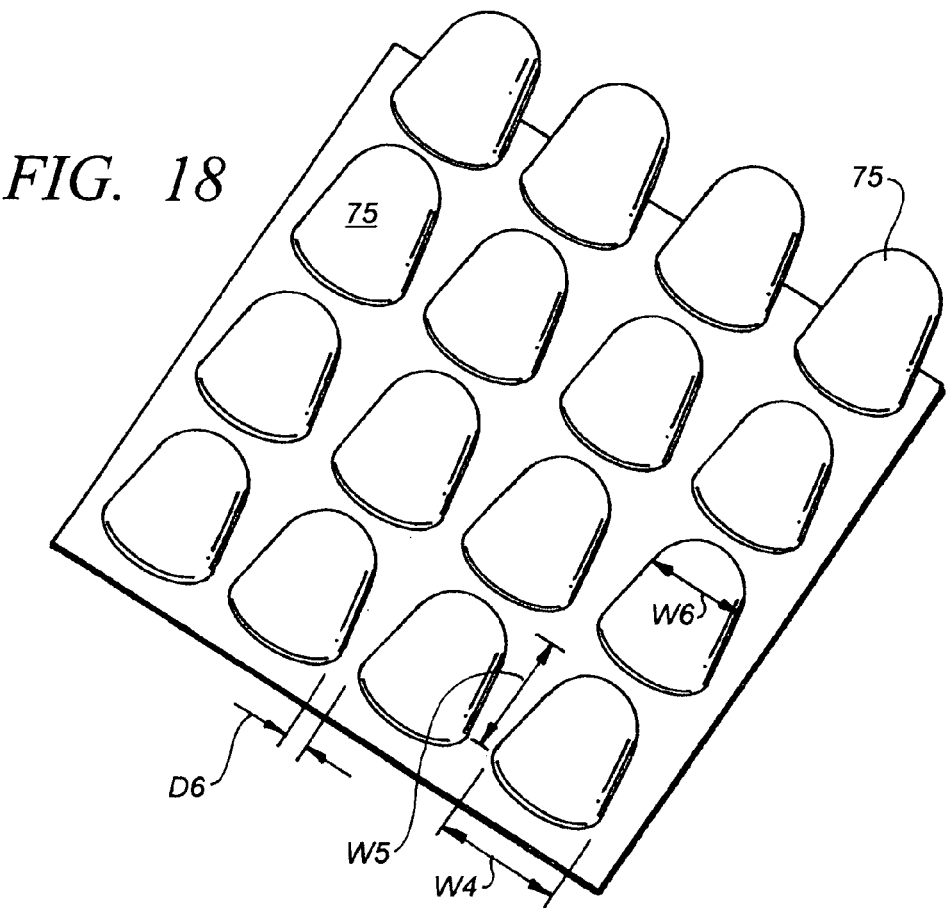
FIG. 18 is a perspective view illustrating the modules and sealing layer in a Cryo Small unit constructed in accordance with the invention.

Cooling apparatus with a structure similar to that illustrated in FIGS. 9 and 10D was constructed in three different sizes, (1) a "Cryo Small" unit consisting of a "single quadrant" of sixteen modules 75 in a configuration corresponding to FIG. 18 and to quadrant I (or II or III or IV) in FIG. 9, (2) a "Cryo Medium" unit corresponding to a pair of quadrants I and II (or III and IV) in FIG. 9 for a total of thirty-two modules 75,76, and (3) a "Cryo Large" unit having four quadrants corresponding to the four quadrant configuration I-IV illustrated in FIG. 9 for a total of sixty-four modules 75, 76, 77, 78. Each of the Cryo Small, Cryo Medium, and Cryo Large units included a pan 78A formed from a pliable deformable polymer sheet 73A and filled with a liquid 94 consisting of a mixture of 22% (in the preferred range of 15% to 25% by weight glycol) by weight glycol and 78% (in the preferred range of 75% to 85% by weight water) by weight water, included a plurality of modules 77A and 77C formed from pliable deformable polymer sheet 72A, and included deformable pliable polymer sheet seal layer 71 sealing a liquid consisting of water 98 in modules 77A and 77C. The weight percent of glycol (or other chemical(s) with a freezing temperature less than water or another selected liquid) in the glycol-water mixture can vary from 60 weight percent to 100 weight percent.

Each module 75 to 78 had a base with an outer base diameter W4 of one inch, a height W5 of one inch, and slightly tapered conical sides extending upwardly to a semi-spherical tip 111 (FIG. 19) having an outer diameter W6 of seven-eighths of an inch. The space D6, D8 between the bases of each adjacent pair of modules was three-eighths of an inch.

Polymer sheets 71A, 72A, 73A (FIG. 10A) initially had, before forming, a thickness in the range of four to ten mils. After forming, the thickness of sheet 73A was 2 mils (in the preferred range of one to six mils); polymer sheet 72A (FIG. 11A) had a thickness of 2 mils (in the preferred range of one to six mils); and, polymer seal layer 71A (FIG. 10D) had a thickness of 2 mils (in the preferred range of one to six mils).

Figure 20:
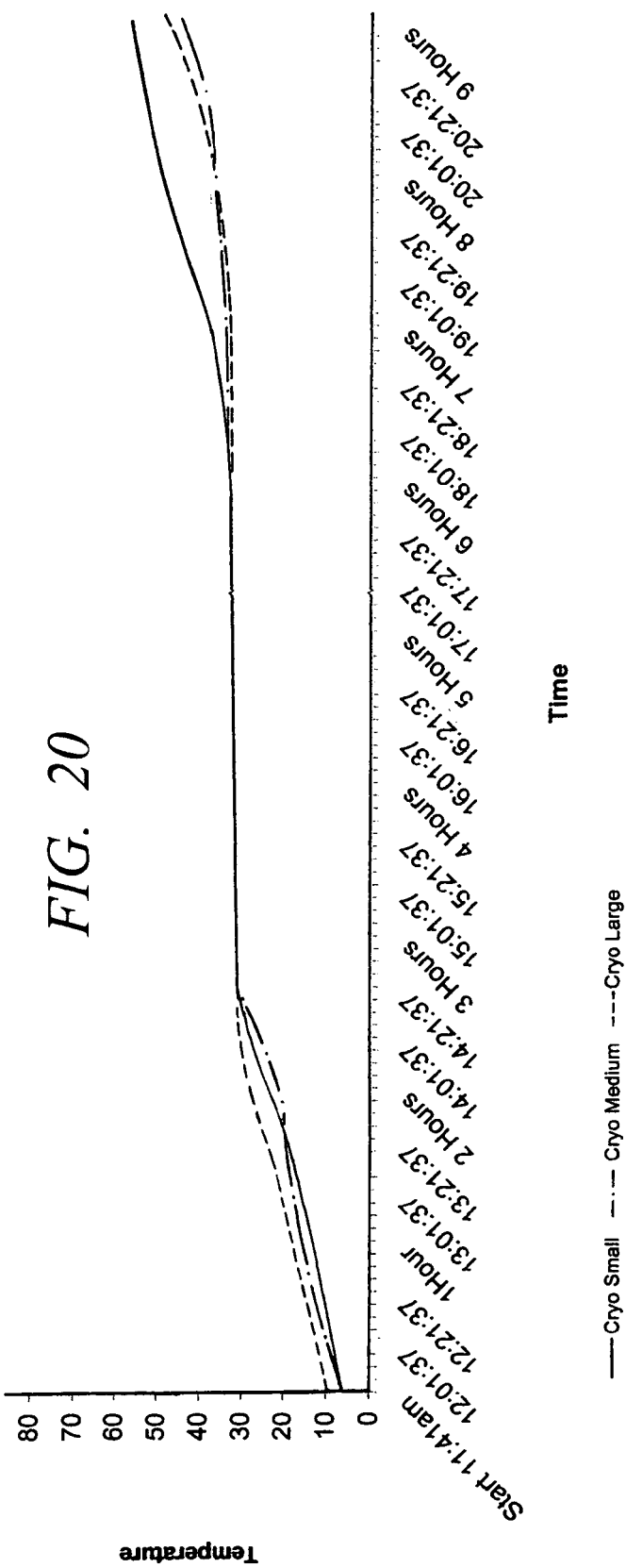
FIG. 20 is a graph illustrating the temperature of Cryo Small, Cryo Medium, and Cryo Large units as they warm at ambient temperature.

The Cryo Small, Cryo Medium and Cryo Large units were placed in a conventional residential freezer until the water in modules 75 to 78 partially froze and formed a partially frozen slush. The Cryo Small, Medium and Large units were then removed from the freeze and placed on a table top in a room having an ambient temperature of sixty-eight degrees F. The temperature of a module 75 to 78 in each unit was monitored. The data obtained is reflected in Table III on the following pages and in the graph illustrated in FIG. 20. The first column in Table III to the right of the time column (the left most column in Table III) is the temperature data in degrees F. for the Cryo Small. The second column to the right of the time column is the temperature data for the Cryo Medium. And the third column to the right of the time column is the temperature data for the Cryo Large. As is demonstrated by the data in Table III, after about two and one-half hours, the temperature of each of the Cryo small, medium, and large units stabilized at about thirty-four degrees, and remained at about that temperature until nearly six hours after the Cryo units had been removed from the freezer. The foregoing procedure of monitoring the temperature of Cryo units after they are removed from a freezer was repeated, except the room temperature was about sixty-two to sixty-eight degrees F. and each Cryo unit was placed in a bag comprised of thin, soft poly fleece fabric. The data obtained is reflected in Table IV, which follows Table III above. The first column in Table IV to the right of the time column (the left most column in Table IV) is the temperature data in degrees F. for the Cryo Small. The second column to the right of the time column is the temperature data for the Cryo Medium. And the third column to the right of the time column is the temperature data for the Cryo Large. The fourth column to the right of the time column is the ambient temperature.

TABLE III

| | 13 | 17.8 | 19 |
|---|---|---|---|
| Start 11:41 am | | | |
| 11:46:37 | 10.4 | 12.9 | 14 |
| 11:51:37 | 11 | 13.3 | 14.5 |
| 11:56:37 | 11.6 | 13.9 | 15.4 |
| 12:01:37 | 12.4 | 14.6 | 16 |
| 12:06:37 | 13.2 | 15.2 | 16.7 |
| 12:11:37 | 14 | 15.9 | 17.4 |
| 12:16:37 | 14.7 | 16.4 | 17.9 |
| 12:21:37 | 15.3 | 17 | 18.4 |
| 12:26:37 | 16.2 | 17.5 | 19.1 |
| 12:31:37 | 16.6 | 18 | 19.7 |
| 12:36:37 | 17.4 | 18.5 | 20.2 |
| 1 Hour | 18 | 18.9 | 20.7 |
| 12:46:37 | 18.5 | 19.4 | 20.9 |
| 12:51:37 | 19.2 | 19.8 | 21.5 |
| 12:56:37 | 19.7 | 20.3 | 22 |
| 13:01:37 | 20.5 | 20.9 | 22.5 |
| 13:06:37 | 20.9 | 21.3 | 23.4 |
| 13:11:37 | 21.6 | 21.6 | 24.3 |
| 13:16:37 | 22.3 | 21.9 | 25.4 |
| 13:21:37 | 23.2 | 22.3 | 26.8 |
| 13:26:37 | 24.1 | 22.7 | 28.2 |
| 13:31:37 | 25.4 | 23.1 | 29.8 |
| 13:36:37 | 27.2 | 23.6 | 31.2 |
| 2 Hours | 28.5 | 24.2 | 32.2 |
| 13:46:37 | 30 | 25 | 33 |
| 13:51:37 | 31.3 | 26 | 33.6 |
| 13:56:37 | 32.4 | 27.6 | 33.6 |
| 14:01:37 | 32.9 | 29.4 | 33.8 |
| 14:06:37 | 33.4 | 30.9 | 33.9 |
| 14:11:37 | 33.6 | 32 | 34 |
| 14:16:37 | 33.7 | 32.9 | 34.2 |
| 14:21:37 | 33.8 | 33.8 | 34.1 |
| 14:26:37 | 33.9 | 33.4 | 34.3 |
| 14:31:37 | 34 | 34 | 34.3 |
| 14:36:37 | 34.1 | 34.2 | 34.2 |
| 3 Hours | 34.2 | 34.5 | 34.1 |
| 14:46:37 | 34.1 | 34.4 | 34.3 |
| 14:51:37 | 34.1 | 34.6 | 34.2 |
| 14:56:37 | 34.1 | 34.4 | 34.4 |
| 15:01:37 | 34.3 | 34.4 | 34.4 |
| 15:06:37 | 34.3 | 34.4 | 34.5 |
| 15:11:37 | 34.3 | 34.5 | 34.5 |
| 15:16:37 | 34.3 | 34.5 | 34.4 |
| 15:21:37 | 34.3 | 34.5 | 34.3 |
| 15:26:37 | 34.2 | 34.6 | 34.3 |
| 15:31:37 | 34.4 | 34.6 | 34.3 |
| 15:36:37 | 34.5 | 34.6 | 34.5 |
| 4 Hours | 34.4 | 34.6 | 34.5 |
| 15:46:37 | 34.3 | 34.7 | 34.5 |
| 15:51:37 | 34.3 | 34.7 | 34.6 |
| 15:56:37 | 34.3 | 34.6 | 34.5 |
| 16:01:37 | 34.4 | 34.5 | 34.5 |
| 16:06:37 | 34.3 | 34.5 | 34.5 |
| 16:11:37 | 34.3 | 34.6 | 34.5 |
| 16:16:37 | 34.2 | 34.6 | 34.5 |
| 16:21:37 | 34.4 | 34.6 | 34.7 |
| 16:26:37 | 34.5 | 34.7 | 34.7 |
| 16:31:37 | 34.5 | 34.6 | 34.6 |
| 16:36:37 | 34.6 | 34.6 | 34.7 |
| 5 Hours | 34.6 | 34.6 | 34.7 |
| 16:46:37 | 34.5 | 34.7 | 34.7 |
| 16:51:37 | 34.6 | 34.7 | 34.8 |
| 16:56:37 | 34.5 | 34.6 | 34.8 |
| 17:01:37 | 34.8 | 34.7 | 34.9 |
| 17:06:37 | 34.7 | 34.7 | 34.8 |
| 17:11:37 | 34.8 | 34.8 | 34.8 |
| 17:16:37 | 34.8 | 34.7 | 34.7 |
| 17:21:37 | 34.9 | 34.8 | 34.9 |
| 17:26:37 | 34.8 | 34.8 | 34.9 |
| 17:31:37 | 35.1 | 35 | 35 |
| 17:36:37 | 35.2 | 35.1 | 35.1 |
| 6 Hours | 35.3 | 35.1 | 35.1 |
| 17:46:37 | 35.8 | 35.1 | 35.2 |
| 17:51:37 | 36 | 36.7 | 35.3 |
| 17:56:37 | 36.2 | 36.7 | 35.4 |
| 18:01:37 | 36.6 | 36.8 | 35.6 |
| 18:06:37 | 36.9 | 36.6 | 35.6 |
| 18:11:37 | 37.4 | 36.7 | 35.8 |

TABLE III-continued

| | | | |
|---|---|---|---|
| 18:16:37 | 38 | 37 | 35.9 |
| 18:21:37 | 38.4 | 37.1 | 36 |
| 18:26:37 | 39.1 | 37.2 | 36.1 |
| 18:31:37 | 39.6 | 37.2 | 35.9 |
| 18:36:37 | 40.2 | 37.2 | 35.7 |
| 7 Hours | 41 | 37.4 | 35.8 |
| 18:46:37 | 42.1 | 37.6 | 36 |
| 18:51:37 | 43.5 | 37.6 | 35.8 |
| 18:56:37 | 44.6 | 37.5 | 36.2 |
| 19:01:37 | 45.8 | 37.6 | 36.3 |
| 19:06:37 | 47 | 37.7 | 36.6 |
| 19:11:37 | 48.1 | 37.7 | 36.8 |
| 19:16:37 | 49 | 37.8 | 37 |
| 19:21:37 | 49.8 | 38.8 | 37.1 |
| 19:26:37 | 50.7 | 39.1 | 37.5 |
| 19:31:37 | 51.4 | 39.3 | 37.9 |
| 19:36:37 | 52.1 | 39.7 | 38.3 |
| 8 Hours | 52.9 | 40 | 38.6 |
| 19:46:37 | 53.5 | 40.4 | 39.2 |
| 19:51:37 | 54.2 | 41.1 | 39.9 |
| 19:56:37 | 54.8 | 41.8 | 40.6 |
| 20:01:37 | 55.4 | 42.4 | 41.7 |
| 20:06:37 | 56 | 43.1 | 42.5 |
| 20:11:37 | 56.4 | 44 | 43.9 |
| 20:16:37 | 56.9 | 45 | 44.9 |
| 20:21:37 | 57.5 | 46 | 46.1 |
| 20:26:37 | 57.8 | 46.8 | 47.3 |
| 20:31:37 | 58.4 | 47.9 | 48.4 |
| 20:36:37 | 58.8 | 48.9 | 49.4 |
| 9 Hours | 59.2 | 49.8 | 50 |
| 20:46:37 | 59.5 | 50.5 | 51.2 |

TABLE IV

| | | | | |
|---|---|---|---|---|
| Start | 7 | 12.1 | 14.5 | 68.6 |
| 18:22:41 | 5.9 | 9.7 | 9.6 | 68 |
| 18:27:41 | 7.3 | 10.3 | 9.7 | 67.7 |
| 18:32:41 | 8.8 | 11.4 | 10.3 | 67.1 |
| 18:37:41 | 10 | 12.3 | 11.1 | 67.1 |
| 18:42:41 | 11.2 | 13.3 | 11.7 | 66.9 |
| 18:47:41 | 12.5 | 14.1 | 12.4 | 66.6 |
| 18:52:41 | 13.6 | 14.9 | 13 | 66.5 |
| 18:57:41 | 14.5 | 15.6 | 13.6 | 66.5 |
| 19:02:41 | 15.5 | 16.5 | 14.1 | 66.2 |
| 19:07:41 | 16.2 | 17.1 | 14.8 | 66.2 |
| 19:12:41 | 16.8 | 17.4 | 15.2 | 65.9 |
| 1 Hour | 17.3 | 18 | 15.8 | 66 |
| 19:22:41 | 18.1 | 18.5 | 16.1 | 65.7 |
| 19:27:41 | 18.6 | 19 | 16.7 | 65.8 |
| 19:32:41 | 19.2 | 19.3 | 17.2 | 65.8 |
| 19:37:41 | 19.8 | 19.7 | 17.7 | 65.6 |
| 19:42:41 | 20.4 | 20.1 | 18.1 | 65.6 |
| 19:47:41 | 21 | 20.3 | 18.5 | 65.5 |
| 19:52:41 | 21.7 | 20.9 | 19 | 65.5 |
| 19:57:41 | 22.1 | 21.1 | 19.3 | 65.4 |
| 20:02:41 | 22.6 | 21.3 | 19.8 | 65.3 |
| 20:07:41 | 23 | 21.6 | 20.1 | 65.4 |
| 20:12:41 | 23.6 | 21.9 | 20.6 | 65.4 |
| 2 Hours | 23.7 | 22.2 | 20.7 | 65 |
| 20:22:41 | 24.2 | 22.3 | 21.1 | 65 |
| 20:27:41 | 24.4 | 22.8 | 21.5 | 65.1 |
| 20:32:41 | 25 | 23 | 21.9 | 65.1 |
| 20:37:41 | 25.6 | 23.3 | 22.1 | 64.8 |
| 20:42:41 | 26.4 | 23.7 | 22.5 | 65 |
| 20:47:41 | 27 | 23.9 | 22.8 | 64.8 |
| 20:52:41 | 27.8 | 24.3 | 23.1 | 64.8 |
| 20:57:41 | 29 | 24.8 | 23.4 | 64.8 |
| 21:02:41 | 30 | 25.2 | 23.8 | 64.7 |
| 21:07:41 | 30.8 | 25.5 | 24.2 | 64.7 |
| 21:12:41 | 31.5 | 25.7 | 24.5 | 64.7 |
| 3 Hours | 32.2 | 26.3 | 24.9 | 64.7 |
| 21:22:41 | 33 | 27.1 | 25.1 | 64.5 |
| 21:27:41 | 33.6 | 27.9 | 25.7 | 64.7 |
| 21:32:41 | 34.1 | 29 | 26.1 | 64.4 |
| 21:37:41 | 34.5 | 30.1 | 26.6 | 64.6 |
| 21:42:41 | 34.6 | 31 | 27 | 64.6 |
| 21:47:41 | 34.9 | 32 | 27.5 | 64.4 |

TABLE IV-continued

| | | | | |
|---|---|---|---|---|
| 21:52:41 | 35 | 33 | 28 | 64.3 |
| 21:57:41 | 35 | 33.6 | 28.4 | 64.3 |
| 22:02:41 | 35.2 | 34.2 | 29.2 | 64.5 |
| 22:07:41 | 35.2 | 34.4 | 29.7 | 64.2 |
| 22:12:41 | 35.2 | 34.7 | 30.4 | 64.2 |
| 4 Hours | 35.1 | 34.6 | 31.2 | 64.3 |
| 22:22:41 | 35.1 | 34.8 | 31.9 | 64.3 |
| 22:27:41 | 35.1 | 34.9 | 32.6 | 64.3 |
| 22:32:41 | 35.2 | 35 | 33 | 64.3 |
| 22:37:41 | 35.3 | 35.2 | 33.6 | 64.3 |
| 22:42:41 | 35.2 | 35 | 33.9 | 64.2 |
| 22:47:41 | 35.1 | 35 | 34.5 | 64.6 |
| 22:52:41 | 35.2 | 35 | 34.8 | 65.6 |
| 22:57:41 | 35.1 | 34.9 | 34.9 | 64.7 |
| 23:02:41 | 35.2 | 35 | 35.1 | 64.6 |
| 23:07:41 | 35.2 | 35.1 | 35.2 | 64.3 |
| 23:12:41 | 35.2 | 35.1 | 35.2 | 64.3 |
| 5 Hours | 35.3 | 35.2 | 35.5 | 64.1 |
| 23:22:41 | 35.2 | 35.1 | 35.5 | 64.1 |
| 23:27:41 | 35.2 | 35.1 | 35.4 | 63.9 |
| 23:32:41 | 35.2 | 35 | 35.6 | 64 |
| 23:37:41 | 35.4 | 35.1 | 35.4 | 63.8 |
| 23:42:41 | 35.3 | 35.1 | 35.4 | 63.8 |
| 23:47:41 | 35.4 | 35.1 | 35.5 | 63.8 |
| 23:52:41 | 35.4 | 35.1 | 35.5 | 63.7 |
| 23:57:41 | 35.3 | 35.1 | 35.5 | 63.8 |
| 0:02:41 | 35.3 | 35.1 | 35.4 | 63.8 |
| 0:07:41 | 35.5 | 35.2 | 35.5 | 65 |
| 0:12:41 | 35.3 | 35.1 | 35.5 | 64.5 |
| 6 Hours | 35.4 | 35.2 | 35.6 | 64.2 |
| 0:22:41 | 35.4 | 35 | 35.6 | 64.2 |
| 0:27:41 | 35.4 | 35.1 | 35.6 | 63.8 |
| 0:32:41 | 35.4 | 35.2 | 35.5 | 63.7 |
| 0:37:41 | 35.4 | 35.1 | 35.5 | 63.7 |
| 0:42:41 | 35.6 | 35.2 | 35.6 | 63.6 |
| 0:47:41 | 35.6 | 35.1 | 35.6 | 63.6 |
| 0:52:41 | 35.5 | 35 | 35.6 | 63.8 |
| 0:57:41 | 35.6 | 35.2 | 35.7 | 63.7 |
| 1:02:41 | 35.6 | 35.3 | 35.7 | 63.7 |
| 1:07:41 | 35.6 | 35.3 | 35.6 | 64.4 |
| 1:12:41 | 35.7 | 35.3 | 35.7 | 65 |
| 7 Hours | 35.7 | 35.3 | 35.6 | 64.2 |
| 1:22:41 | 35.6 | 35.1 | 35.6 | 64 |
| 1:27:41 | 35.7 | 35.2 | 35.6 | 63.5 |
| 1:32:41 | 35.7 | 35.2 | 35.6 | 63.6 |
| 1:37:41 | 35.6 | 35.1 | 35.8 | 63.8 |
| 1:42:41 | 35.7 | 35.2 | 35.7 | 63.5 |
| 1:47:41 | 35.8 | 35.3 | 35.7 | 63.4 |
| 1:52:41 | 35.7 | 35.3 | 35.7 | 63.4 |
| 1:57:41 | 35.8 | 35.3 | 35.7 | 63.4 |
| 2:02:41 | 35.9 | 35.4 | 35.7 | 63.4 |
| 2:07:41 | 35.8 | 35.2 | 35.6 | 64.5 |
| 2:12:41 | 35.9 | 35.3 | 35.7 | 64.5 |
| 8 Hours | 35.9 | 35.3 | 35.7 | 63.9 |
| 2:22:41 | 35.9 | 35.2 | 35.8 | 63.9 |
| 2:27:41 | 36.1 | 35.4 | 35.8 | 63.5 |
| 2:32:41 | 36.3 | 35.4 | 35.8 | 63.5 |
| 2:37:41 | 36.4 | 35.4 | 35.6 | 63.4 |
| 2:42:41 | 36.6 | 35.5 | 35.7 | 63.2 |
| 2:47:41 | 36.6 | 35.3 | 35.8 | 63.3 |
| 2:52:41 | 36.8 | 35.4 | 35.7 | 63.3 |
| 2:57:41 | 36.9 | 35.3 | 35.7 | 63.2 |
| 3:02:41 | 37.3 | 35.4 | 35.7 | 64.7 |
| 3:07:41 | 37.7 | 35.4 | 35.7 | 64.2 |
| 3:12:41 | 38 | 35.4 | 35.8 | 63.9 |
| 9 Hours | 38.4 | 35.4 | 35.7 | 63.4 |
| 3:22:41 | 38.7 | 35.4 | 35.8 | 63.4 |
| 3:27:41 | 38.8 | 35.4 | 35.8 | 63.2 |
| 3:32:41 | 39.3 | 35.5 | 35.8 | 63.3 |
| 3:37:41 | 39.9 | 35.6 | 35.8 | 63.2 |
| 3:42:41 | 40.1 | 35.5 | 35.7 | 63.1 |
| 3:47:41 | 40.4 | 35.5 | 35.8 | 63.1 |
| 3:52:41 | 40.6 | 35.5 | 35.7 | 63.7 |
| 3:57:41 | 41 | 35.6 | 35.9 | 64.3 |
| 4:02:41 | 41.3 | 35.5 | 35.8 | 63.6 |
| 4:07:41 | 41.8 | 35.5 | 35.8 | 63.3 |
| 4:12:41 | 42.5 | 35.6 | 35.8 | 63.3 |
| 10 Hours | 43 | 35.7 | 35.9 | 63.3 |
| 4:22:41 | 43.6 | 35.8 | 35.9 | 63.1 |
| 4:27:41 | 43.9 | 35.6 | 35.8 | 63 |

TABLE IV-continued

| Time | | | |
|---|---|---|---|
| 4:32:41 | 44.5 | 35.7 | 35.8 | 63 |
| 4:37:41 | 45.1 | 35.9 | 35.8 | 63 |
| 4:42:41 | 45.8 | 36 | 35.9 | 64.2 |
| 4:47:41 | 46.2 | 36 | 35.8 | 64.1 |
| 4:52:41 | 46.9 | 36.2 | 35.9 | 63.6 |
| 4:57:41 | 47.3 | 36.1 | 36 | 63.6 |
| 5:02:41 | 47.7 | 36.1 | 35.9 | 63.1 |
| 5:07:41 | 48.2 | 36.4 | 35.9 | 63.1 |
| 5:12:41 | 48.6 | 36.5 | 36 | 63 |
| 11 Hours | 49.1 | 36.7 | 35.9 | 63 |
| 5:22:41 | 49.3 | 36.7 | 35.9 | 62.9 |
| 5:27:41 | 49.7 | 36.9 | 36 | 63 |
| 5:32:41 | 50.3 | 37.3 | 36 | 64.3 |
| 5:37:41 | 50.5 | 37.6 | 36 | 63.8 |
| 5:42:41 | 50.7 | 37.7 | 36.1 | 63.4 |
| 5:47:41 | 50.9 | 38 | 36.1 | 63.1 |
| 5:52:41 | | 38.4 | 36.2 | 63 |
| 5:57:41 | | 38.6 | 36.1 | 63 |
| 6:02:41 | | 39 | 36.1 | 62.9 |
| 6:07:41 | | 39.4 | 36.3 | 63 |
| 6:12:41 | | 39.9 | 36.3 | 62.9 |
| 12 Hours | | 40.4 | 36.3 | 64.4 |
| 6:22:41 | | 40.8 | 36.3 | 63.6 |
| 6:27:41 | | 41.4 | 36.4 | 63.3 |
| 6:32:41 | | 42.1 | 36.4 | 63.3 |
| 6:37:41 | | 42.7 | 36.4 | 63 |
| 6:42:41 | | 43.3 | 36.6 | 63 |
| 6:47:41 | | 44 | 36.6 | 62.9 |
| 6:52:41 | | 44.4 | 36.7 | 62.9 |
| 6:57:41 | | 45.1 | 36.9 | 62.9 |
| 7:02:41 | | 45.8 | 36.8 | 64.2 |
| 7:07:41 | | 46.1 | 37 | 63.6 |
| 7:12:41 | | 46.7 | 36.9 | 63.2 |
| 13 Hours | | 47.1 | 37.2 | 63.3 |
| 7:22:41 | | 47.4 | 37.2 | 63 |
| 7:27:41 | | 48 | 37.2 | 62.9 |
| 7:32:41 | | 48.3 | 37.3 | 62.7 |
| 7:37:41 | | 48.6 | 37.5 | 62.9 |
| 7:42:41 | | 49 | 37.8 | 62.9 |
| 7:47:41 | | 49.4 | 37.6 | 64.3 |
| 7:52:41 | | 49.8 | 37.9 | 63.6 |
| 7:47:41 | | 50.1 | 38 | 63.3 |
| 7:52:41 | | | 38.2 | 63 |
| 7:57:41 | | | 38.3 | 62.9 |
| 8:02:41 | | | 38.6 | 62.9 |
| 8:07:41 | | | 38.9 | 62.9 |
| 8:12:41 | | | 39 | 62.6 |
| 14 Hours | | | 39.4 | 62.8 |
| 8:22:41 | | | 39.7 | 64.2 |
| 8:27:41 | | | 39.7 | 63.2 |
| 8:32:41 | | | 40.1 | 63.2 |
| 8:37:41 | | | 40.4 | 62.9 |
| 8:42:41 | | | 41 | 62.9 |
| 8:47:41 | | | 41.4 | 62.9 |
| 8:52:41 | | | 41.8 | 62.7 |
| 8:57:41 | | | 42.4 | 62.9 |
| 9:02:41 | | | 42.9 | 63.8 |
| 9:07:41 | | | 43.4 | 63.6 |
| 9:12:41 | | | 43.9 | 63.2 |
| 15 Hours | | | 44.4 | 63 |
| 9:22:41 | | | 44.8 | 62.9 |
| 9:27:41 | | | 45.3 | 62.9 |
| 9:32:41 | | | 45.8 | 63.4 |
| 9:37:41 | | | 46 | 65.7 |
| 9:42:41 | | | 46.4 | 66.7 |
| 9:47:41 | | | 47 | 67.1 |
| 9:52:41 | | | 47.4 | 67.3 |
| 9:57:41 | | | 47.7 | 67.5 |
| 10:02:41 | | | 48.3 | 68.1 |
| 10:07:41 | | | 48.5 | 67.8 |
| 10:12:41 | | | 49 | 68 |
| 16 Hours | | | 49.5 | 68.4 |
| 10:22:41 | | | 49.9 | 68.2 |
| 10:27:41 | | | 50.2 | 68.3 |
| 10:32:41 | | | 50.6 | 68.8 |

When one of the Cryo units is, after being removed from a conventional residential freezer, placed against the epithelium of an individual at an ambient temperature of about 76 degrees F., the unit reaches a temperature of about thirty-four degrees more quickly, typically in about one hour.

Figure 19:
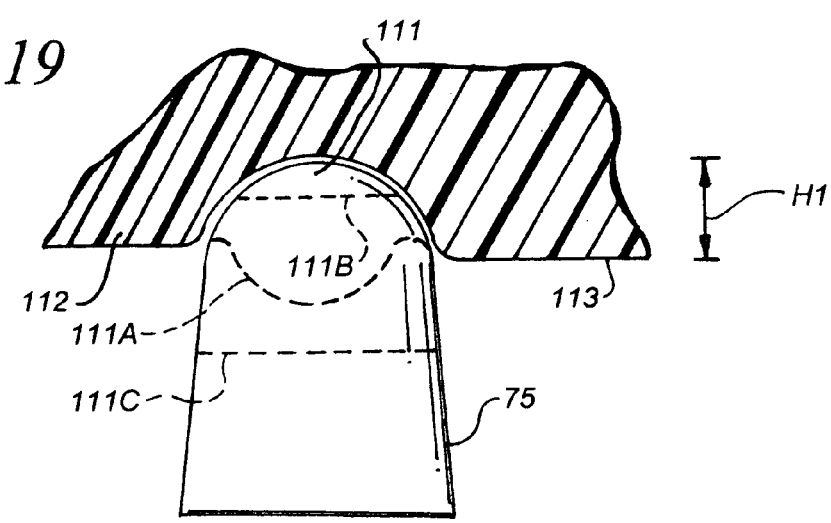
FIG. 19 is a side elevation partial section view illustrating the interaction of the epithelium and a module.

The ability of the Cryo units of the invention to maintain a temperature in the range of thirty-three to forty degrees F. for an extended period of time of two hours or more, typically of three hours or more, has been found useful in treating or preventing various injuries, in part because maintaining the cooling temperature in a range greater than thirty-two degrees F. avoids frostbite. The effectiveness of Cryo units in treating or preventing injuries is also believed to be due in part to the rounded, semi-spherical bottoms 111 (FIG. 19) of modules 75, 75B, 77A, 77C utilized in the Cryo units. As illustrated in FIG. 19, the epidermis 112 of a patient tends to conform to each bottom 111, even though each bottom 111 is covered by a portion of the pliable polymer pan 78A. When the epidermis 112 contours to spherically shaped bottom 111, the surface area of epidermis 112 contacted by bottom 111 is greater than would be the case if bottom 111 were flat and circular. In addition, spherically shaped bottom 111 dispenses cold a greater distance or depth beneath the surface 113 of tissue 112. Finally, the effectiveness of Cryo units in treating or preventing injuries is also believed to be due in part to the "point contact" provided by the spaced apart modules 75, 75B, 77A, 77C in the Cryo units which produces contraction of blood vessels at different points or area along a blood vessel. Portions of a blood vessel near a "point contact" are more likely to contract that portion of a blood vessel spaced away from a "point contact". In FIG. 19, dashed lines 111A and 111B illustrate shapes that the tip or bottom of a module 75 can have instead of the semi-spherical shape 111. Each of the shapes represented by dashed lines 111A and 111B dispenses, in comparison to a flat circular bottom 111C, cold a greater depth beneath the surface 113 of tissue 112 and also increases the surface area of epidermis 112 contacted by bottom 111A and 111B. However, even in the event that each module 75 has a flat bottom 111C, the spacing between modules facilitates "penetration" of epithelial tissue by the Cryo units of the invention because tissue tends, to a certain extent, to move intermediate the bottoms or tips of adjacent modules and toward the bases of the modules.

Each module 75, 75B, 77A, 77C currently has an equivalent shape and dimension, although that need not be the case. The base of each module (the portion of each module adjacent sealing layer 71A in FIG. 10D) 75, 75B, etc. has a diameter or width and has a height in the range of eighteen to thirty-two millimeters, preferably in the range of twenty to thirty mm, and most preferably in the range of twenty-two to twenty-eight mm. Dimensional parity is preferred for each module; consequently, it is also preferred that the diameter (or width) and height of each module be generally equivalent to within 40%, preferably to within 30%, and most preferably to within 20% of each other. The spacing between modules is in the range of six to fifteen mm, preferably within eight to twelve mm.

EXAMPLE III

Figure 22:
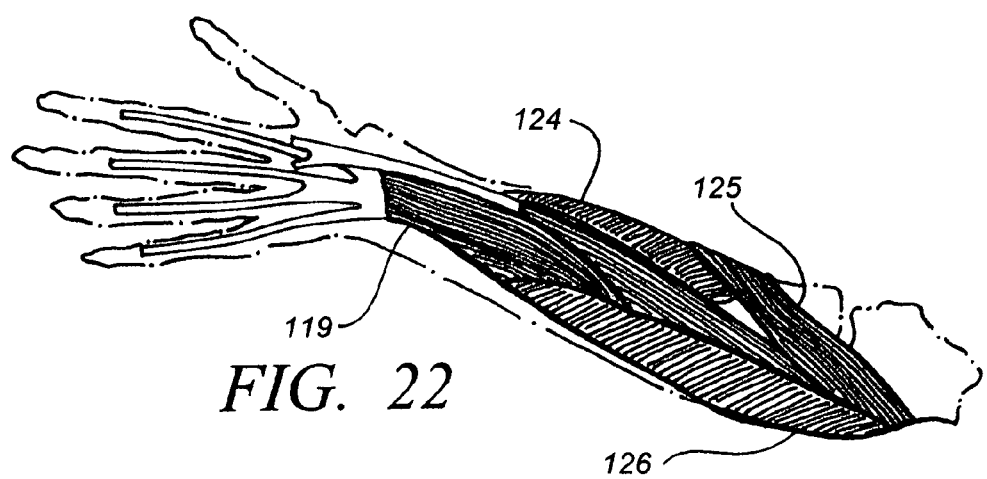
FIG. 22 is a side view illustrating muscles in the forearm.

As is illustrated in FIG. 22, the flexor muscles of the forearm include the flexor digitorum superficialis 119, the flexor carpis radialis 124, the flexor carpi ulnaris 126, and the pronator teres 125.

Figure 21:
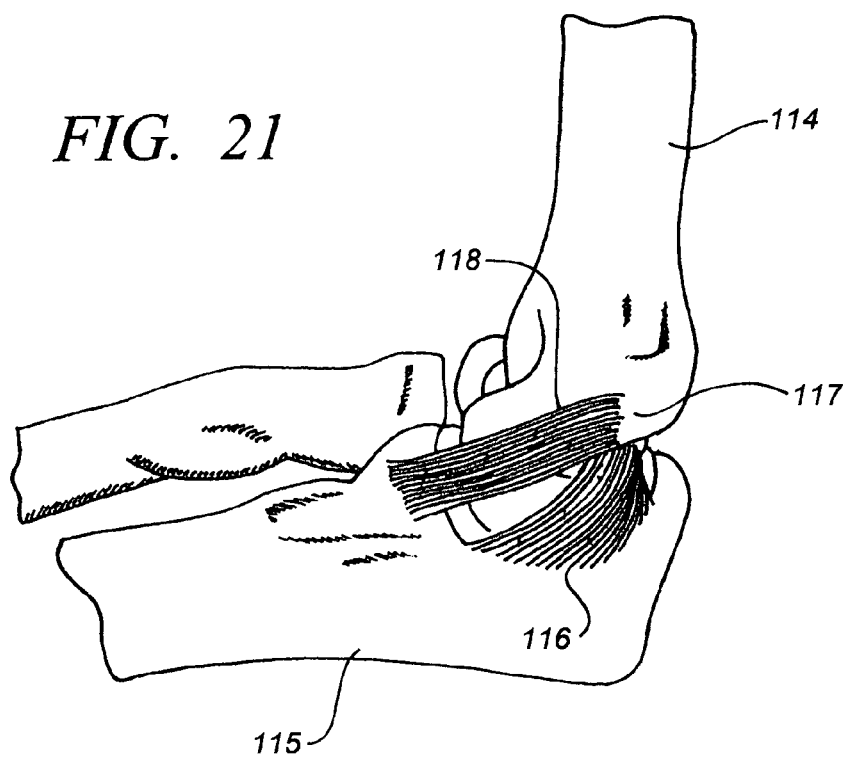
FIG. 21 is a side view illustrating bones and ligaments in the elbow.

The medial collateral ligaments of the elbow are shown in FIG. 21 and include the anterior bundle 118 of the medial collateral ligament and the posterior bundle 116 of the medial collateral ligament. The ligaments interconnect the humerus 114 and the ulna 115. The medial epicondyle is an outgrowth of bone on the bottom and inside of the humerus 114. The tendons connected to the forearm flexors have a common insertion point on the medial epicondyle. When the forearm flexors are forcefully contracted, tension is developed at the insertion point on the medial epicondyle on the tendons attached to these flexors. When the flexors are not properly warmed up, when the arm is not used in a mechanically sound manner, or when the flexors are overused, microtears can be produced in the tendons and cause pain at the medial eipcondyle. Such pain is termed medial epicondylitis. Medial epicondylitis is frequent among athletes in sports that require overhead movement of the arm. These sports include baseball, tennis, badminton, golf, and javelin throwing. The frequency of medial epicondylitis in baseball and tennis has led to the common use of the terms "pitcher's elbow", and "tennis elbow". Not only can microtears occur in the muscles, ligaments and tendons supporting the inside of the elbow, but more serious forms of medial epicondylitis can occur, including repetitive strain injury, an increase in the severity of the elbow pain, and elbow swelling. A prolonged incidence of such serious medial epicondylitis can render the elbow useless for sports or other activities.

A standard ice therapy treatment for reducing inflammation in the elbow consists of applying ice for twenty minutes on and one hour off immediately after pitching or other athletic activities.

EXAMPLE IV

A 41 year old Caucasian male tennis player in good health had medial epicondylitis or "tennis elbow". Any movement of his forearm to pivot his elbow joint produced pain. The condition had existed for eight weeks. Other treatments to remove the pain had not been successful. The Cryo Small unit was removed from the freezer and allowed to warm until the temperature of the unit was greater than thirty-two degrees. The Cryo Small unit was applied to the inside of the patient's elbow continuously for three hours with the semi-spherical module tips or "bottoms" adjacent the patient's skin. During the three hour period, the temperature of the modules in the Cryo unit was in the range of 33 degrees F. to 40 degrees F. The procedure was repeated once a day for the next two days. On the fourth day, after treating the elbow for the previous three days, the patient did not experience pain when he pivoted his elbow joint. During the year following this treatment, the elbow pain did not return.

EXAMPLE V

Skin that has a second-degree burn is blistered and extremely red. The loss of fluid may cause the skin to look wet. A second degree burn typically causes a person's pulse rate to rise due to the severe pain produced by the burn. A large second degree burn can cause a person to go into shock, because the loss of bodily fluids produces a low blood pressure such that insufficient amounts of blood reach the major organs. Shock symptoms include a rapid pulse, nausea, vomiting, rapid breathing, a blue tinge to the lips and finger nails, general weakness, fainting, and cold, moist, pale skin.

Skin that has a third-degree burn may appear white or black and leathery. A third-degree burn destroys nerve ending in the skin. Consequently, the burned area may not be painful. The area around the burn may, however, experience severe pain. Some areas of the burn may be bright red, or may blister. Muscle, fat and bone can be damaged by a third-degree burn. A second degree burn typically causes a person's pulse rate to rise due to the severe pain produced by the burn. A third-degree burn can cause a person to go into shock, because the loss of bodily fluids produce a low blood pressure such that insufficient amounts of blood reach the major organs. Shock symptoms include a rapid pulse, nausea, vomiting, rapid breathing, a blue tinge to the lips and finger nails, general weakness, fainting, and cold, moist, pale skin. Emergency medical treatment is required for all third degree burns.

During initial treatment of second or third degree burns, conventional wisdom sometimes recommends that ice or ice water not be utilized because they will further damage injured tissue.

During initial treatment of a second degree burn, if the burn has blisters that are not open, it is recommended that clothing be removed from the injured area and that cool running water be run over the injured area for around ten minutes to stop the burning process. A cloth moistened with cool water can also be utilized. Blister are not broken open. If the blisters are open, clothing stuck to the burn is not removed and water is not run over the burn because such would increase the risk of shock.

During initial treatment of a third degree burn, clothing stuck to the burn is not removed. The burned area is very briefly immersed in cold water or patted with a cloth moistened with cold water to halt the burning process. Blisters are not broken open. If the blisters are open, clothing stuck to the burn is not removed and water is not run over the burn because such would increase the risk of shock.

EXAMPLE VI

A 40 year old Caucasian male in good health had a red hot coal from a camp fire burn through his clothing and contact the skin on his hip. An area about one and a half inches by one inch on his hip experienced $2^{nd}$ and $3^{rd}$ degree burns. There was some clothing remaining in the burn area. The Cryo Small unit was removed from a freezer and immediately applied to the burn area for thirty minutes with the semi-spherical module tips 111 adjacent the burn area. The temperature of the Cryo unit during the thirty minutes was in the range of 18 degrees F. to 22 degrees F. Then a Cryo Medium unit was applied to the burn area for two hours with the semi-spherical module tips adjacent the burn area. When the Cryo Medium unit was applied, the temperature of the Cryo Medium unit was in the range of 33 degrees F. to 40 degrees F. After the Cryo Medium unit was removed, brown blotches subsequently formed in the skin at the areas corresponding to where the skin was immediately adjacent module tips 111 in the Cryo Small unit. The blotches eventually peeled like skin peels after a sunburn, likely because the modules produced mild frostbite to the upper layers of skin. The burned area turned yellow two to three days after the Cryo Medium unit was removed. On the first day following application of the Cryo units, the burned area was raw, did not bleed, and was weeping. The burned area was covered with large gauze bandages to protect the area and allow air to access the area. Two to three days after the Cryo units were applied, the burned area turned yellow. The area remained yellow for about a month. The burned area began healing from the outside in about a week following application of the Cryo units. The weeping area gradually became smaller, healed over, and a scar formed in about a month. During the next month following formation of the scar, the scar became smaller and fainter until the scar was about one-half the size of the original burn area.

EXAMPLE VII

A 36 year old Caucasian female in good health had a red, very sore sunburn on the back of her neck. Blisters had not formed. A Cryo Small unit was removed from a freezer, allowed to warm until the temperature of the unit was greater than thirty-two degrees, and was placed against the back of her neck for three hours with the semi-spherical rounded module tips 111 adjacent her skin. The polymer pan layer 78B (FIG. 10D) or 232 (FIG. 17) was intermediate tips 111 and her skin. During the three hours that the Cryo unit was applied, the temperature of the unit was initially in the range of twelve degrees F. to twenty-two degrees F. The Cryo unit may also be effective in the temperature range of forty-one degrees F. to fifty degrees F., but thirty-three to forty degrees F. is preferred. The next day the sunburn was gone. Blistering and scarring did not result from the sunburn.

EXAMPLE VIII

Figure 23:
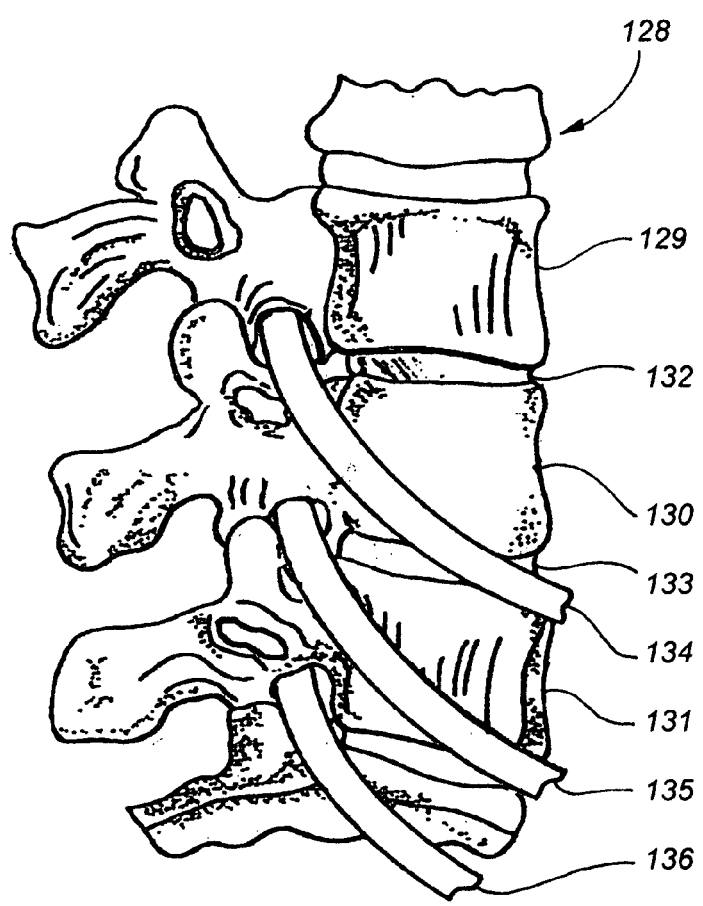
FIG. 23 is a side view illustrating a portion of a spinal column.

As illustrated in FIG. 23, the spine 128 includes spaced apart vertebrae 129, 120, 131. Intervertebral discs 132 and 133 are each located intermediate an adjacent pair of vertebrae. Principal nerves 134, 135, 136 extend outwardly from the spine. FIG. 23 illustrates the configuration of a portion of a normal healthy spine. Over time, the spinal structure deteriorates due to age, poor posture, poor diet, smoking, drinking, lack of exercise, overuse, exercising using the improper body mechanics, exercising without a proper warm-up, exercising and not allowing microtears and other injuries to heal properly, and other factors. When the spinal structure deteriorates, discs 132 and 133 can compress and bulge and deform and rupture such that nuclear material oozes out through the disc annulus. In addition, the alignment of the spine can be altered and the spin can bend excessively in one or more directions to crowd and interfere with proper functioning of internal organs. Such deterioration of the spine often generates pressure against nerves and produces excruciating pain and suffering for an individual. Such pain sometimes is cured only by inserting metal rods in an individual's back or by permanently fusing vertebrae together.

EXAMPLE IX

A 36 year old Black American male has a pair of compressed intervertebral discs in his lower back. The discs bulge and press against nerves in the spine, intermittently producing pain. The individual has the back pain for over six months and takes anti-inflammatory and pain relief drugs. The drugs provide temporary relief. Once the drugs are no longer taken, the intermittent back pain returns in full force.

One option for eliminating the pain is to continue to take appropriate pain relieving and inflammation relieving drugs. A second option is to undergo surgery to fuse vertebrae together to prevent the continual compression-release that is generated against the bulging discs by vertebrae as the spine moves in response to movement of the individual.

A Cryo medium unit is removed from the freezer and allowed to warm until the temperature of the unit is greater than thirty-two degrees. The Cryo Small unit is applied to the patient's back adjacent the bulging discs continuously for four hours with the semi-spherical module tips adjacent the patient's skin. During the four hours, the temperature of the Cryo unit was in the range of thirty-three degrees F. to forty degrees F. The procedure is repeated several times a day for the next four days. On the sixth day, after treating the back and spine for the preceding five days, the patient does not experience pain when walking and undertaking normal activities including sleeping, eating, and sitting at work.

EXAMPLE X

Examples IV, VI, VII, and IX are repeated, except that each module in the Cryo unit has a diameter and a height of twenty mm instead of 25.4 mm (one inch). Similar results are obtained.

EXAMPLE XI

Examples IV, VI, VII, and IX are repeated, except that each module has a diameter and a height of thirty mm instead of 25.4 mm (one inch). Similar results are obtained.

EXAMPLE XII

Examples X and XI are repeated, except that the spacing between the modules is six mm instead of about nine mm (three-eighths of an inch). Similar results are obtained.

EXAMPLE XIII

Examples X and XI are repeated, except that the spacing between the modules is twelve mm instead of about nine mm (three-eighths of an inch). Similar results are obtained.

EXAMPLE XIV

Example IV is repeated, except that after the treatment described in Example IV is completed, the individual resumes playing tennis and, each time he finishes playing tennis for sixty days, applies a Cryo unit to the inside of his elbow for at least two hours when the temperature of the Cryo unit is in the range of thirty-three degrees to forty degrees F. The individual does not experience a reoccurence of medial epicondylitis.

EXAMPLE XV

Example IX is repeated, except that after the five day treatment is completed, the individual, for a period of thirty days, applies a Cryo Medium unit to his back adjacent the bulging discs for at least two hours daily. The Cryo unit is applied when the temperature of the Cryo unit is in the range of thirty-three degrees to forty degrees. The patient's back pain does not reoccur.

In the following EXAMPLES XVI to XXIX, unless otherwise noted, the "Cryo therapy" referred to comprises utilizing a Cryo Small unit once a day by applying it for four to five hours to the patient's skin in the specified injury area. The unit during that entire time period has a surface temperature in the range of thirty-three to forty degrees at the points where the Cryo Small Unit contacts the patient's skin.

EXAMPLE XVI

A forty-eight year old woman had chronic tennis elbow. The right arm hand of the woman was immobilized. She could not even lift a half gallon of milk without extreme pain and her sleep was disturbed. Just prior to Cryo therapy she had on an air cast. Within twenty-four hours of Cryo therapy her hand and elbow were completely functional. At times the pain began to come back to her elbow, but repeating Cryo therapy alleviates the pain.

EXAMPLE XVII

A forty-five year old fisherman was out of work for a month because of chronic tennis elbow. He had no health insurance.

Utilizing Cryo therapy returned him to work in five days. He is still working and utilizes Cryo therapy each day.

EXAMPLE XVIII

A forty-one year old executive was incapable of picking up a gallon of milk with his left hand due to tennis elbow. He utilized Cryo therapy for three days to completely cure the condition. There was no relapse or reoccurrence of the injury for the following nine months.

EXAMPLE XIX

A thirty-eight year old salesman from New York had chronic tennis and/or golfer's elbow in each elbow. He wore a Cryo medium unit on each elbow all day while driving his car. His report: "It's the best therapy I have ever used."

EXAMPLE XX

A thirty-two year old male with fair skin was working on his roof with a T-shirt on. The back of his neck was severely burned. Cryo therapy to one portion of the burn resulted in that portion showing no signs of blistering. The Cryo therapy area was significantly less red that the areas not treated with Cryo therapy. The areas not treat with Cryo therapy blistered and peeled.

EXAMPLE XXI

A forty-one year old male was sunburned badly on the tops of his feet in between the straps on his sandals. Cryo therapy for five day(s) caused the burn to heal with no blistering or peeling.

EXAMPLE XXII

A forty-three year old man was working on his motorcycle during the summer in shorts. He suffered a second degree burn on his calf when he contacted the exhaust pipe. Cryo therapy was utilized immediately. The burn did not blister. When the area healed there was no apparent scar.

EXAMPLE XXIII

A forty-seven year old man burned his forearm on a gas grill, suffered a second degree burn. Treatment and results were generally the same as in Example XXII.

EXAMPLE XXIV

A forty-eight year old man burned his arm on a stove, and suffered a second degree burn. Treatment and results were generally the same as in Example XXII.

EXAMPLE XXV

A Cryo medium was used as a wrist wrest for a forty-one year old data entry individual who had chronic carpel tunnel syndrome. After using the wrist rest of FIG. 21, the pain was significantly alleviated woman had chronic tennis elbow.

EXAMPLE XXVI

A fifty-eight year old woman had chronic debilitating bone degeneration and extreme pain throughout most of her body. Cryo therapy gave her the most relief that she had experienced. Even the narcotic shots she was given once a month did not work. Only Cryo therapy provided pain relief. tennis elbow.

EXAMPLE XXVII

A seventy-eight year old man suffered from a case of shingles. He developed a rash about twenty inches long and nine inches long in the area around his hip. He utilized Cryo therapy for long periods of time, often all day and most of the night. He experiences a dramatic reduction in pain and itching associated with his disease. The relief provided by Cryo therapy was better than any narcotic pain reliever that had been prescribed.

EXAMPLE XXVIII

Same as Example XXVII except the patient was a fifty-eight year old woman.

EXAMPLE XXIX

A forty-one male had chronic psoriasis over 20% of his body, including sub dermal eczema. If the psoriasis is scratched, it turns into large blisters that eventually break and produce large areas of exposed flesh. Cryo therapy was utilized each night for five days. The itching subsided without producing a "numbing" effect common to topical drug applications. He did not scratch himself in his sleep, blistering did not occur, and the eczema when into remission.

Figure 26:
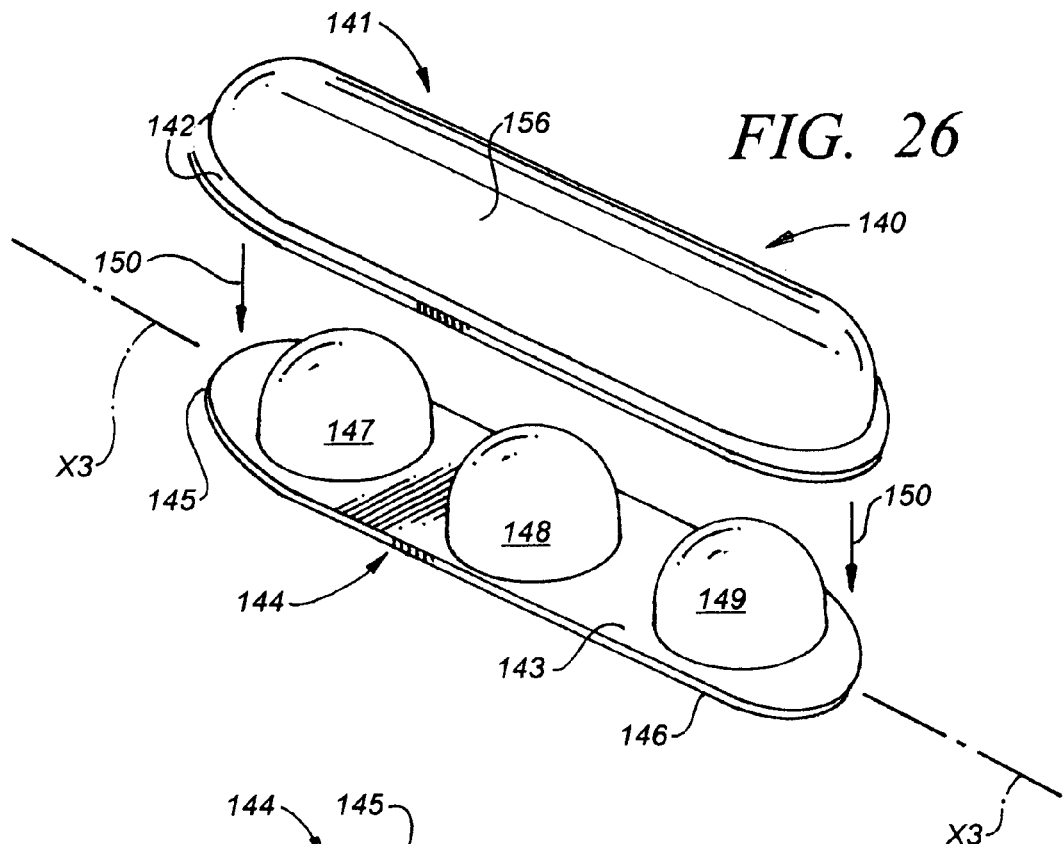
FIG. 26 is an exploded perspective view illustrating a hemorrhoid treatment device of one embodiment of the invention.
Figure 27:
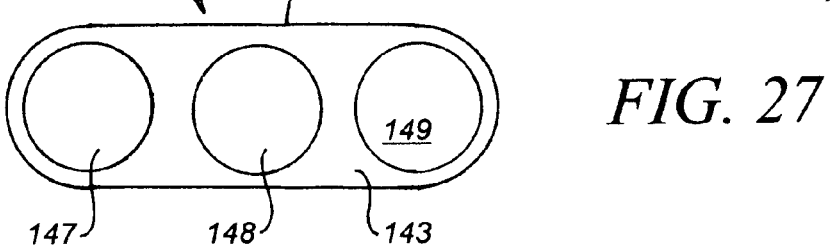
FIG. 27 is a top view illustrating a cooling module utilized in the device of FIG. 26.
Figure 28:
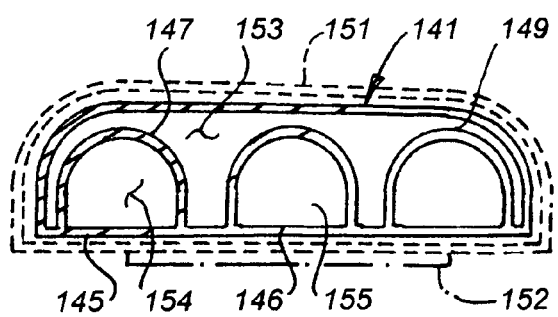
FIG. 28 is a side view illustrating the hemorrhoid treatment device of FIG. 26 illustrating construction details thereof.

FIGS. 26 to 28 illustrate an alternate embodiment of the cold pack of the invention that is utilized to treat hemorrhoids, and is generally identified by reference character 140. While the method of constructing cold pack 140 can vary as desired, the presently preferred procedure is comparable to the process earlier described herein with reference to FIGS. 10A, 10B, 10C, 10D, 11A, 11B, 11C and/or FIGS. 12, 13.

Cold pack 140 includes elongate arcuate polymer cap or pan 141. Pan 141 include circumferential edge 142 that is sealingly glued, welded or other wise attached to the peripheral edge 143 of polymer sheet 145. Polymer sheet 145 is formed in the manner illustrated in FIG. 11B to produce modules 147, 148, 149. Modules 147, 148, 149 are filled with fluid 154, 155 and are then sealed with polymer sheet 146. After modules 147 to 149 are sealed shut, they are placed in fluid 153 in pan 141 in the manner illustrated in FIG. 10D, after which the peripheral edge 143 of polymer sheet 145 is sealed to peripheral edge 142 of pan 141. The fluid 154, 155 in modules 147 to 149 is preferably water and has a freezing temperature lower than that of fluid 153. Fluid 153 presently comprises an aqueous solution of antifreeze and has a freezing temperature that is less than that of fluid 154 and that is preferably less the temperature in a convention house hold refrigerator. However, as would be appreciated by those of skill in the art, the freezing temperatures of fluids 153, 154 can be identical; the freezing temperature of fluid 153 can be higher than that of a fluid 153 in a module; etc. The higher freezing temperature of fluid 154. 155 in modules 147 to 149 and the lower freezing temperature of fluid 153 are deemed important in the presently preferred embodiment of the invention because while fluid 154, 155 completely hardens and freezes in a conventional household freezer, fluid 153 does not. This permits cold pack 140 to be at least somewhat flexible when it is removed from a freezer because fluid 153 is malleable or pliable and is not rigid and hard.

When cold pack 140 is removed from a freezer with fluid 154 frozen and hard, and after the cold pack is then placed against the user's body, the cold pack warms to a temperature in the range of thirty-four degrees to forty degrees F. and retains this temperature for an extended period of time of at least one to thirty minutes. In one to one and a half hours, the cold pack typically warms to a cool temperature of approximately fifty-eights degrees F.

One or more modules 147 to 149 can be utilized in cold pack 140, but it is presently preferred to utilize three modules 147 to 149 each having a diameter of about three-fourths of an inch and having dimensional parity.

Unit 140 is preferably, but not necessarily, covered by a layer 151 of soft fabric that extends completely around unit 140, or, that at least covers the exterior arcuate surface 156 (FIG. 26) of pan 140. It is surface 156, or the fabric or other covering that extends over surface 156, that contacts a patient's body at areas adjacent and around the anus, or, that possibly contacts a portion of the lower end of the anal canal.

A pad 152 (FIG. 28) made of VELCRO™ fastening material or including adhesive can be attached to polymer layer 146 or to fabric layer 151. The VELCRO or adhesive is utilized to secure cold pack 140 to the inside of a user's underwear or other clothing to help maintain the cold pack 140 in the desired position on the buttocks of the user.

In the following examples, cold pack 140 includes water as the fluid 154 in each module 147 to 149, and includes an aqueous solution of antifreeze as fluid 153. When cold pack 140 is removed from a conventional household freezer after the water has frozen, fluid 153 is substantially frozen, but is not rigid such that cold pack 140 is somewhat pliable. After cold pack 140 has been removed from a conventional household freezer for five minutes, fluid 153 has significantly soften and is pliable.

EXAMPLE XXX

A fifty-nine year old female patient has internal hemorrhoids just inside the opening of the anus, i.e., the veins around the anus are swollen and inflamed. In addition, the male patient is experiencing itching at the lower end of the anal canal. The cold pack 140 utilized by the patient includes an outer thin layer of soft fabric 151 extending completely over and around pan 141 and polymer sheet 146. The patient places cold pack 140 in a freezer until fluid 154, 155 is frozen. After fluid 154, 155 is frozen, the cold pack 140 is removed from the freezer and the adhesive patch 152 is utilized to secure cold pack 140 on the patient's underwear such that cold pack 140 is positioned so that at least a portion of the fabric 151 extending over arcuate outer surface 156 contacts the exterior of the patient's anus and tissue external and around the anus (i.e., the arcuate outer surface of pan 141 is adjacent the patient's anus and is adjacent tissue external and around the anus). After cold pack 140 is maintained in position against the patient's anus and against tissue around the anus for one minute, the patient experiences a reduction in itching, the inflammation of the veins around the anus is reduced. After five minutes the swelling of tissue around the anus is reduced.

EXAMPLE XXXI

Example XXX is repeated, except that cold pack 140 does not include fabric layer 151. Similar results are obtained.

One typical treatment for hemorrhoids is the application of PREPARATION H® or other compositions that reduce the swelling and inflammation of veins. The cold pack 140 of the invention does not require the application of such medicants. Further, the cold pack 140 may, if desired, be refrozen and utilized yet again.

In another embodiment of the invention, pan 141 and fluid 153 are not included in cold pack 140, and the cold pack only includes one or more fluids housed in modules 147, 148, 149, and only includes modules 147 to 149 and polymer sheets 145, 146. As noted, cold pack 140 may be partially or completed covered by a fabric or any other desired material.

The shape and dimension of the modules can vary as desired. In one embodiment, each module has a 26 mm diameter and a height of 26 mm. In another embodiment of the invention, each module has a 26 mm height, a length of 40 mm, the distance from front to back (i.e., the depth) is about 24 mm.

FIGS. 29 to 33 illustrate another embodiment of the invention comprising a cooling device utilized by an individual typing on a keyboard.

Figure 24:
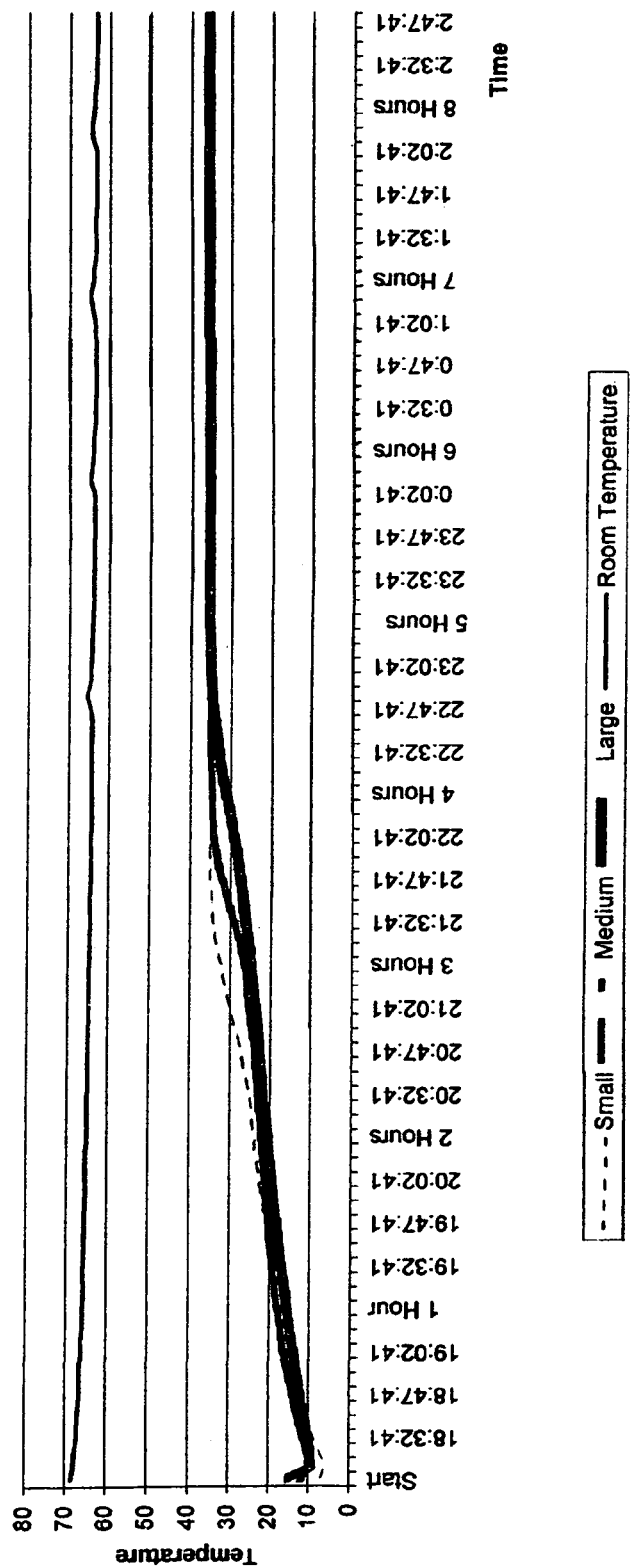
FIG. 24 is a graph illustrating the temperature of Cryo Small, Cryo Medium, and Cryo Large units as they warm in a pouch of thin soft fleece cloth at ambient temperature.
Figure 25:
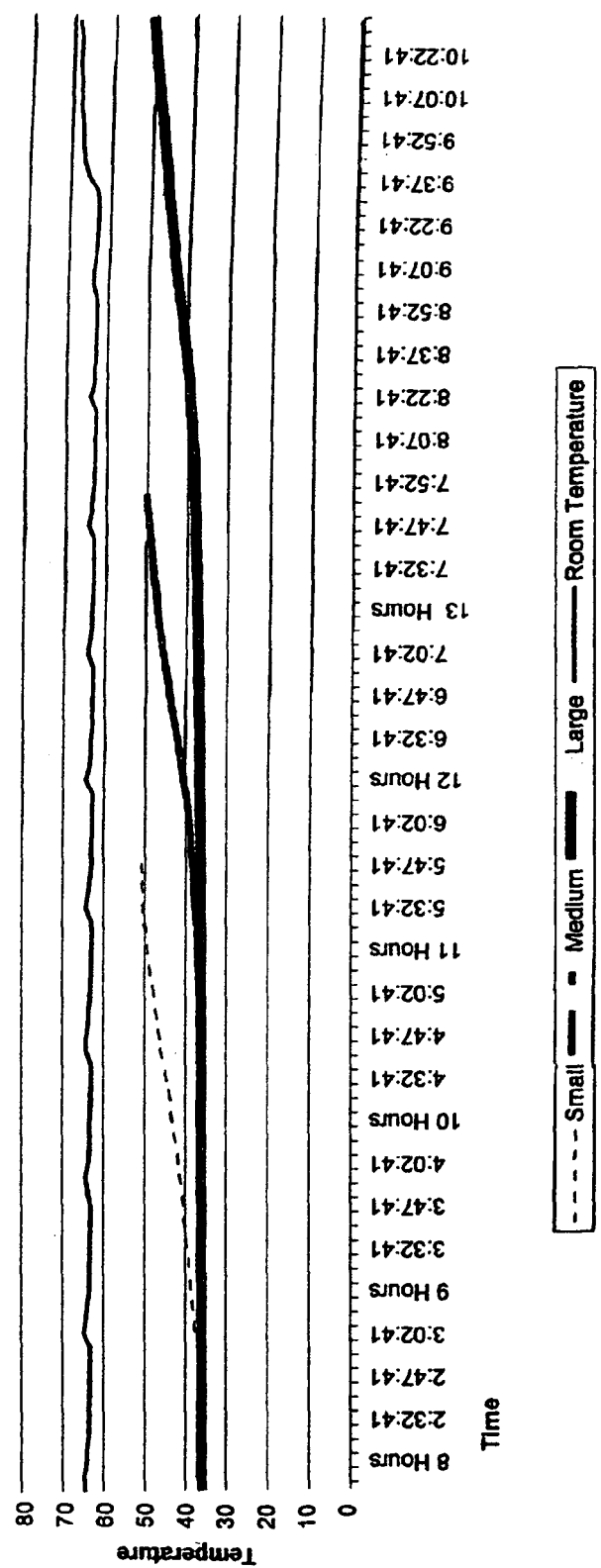
FIG. 25 is a continuation of the graph of FIG. 24 illustrating the temperature of Cryo Small, Cryo Medium, and Cryo Large units as they warm at ambient temperature.

FIGS. 29 and 30 illustrate a cold pack 160 (or heat pack) of the type described earlier herein. Cold pack 160 includes base 167, a plurality (sixteen in FIG. 29) of sealed modules 162, 163 extending upwardly from base 167, and cover 161 sealingly extending over and enclosing (along with base 167) modules 162, 163. Each module 162, 163 includes a first fluid 165, for example water (or an antifreeze solution or other solution). A second fluid 164, for example an antifreeze solution (or water or some other solution), is sealed within cover 161 and extends around modules 162 and 163. Cold pack 160 is frozen, or at least cooled to below freezing, in a freezer prior to the cooling device of FIGS. 29 to 33 being utilized and preferably, though not necessarily, has an extended warming curve of the general type illustrated in FIGS. 24 and 25.

Figure 31:
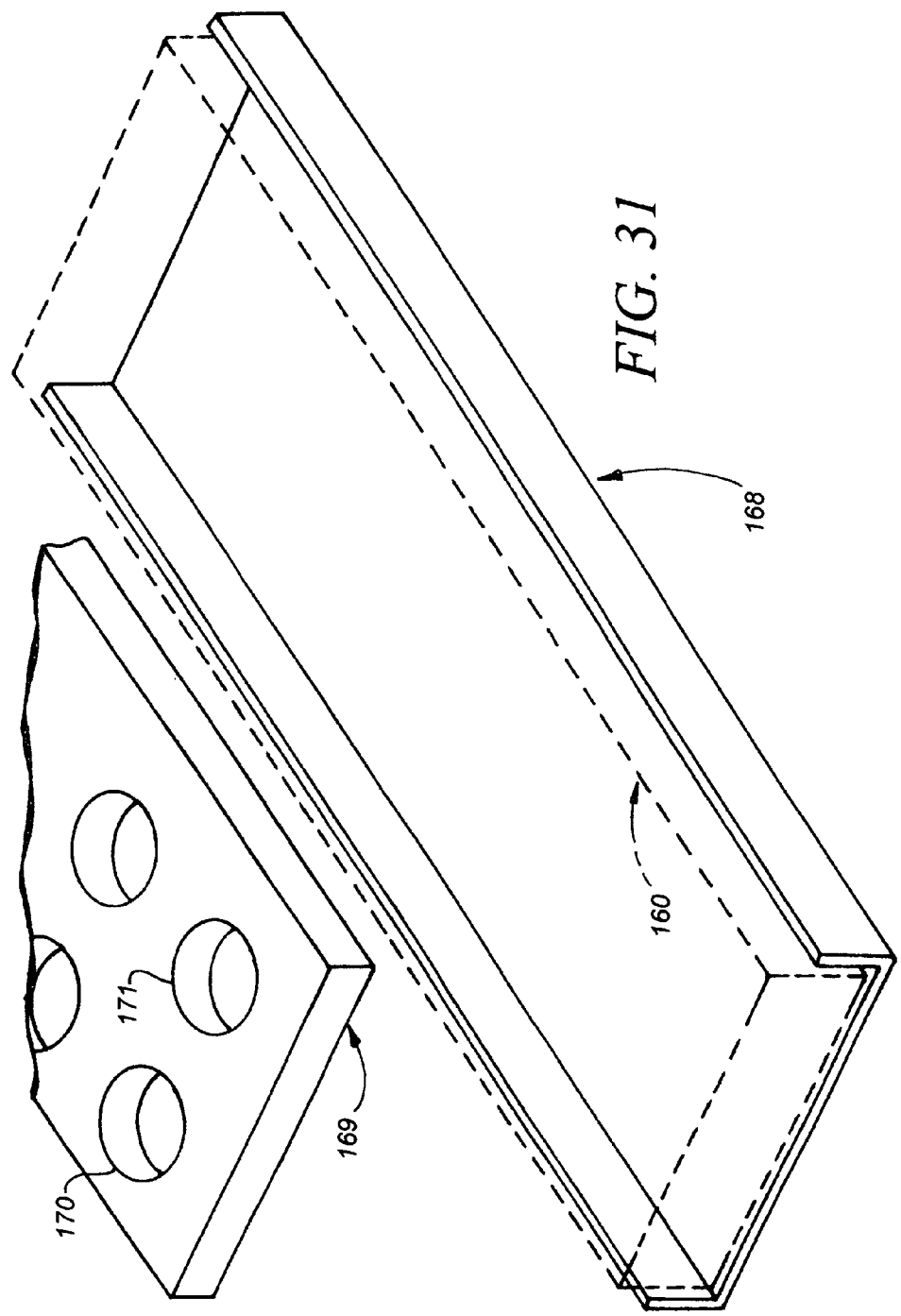
FIG. 31 is a perspective view illustrating the tray and perforated foam member utilized in apparatus for cooling an individual's wrists while the individual is typing on a computer key board.
Figure 32:
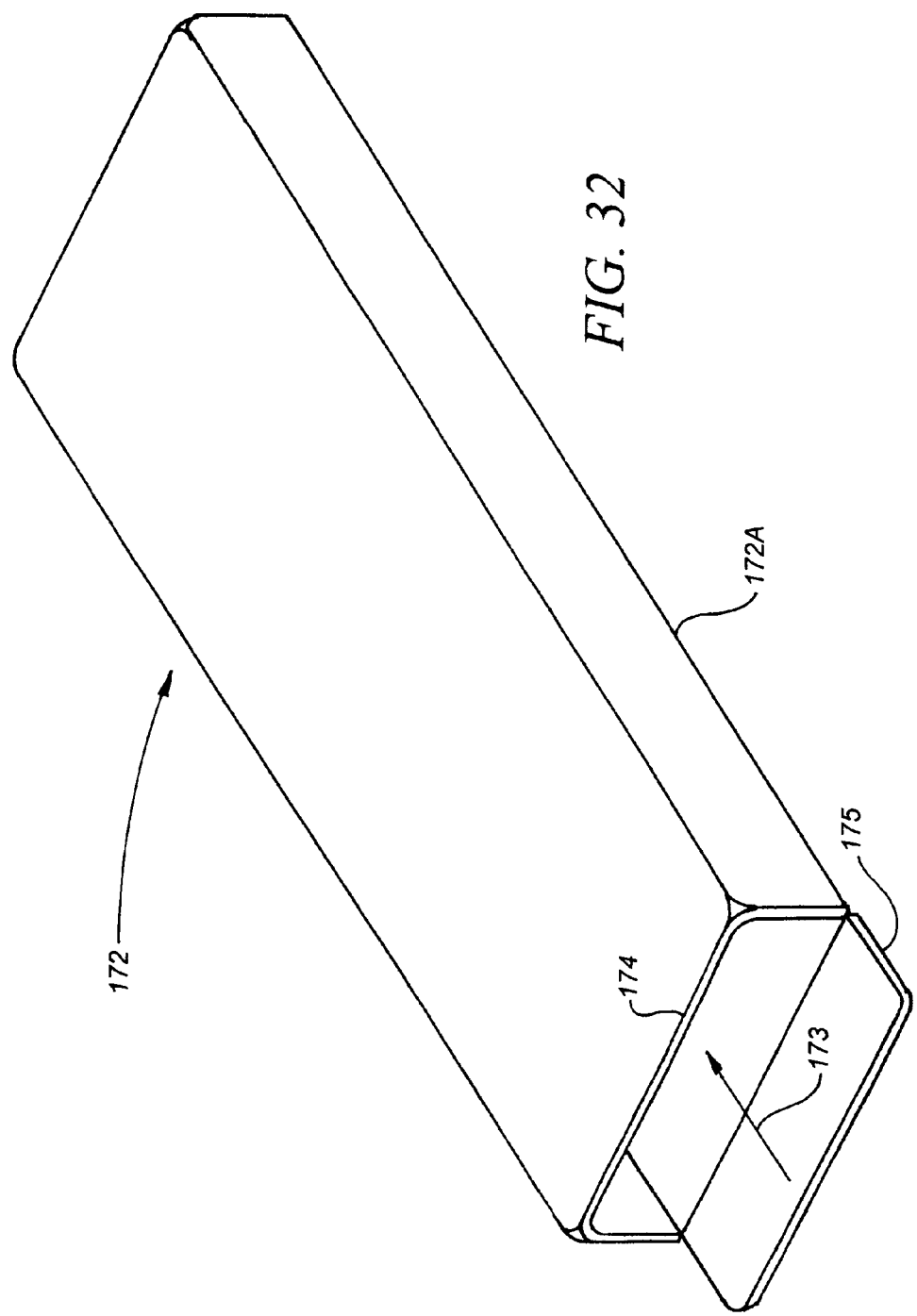
FIG. 32 is a perspective view illustrating a sleeve in which the cooling device and components of FIG. 31 are inserted.
Figure 33:
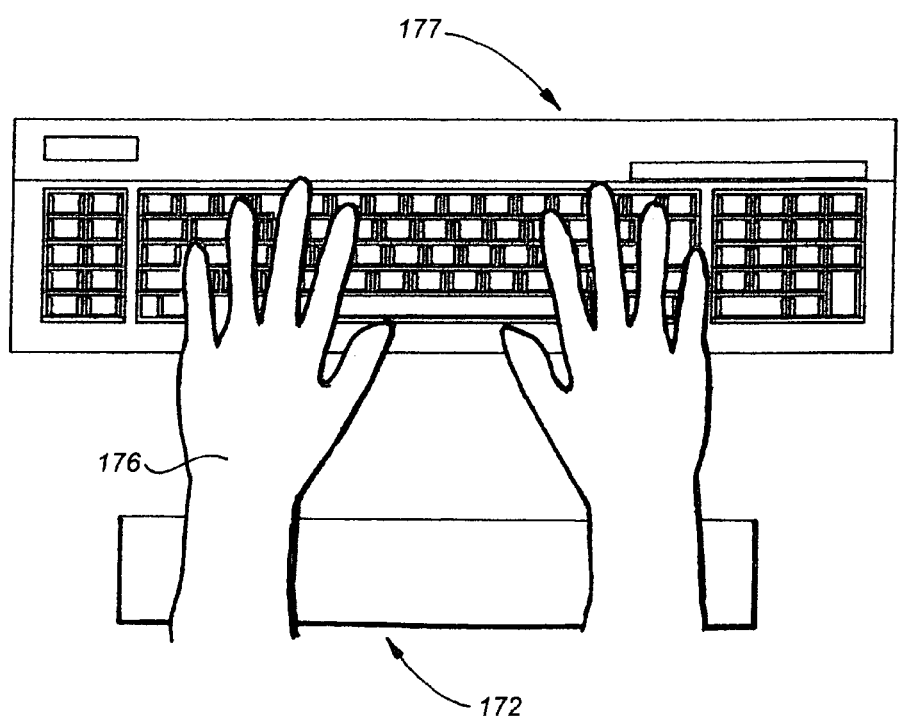
FIG. 33 is a top view illustrating the mode of operation of the assembled apparatus of FIGS. 29 to 32.

After the frozen cold pack 160 is removed from a freezer, it is placed on a substantially rigid tray 168 (FIG. 31) in the manner illustrated in FIG. 31 and an orthogonal perforated foam piece 169 with apertures 170 and 171 is placed on top of cold pack 160. This foam piece 169—cold pack 160—tray 168 "sandwich" is slide into opening 174 of soft, pliable, cloth sleeve 172 and flap 175 is used to close opening 174 to secure the "sandwich" inside sleeve 172. Sleeve 172 can include rubber bottom 172A. Sleeve 172 is then, as shown in FIG. 33, positioned under and contacting the wrists 176 of an individual utilizing a keyboard 177.

Figure 34:
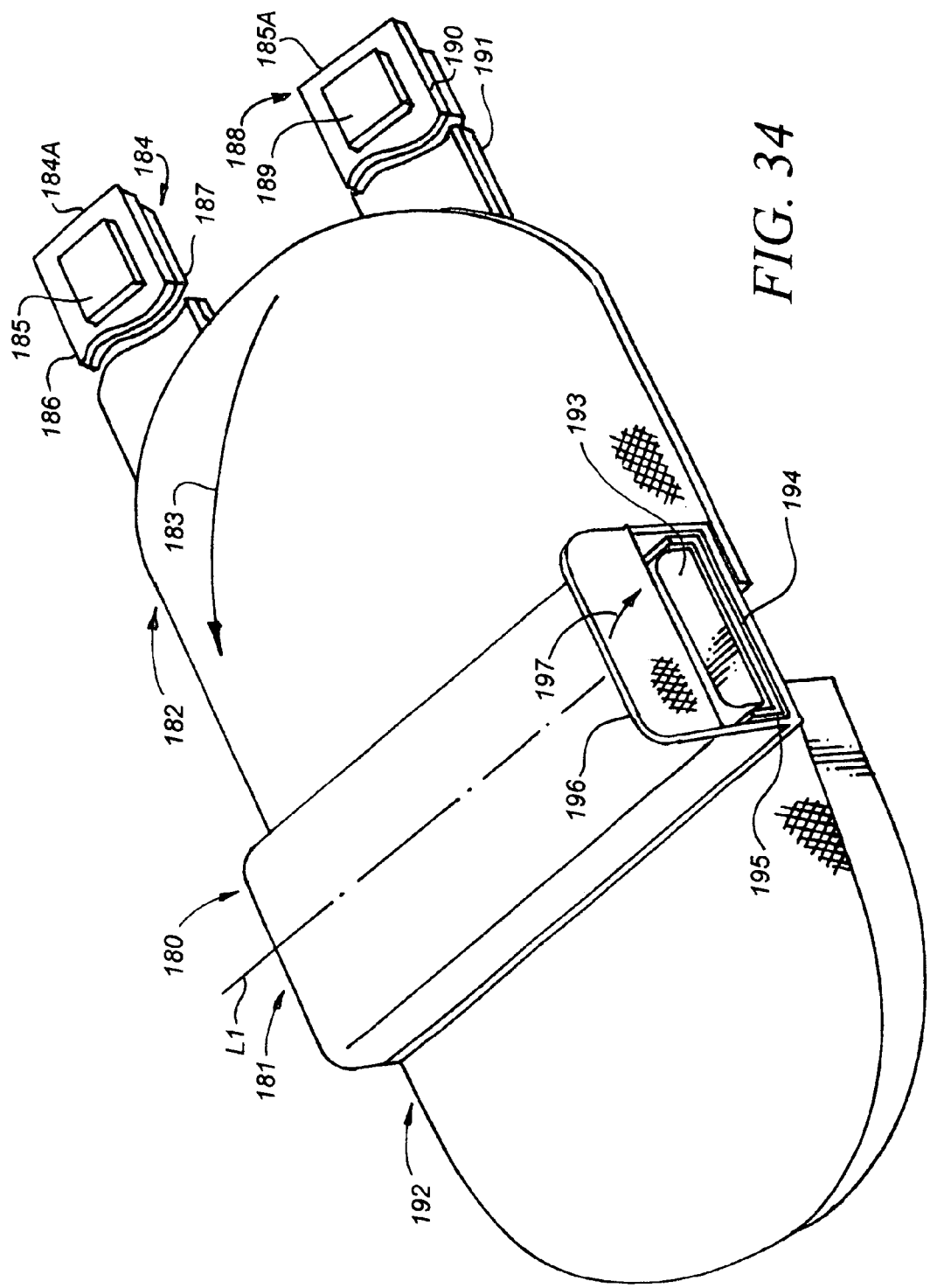
FIG. 34 is a perspective view illustrating a combination splint-cooling device.
Figure 35:
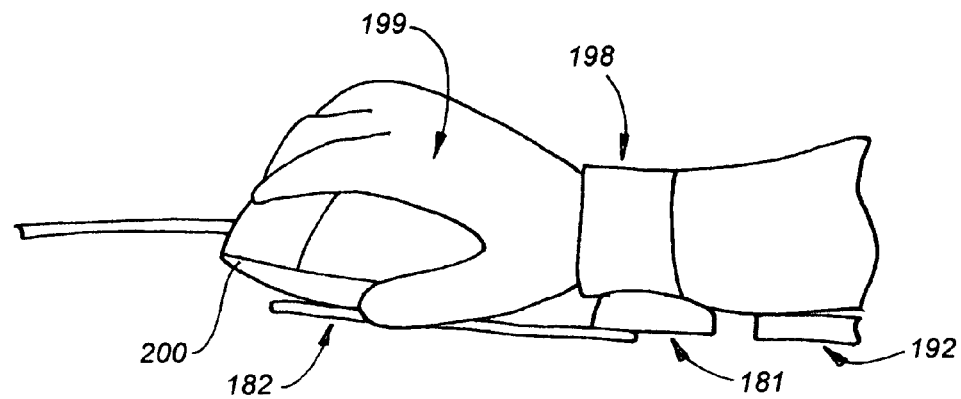
FIG. 35 is a side elevation view illustrating one use of the device of FIG. 34.
Figure 36:
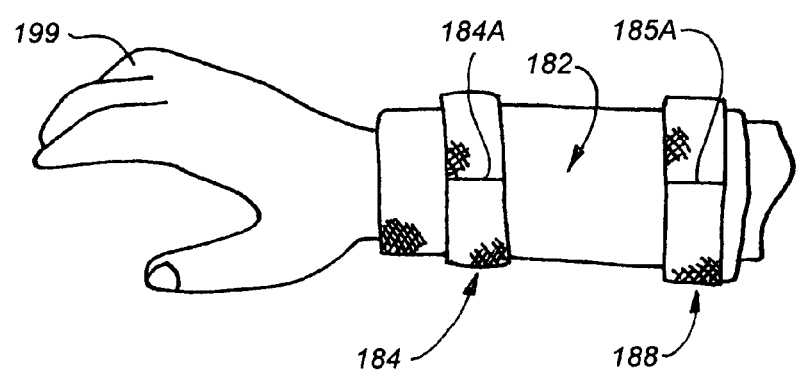
FIG. 36 is a side elevation view illustrating another use of the device of FIG. 34.
Figure 37:
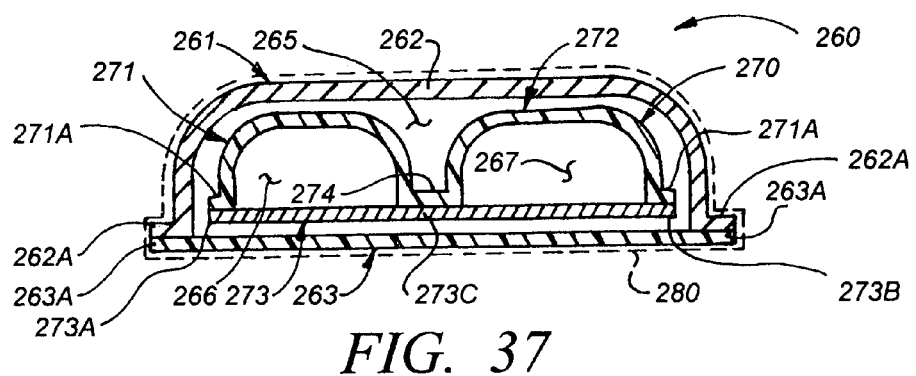
FIG. 37 is a side section view illustrating an alternate embodiment of the invention in which the modules contained therein are provided in an elongate alternate configuration in which the tops of the modules are rounded along their length in a manner generally similar to that in which the tops of an egg or a blimp are rounded.

Another embodiment of the invention is illustrated in FIGS. 34 to 36 and includes a soft, pliable, cloth sleeve 181 comparable to sleeve 172. A cold pack 193 comparable to cold pack 160 is slidably inserted in sleeve 181 on a substantially rigid tray 184 comparable to tray 168. A perforated foam piece (not shown) comparable to foam piece 169 can also be slid into sleeve 181 on top of cold pack 160. Pliable mouse pad 182 is removably attached to sleeve 181. Soft foam arm rest 192 is also removably attached to sleeve 181. Flap 196 is, after cold pack 813 and tray 194 are inserted through opening 195 into sleeve 181, utilized to close opening 195. The proximate end of each strap 184, 188 is attached to pad 182 (or to sleeve 181). VELCRO™ 187, 191 is attached to and extends along substantially the entire length of one side of each of straps 184, 188, respectively. A VELCO™ pad 185, 189 is also attached to the other side of each of straps 184, 188, respectively, on the distal end 186, 190 of each of straps 184, 188. Distal end 186 includes leading edge 184A. Distal end 190 includes leading edge 185A. As shown in FIG. 35, sleeve 181 (with cold pack 193 and tray 194 therein) can be positioned under the wrist 198 of an individual using his hand 199 to move a mouse 200 on a mouse pad 182. In FIG. 35 foam arm rest 192 is detached from sleeve 181 and used to support the forearm of the user. In FIG. 35, the longitudinal axis L1 of sleeve 181 is perpendicular to the forearm of the user. Alternatively, in FIG. 36, after foam arm rest 192 is detached from sleeve 181, sleeve 181 (with cold pack 193 and tray 194 therein) is placed against the wrist and/or forearm (or leg) of the user in a position with longitudinal axis L1 parallel to the forearm, pliable mouse pad 182 is wrapped around sleeve 181, and straps 184 and 188 are wrapped around pad 182 in the manner shown to secure pad 181 and sleeve 181 in position on the user's arm. In FIG. 36 VELCRO™ pad 185 of strap 184 engages a portion of VELCRO™ 187, and VELCRO™ pad 189 of strap 188 engage a portion of VELCRO™ 191. An alternate embodiment of the invention is illustrated in FIG. 37. Cold pack 260 includes elongate arcuate polymer cap or pan 261. Pan 261 includes circumferential edge 262A that is sealingly glued, welded or otherwise attached to the peripheral edge 263A of polymer sheet 263. Sheet 263 is, like sheet 145, substantially flat, although sheet 263 is also preferably pliable so that it will bend.

Module unit 270 is positioned in the interior space circumscribed and sealingly enclosed by a pan unit comprising pan 261 and sheet 263. Unit 270 preferably, but not necessarily, is not attached to pan 261 and sheet 263 and is free to move about in fluid 265. Such detachment of module unit 270 from the pan unit improves the flexibility of cold pack 260 when frozen or at least when partially thawed.

In order to produce module unit 270, a polymer sheet is formed to produce elongate hollow modules 271, 272. Modules 271, 272 are filled with fluid 266, 267 and are then sealed with polymer sheet 273. After modules 271, 272 are sealed shut, they are placed in fluid 265 in pan 261, after which the peripheral edge 262A of polymer pan 261 is sealed to peripheral edge 263A of polymer sheet 263. Fluid 265 can, but preferably does not, completely fill the excess volume in pan 261 that is not occupied by modules 271, 272. Some of the excess volume is instead occupied by air or another gas. Not completely filling the excess volume in pan 261 with fluid 265 gives module unit 260 has more flexibility after it is frozen. Fluid 265 and modules 271, 272 typically together occupy 50% to 95%, preferably 70% to 90%, of the volume within pan 261. The fluid 266, 267 in modules 271 and 272 is preferably water and has a freezing temperature lower than that of fluid 265. Fluid 265 presently comprises an aqueous solution of antifreeze and has a freezing temperature that is less than that of fluid 266, 267 and that is preferably less the temperature in the freezer in a conventional household refrigerator. However, as would be appreciated by those of skill in the art, the freezing temperatures of fluids 266, 267 can be identical; the freezing temperature of fluid 265 can be higher than that of a fluid 266 in a module; etc. The higher freezing temperature of fluid 266. 267 in modules 271, 272 and the lower freezing temperature of fluid 265 are deemed important in the presently preferred embodiment of the invention because while fluid 266, 267 completely hardens and freezes in a conventional household freezer, fluid 265 does not. This permits cold pack 260 to be at least somewhat flexible when it is removed from a freezer because fluid 265 is malleable or pliable and is not rigid and hard.

The sheets utilized to form modules 271 and 272, sheet 273, pan 261, and sheet 263 can comprise any desired material, but presently preferably comprise pliable polymer sheets that can be heat welded to one another. This is important with respect to and facilitates manufacture of the invention.

Figure 38:
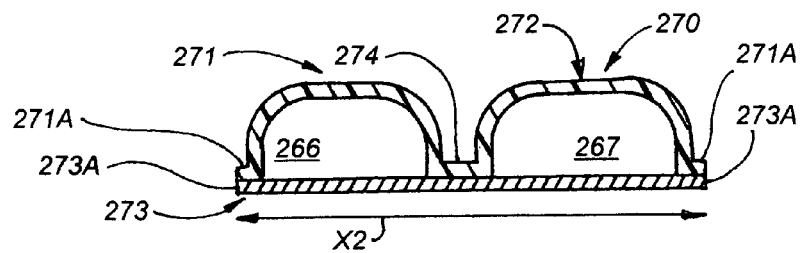
FIG. 38 is a side section view illustrating only the module unit utilized in the embodiment of FIG. 37.

In the alternate embodiment of the invention illustrated in FIG. 38, only unit 270 is utilized. Pan 261, sheet 263, and the fluid 265 are not utilized.

If desired, the circumferential edge formed by fastening together edges 262A and 263A can be folded upwardly and fastened to the outer surface of pan 261. Said circumferential edge preferably extends outwardly only a short distance, preferably one to two mm, from the pan wall that extends upwardly from said edge.

A cloth, gauze, or other soft fabric cover 280 (FIG. 37) can be utilized around the embodiments of the invention illustrated in FIGS. 37 and 38 and can, for example, include a polymer thread fabric that enables edges 262A, 263A to be heat sealed or welded together. During heat welding, the polymer threads melt and bond. When the polymer threads of cover 280 melt, they also, if the threads that melt are adjacent to edges 262A and 263A, bond to edges 262A and 263A. The fabric can comprise fibers or threads of a natural and/or synthetic material. The fabric is preferably soft and moisture absorbent.

As is indicated by FIGS. 37, 38, 26 to 28, the shape and dimension of modules 271, 272, 147 to 149 can vary as desired. The spaced-apart modules 147 to 149 are semispherical and have a circular cross-sectional shape. The spaced-apart elongate modules 271, 272 have an oval cross-sectional area. Modules 271 and 272 are similar to modules 147 to 149 in that they have rounded distal tips. The upper portion of each module 271 and 272 has a shape similar to the upper half of a cylindrically shaped object or to the Goodyear Blimp, i.e., of an elongate cylindrically shaped or egg-shaped object. Accordingly, when the rounded tip of the upper portion of a module 271 is pressed against the portion of the pan that is contacting an individual's skin, the distal tip of module 271 tends to produce a "line of cold" that extends along the length of the rounded tip in a direction generally parallel to sheet 263, parallel to the plane of the sheet of paper on which the drawing of FIG. 38 is imprinted, and parallel to the longitudinal axis X2 (FIG. 38) of a module unit 270 or to the longitudinal axis X3 (FIG. 26) of a cold pack 140. When a flat plane or flat sheet of paper tangentially intersects a cylinder simultaneously along a series of points that are on the outer surface of the cylinder, these points lie along a common line. In a similar fashion, if a flat sheet of paper contacts a series of points simultaneously on the distal tip of a module 271, such points generally lie along a common line, which line is, as noted, generally parallel to flat sheet 263 and longitudinal axis X2. A module unit 270 is, in the same manner as cold pack 140, preferably longer than it is wide.

In another embodiment of the invention, a fluid-containing module 371, instead of having the shape of module 271, 272 or 147, has a conical shape. The cross-sectional area of module 371 taken along section lines A-A has a circular shape.

In a further embodiment of the invention, a fluid containing module 471, instead of having the shape of module 271 or 272 or 147 or 371, has a cylindrically shaped base and a semispherically shaped tip the has a diameter less than that of the base. The cross-sectional area of module 471 taken along section lines B-B has a circular shape.

In still another embodiment of the invention, a fluid-containing module 571, instead of having the shape of module 271 or 147 or 371 or 417, has a "tall" cylindrically-shaped configuration in which the height is greater than the diameter of the module 571. The cross-sectional area of module 571 taken along section lines C-C has a circular shape.

Importantly, each module 147, 271, 371, 471, 571 preferably has a rounded distal tip. The base, or proximate portion, of each module is preferably flat. When a module is inserted in the buttocks such that the rounded distal tip is adjacent the rectal opening, the flat base distributes to forces applied to the module when the individual is sitting and reduces the risk that a module unit 270 or cold pack 260 will be pressed into the rectal opening. One object of the invention is to position a cold pack 260 or module unit 270 immediately adjacent the rectal opening, but to not press cold pack 260 or module unit 270 into the rectal opening.

Fabric covers 151 and 280 can be applied in any desired manner. For example, a rectangular piece of fabric can be wrapped around a cold pack 260 and sewn and glued to secure the fabric on the cold pack. The presently preferred manner, however, of applying a fabric cover 151, 280 comprises utilizing a flow wrap machine of the type commonly utilized to wrap candy bars. This wrapping procedure was discovered after the cold pack 260, 140 of the invention was developed and after other wrapping procedures had been investigated. A flow wrap machine has evidently never been utilized to wrap a medical device that is used to treat hemorrhoids. There appears to be at least one very good explanation for this, namely, food manufacturers and the manufacturers of flow wrap machines never contemplated the use of a flow wrap machine for medical purposes because it is undesirable for consumers to associate a machine used to wrap candy bars with diseases or medical ailments, in particular, with hemorrhoids or with unedible products such as Preparation H™ salve.

A flow wrap machine includes a dispensing roll of a strip of soft fabric. The fabric includes a polymer thread or other material that permits the fabric to be heat sealed. During operation of the machine the dispensing roll continuously turns about an axle and a strip of fabric is continuously fed from the dispensing roll. The fabric strip utilized is presently two to three inches wide, although the width of the fabric strip can vary as desired. The machine feeds the end of the strip of fabric and a first assembled cold pack 140, 260 to a first processing station in the machine at which the last five to six inches of the strip of fabric is wrapped around the cold pack. The edges of the strip of fabric are sealed and folded to form an elongate seam extending longitudinally along the exterior of the flat bottom 145, 263 (FIGS. 26, 37) of the cold pack 140, 260 and parallel to the longitudinal axis of cold pack 140, 260.

The machine then continues to feed, or index, the partially wrapped cold pack 140, 260—with the last five to six inches of the strip of fabric still attached to fabric being fed from the dispensing roll—to a second processing station at which the leading folded end of the fabric is heat sealed along spaced apart first and second heat seal lines (for example, lines 309A and 309B in FIG. 45) that are perpendicular to the longitudinal axis of cold pack 140, 260, and that are spaced apart from the cold pack 140, 260. Simultaneously with the heat sealing, the leading end of the fabric strip is cut along a first cut line (for example, the line indicated by dashed line 307 in FIG. 45) intermediate the spaced apart heat seal lines. The first cut line also is perpendicular to the longitudinal axis of the cold pack 140, 260. In addition, the first cut line is spaced apart from the cold pack 140, 260, i.e. the flow wrap machine does not cut through cold pack 140, 260.

The machine then continues to feed, or index, the partially wrapped cold pack 140, 260 (with the leading end heat sealed and cut) until the trailing edge of the cold pack reach the second processing station. At the second processing station, the trailing folded end of the fabric is heat sealed along spaced apart third and fourth head seal line that are perpendicular to the longitudinal axis of cold pack 140, 260. Simultaneously with the heat sealing, the trailing end of the fabric strip is cut along a second cut line intermediate the spaced apart third and fourth heat seal lines. The second cut line also is perpendicular to the longitudinal axis of the cold pack 140, 260, and, is spaced apart from the cold pack 140, 260. As soon as the trailing end of the fabric strip is cut along the second cut line, the cold pack 140, 260 has been completely wrapped in the same fashion as a Baby Ruth™, Three Musketeers™ or other conventional candy bar. And, concurrently with the first cold pack being moved from the first toward the second processing station, a second cold pack is being partially wrapped at the first processing station in the same manner that to first cold pack was wrapped. When the trailing end of the folded strip around the first cold pack is indexed to the second processing station, the leading end of the folded strip around the second cold pack is also indexed to the second processing station. When the machine make a cut along the second cut line between the third and fourth heat seal lines, one of said third and fourth heat seal lines seals the trailing end of the folded fabric strip around the first cold pack, while the other of said third and fourth heat seal lines seals the leading end of the folded fabric strip that extends around the second cold pack, and so on. The foregoing operation of a flow wrap machine in accordance with the invention is appreciated by those of skill in the art, although prior to the invention there appeared to be no problem or motivation in the art that would remotely suggest or accept the idea of using a food wrapping machine in connection with the treatment of hemorrhoids.

Figure 45:
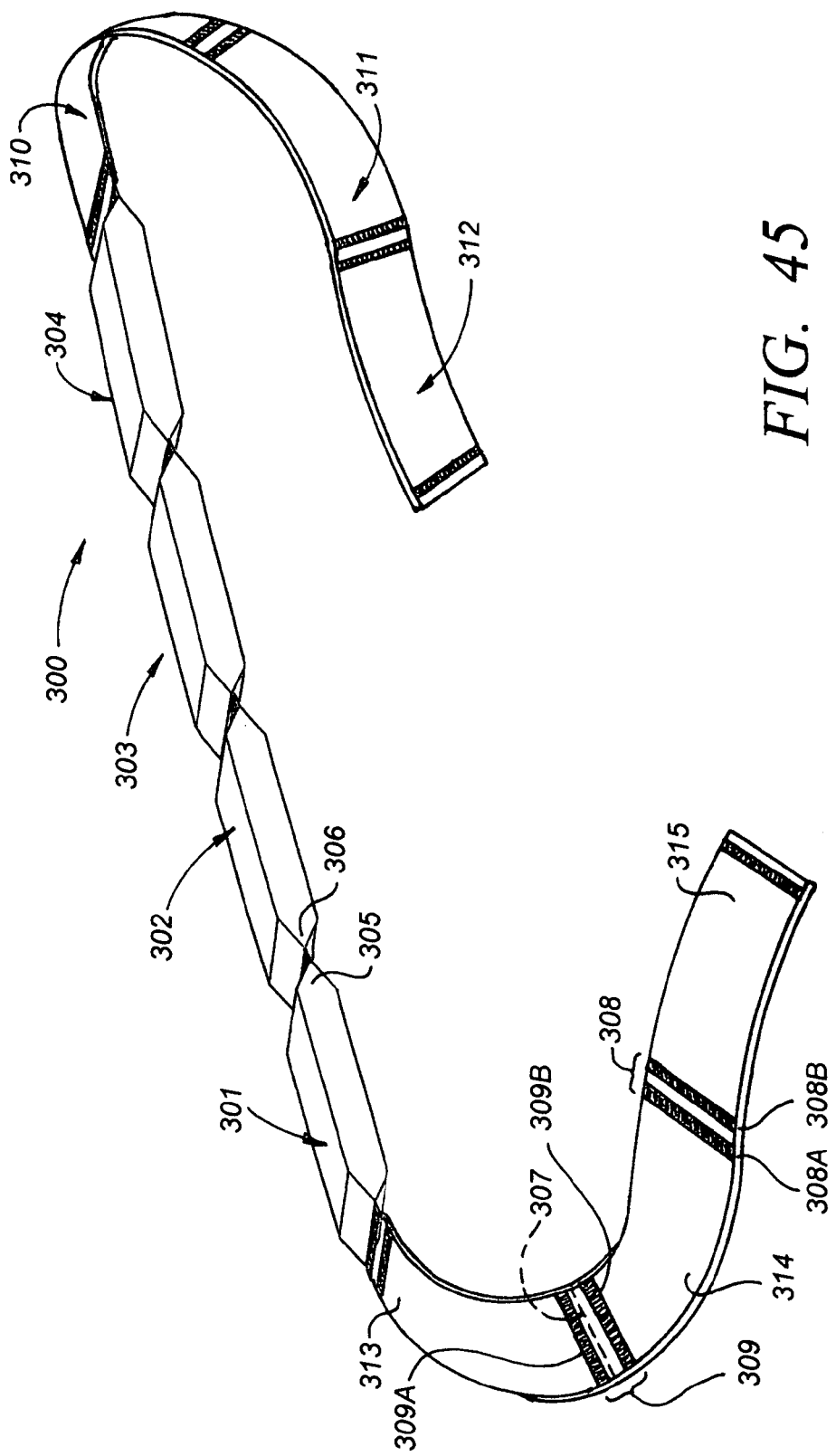

FIG. 45 illustrates another embodiment of the invention comprising a folded/heat sealed fabric strip 300, or headband, which is formed by passing a fabric strip from a dispensing roll through a flow wrapping machine in which the folding and heat sealing mechanisms are activated and operate, and, in which the cutting mechanism is rendered inoperative. Fabric wrappers 301, 302, 303, 304 could each contain, in accordance with the prior art, a candy bar. However, in contrast to the prior art, wrappers 301 to 304 each contain a cold pack 140, 260. Wrappers 310, 311, 312 at one end of the strip 300 do not contain a cold pack, nor do wrappers 313 to 315 at the other end of strip 300. The pair of heat seal lines between wrappers 301 and 302 is not readily visible in FIG. 45, nor is the pair of heat seal lines between wrappers 302 and 303 readily visible, or the pair of heat seal lines between wrappers 303 and 304. Adjacent pair of heat seal lines 309A and 309B are visible, as are heat seal lines 308A and 308B, as well as other heat seal lines not identified with reference characters. In normal operation of a flow wrap machine, the strip 300 would have been cut along line 307 between heat seal lines 309A and 309B, and would have been cut along lines between other adjacent pairs of heat seal lines visible in FIG. 45. The object of the invention illustrated in FIG. 45 is, however, to form a disposable headband. Consequently, cuts are made only at the ends of the headband, and not intermediate each adjacent pair of heat seal lines. VLECRO™ fasteners or other fastening apparatus can be used to secure strip 300 on the head of a user.

Strip 300 is placed in a freezer to freeze cold packs 140, 260 that are in wrapper 301, 304. Strip 300 is then removed from the freezer and placed around a user's forehead or around the neck or another desired portion of the user's body. The wrappers 310 to 312 at one end of strip 300 and the wrappers 313 to 315 at the other end of strip 300 function as ties and are used to the strip 300 in position around the user's head. The fabric utilized to form strip 300 preferably is soft, moisture absorbent, and is—in order to be utilized in the flow wrap machine—susceptible to being heat sealed. As used herein fabric is cloth. Cloth is something made by weaving, felting, knitting, knotting, bonding, or crocheting natural or synthetic fibers and filaments and used in variations of texture, finish, weight, width for clothing, upholstery, rugs, and industrial purposes or treated so that it will serve a special purpose (as made semirigid for bookbinding). Cloth is, in many cases, pliable.

Figure 39:
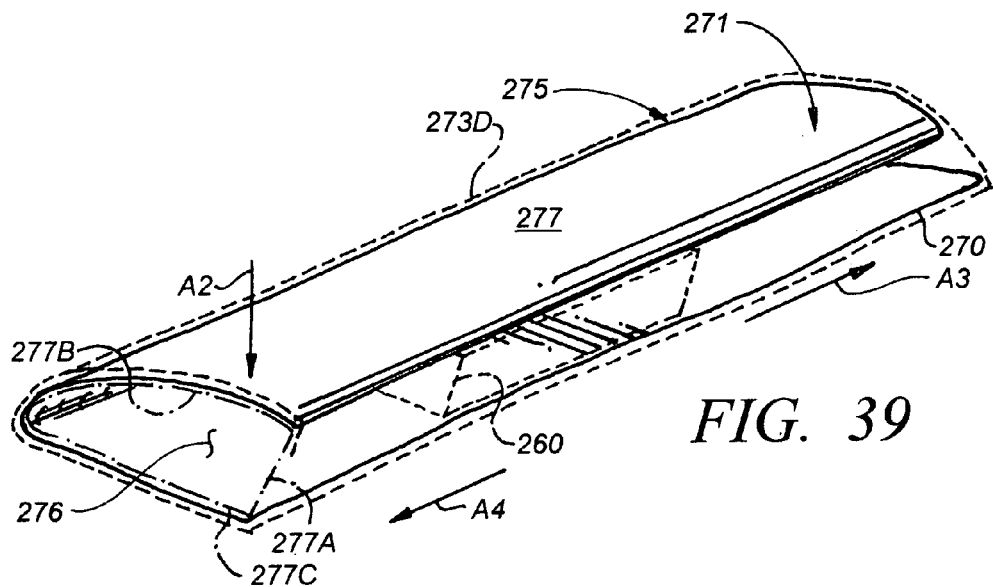
FIG. 39 is a perspective view illustrating an alternate embodiment of the invention utilized to extract heat from the wrist of an individual using a computer keyboard.

FIG. 39 illustrates another invention comprising a substantially rigid hollow member 275 formed from aluminum or another heat conductive material. Member 275 includes arm 271B attached to and upwardly extending from and over base 270A. Arm 271B preferably flexes a short distance downwardly in the direction of arrow A2 when a user rests his wrist on surface 277 of arm 271B and when the user's associated elbow is resting on a table top or other support surface on which member 275 is placed. Ice or a cold pack 272 is inserted into the hollow interior space 276 of member 275. The cold pack cools member 275.

In use of member 275, member 275 is placed on a table or other flat surface with a mouse positioned on the table forwardly of the front of member 275. Alternately, a keyboard 177 can be positioned forwardly of the front of member 275 in the manner illustrated in FIG. 33. In FIG. 39, the front of member 275 comprises the elongate leading edge of member 275 that is nearest the alphanumeric characters "FIG. 39" that are imprinted on the drawing sheet. Additionally, arrow A3 extends along and is parallel to the front of member 275. A computer operator places his wrist (or wrists when the user is operating a keyboard 177) on upper surface 277 and grasps and operates, with the palm of his hand facing down in the manner illustrated in FIG. 35, the keyboard or mouse. Surface 277 draws heat away from and cools the wrist. The use of member 275 reduces the risk that a user will develop carpal tunnel syndrome, or, if a user has carpal tunnel syndrome, mitigates discomfort associated with the syndrome.

Spaced apart rib panels 277A can be inserted in space 276 to provide structural support. The lower edge 277C of a rib panel 277A preferably rests on or is attached to base 270A while the upper edge 277B of a rib panel 277A is preferably spaced apart from arm 271B such that arm 271B can downwardly flex at least a short distance when a user places his wrist on surface 277 in the manner described above. Arm 271B will, after it downwardly flexes, preferably, but not necessarily, contact upper edge 277B.

A cold pack(s) 260 inserted in interior space 276 of member 275 can extend the entire length of member 275. Alternately, the cold pack 260 need not extend the entire length of member 275.

The cold pack 260 inserted in interior space 276 of member 275 in FIG. 39 does not extend along and contact the entire length of arm 271B and/or base 270A of member 275. The aluminum or other heat conductive material used to fabricate member 275 effectively absorbs heat along the entire length of member 275 and makes the entire length of arm 271B cool to the touch even though cold pack 260 does not extend along the entire length of member 275. Further, the cold pack 260 need only contact one of base 270A and arm 271B.

A pair of spaced apart rib panels (not shown) can, if desired, be placed intermediate the ends of member 275 to form, along with opposing portions of arm 271B and of base 270A, a compartment in which cold pack 260, when inserted in member 275 in the manner illustrated in FIG. 39, fits. When the cold pack 260 is inserted in this compartment, said pair of spaced apart rib panels comprise the ends of the compartment and prevent cold pack 260 from sliding along interior space 276 in the directions of arrow A3 and A4 (FIG. 39) toward either end of member 275.

Member 275 can be covered with a removable sleeve 273D or other cover manufactured from paper, fabric, or another desired material. The sleeve 273D presently preferably comprises a fabric, slides onto member 275, and includes an opening that is, after member 275 is inserted in the opening, closed by moving a fabric flap over the opening and securing the flap to a VELCRO™ fastening strip that is attached to the exterior of sleeve 273D. The sleeve 273D preferably insulates arm 271B to an extent by preventing a user's wrist from directly contacting surface 277.

Figure 40:
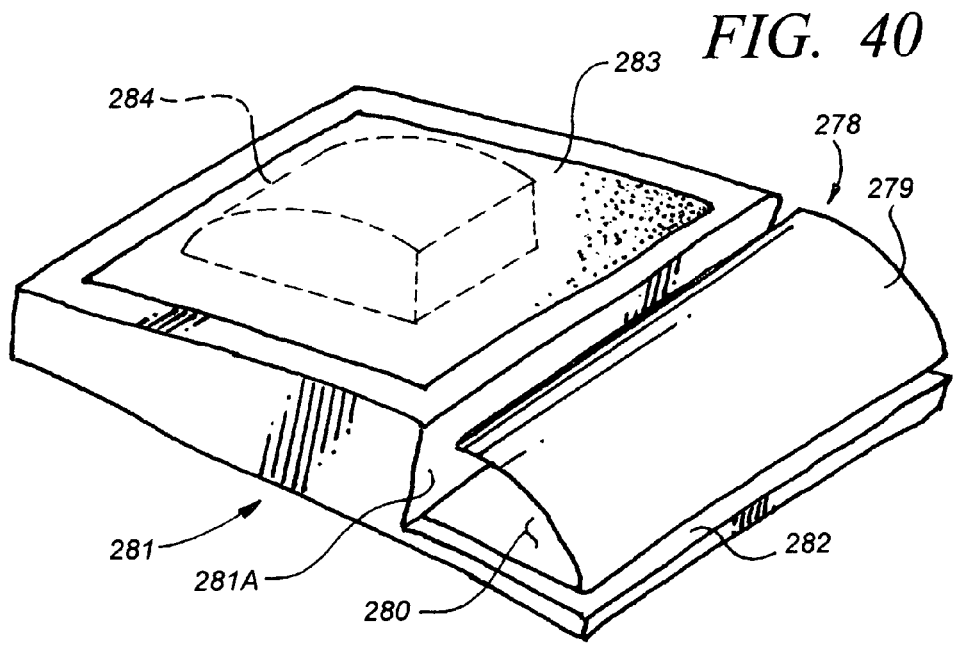
FIG. 40 is a perspective view illustrating an alternate embodiment of the invention utilized to extract heat from the wrist of an individual using a computer mouse.

FIG. 40 illustrates a further invention including a substantially rigid hollow member 278 formed from aluminum or another heat conductive material. Ice or a cold pack (not visible) is inserted into the interior space 280 of member 278. The cold pack cools member 278 in a manner comparable to that described above with respect to member 275. The cold pack can, but need not, extend the entire length of member 278.

In use, member 278 is placed on horizontally oriented support surface 282 of stand 281 such that the front of member 278 is, in the manner illustrated in FIG. 40, adjacent vertically oriented surface 281A of stand 281. A computer operator places his wrist on upper surface 279 while operating, in a manner similar to that illustrated in FIG. 35, a mouse, indicated in ghost outline 284, on mouse pad surface 183 of stand 181. VELCRO™ fastening material or other fasteners can be utilized to secure member 178 in place on step 182.

Member 278 can be covered with a removable sleeve or other cover manufactured from paper, fabric, or another desired material. The sleeve presently preferably comprises a fabric, slides onto member 278, and includes an opening that is, after member 278 is inserted in the opening, closed by moving a fabric flap over the opening and securing the flap to a VELCRO™ fastening strip that is attached to the exterior of sleeve 278. The sleeve 278 preferably insulates arm 278 to an extent by preventing a user's wrist from directly contacting surface 277. The sleeve also functions to maintain in interior space 280 a cold pack that has been inserted therein.

Figure 41:
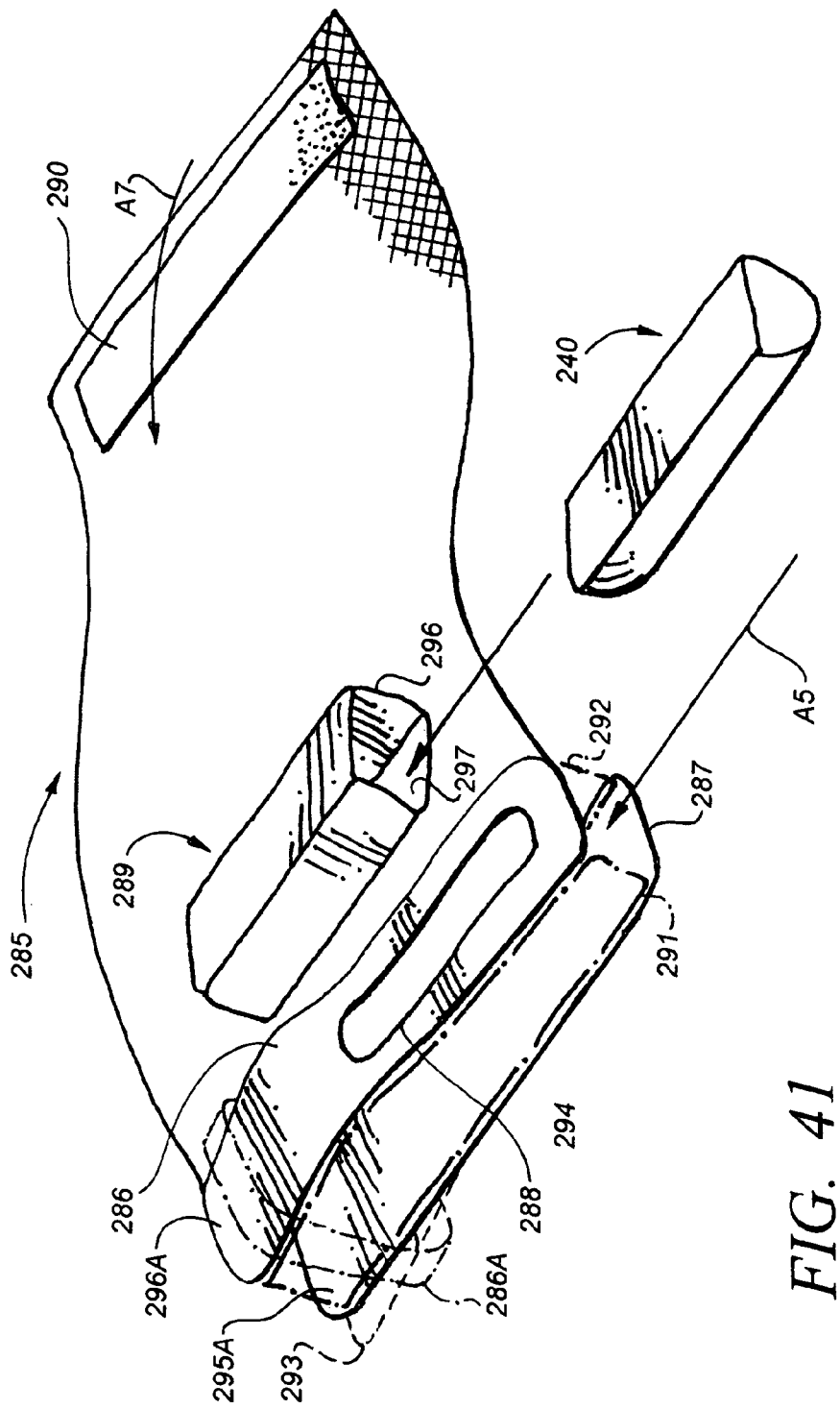
FIG. 41 is a perspective view illustrating an alternate embodiment of the invention utilized to support and extract heat from the wrist of an individual.
Figure 42:
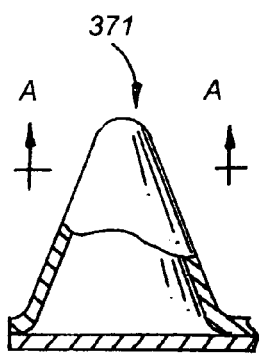
FIG. 42 is a side, partial section view illustrating an alternate module configuration in accordance with the invention.
Figure 43:
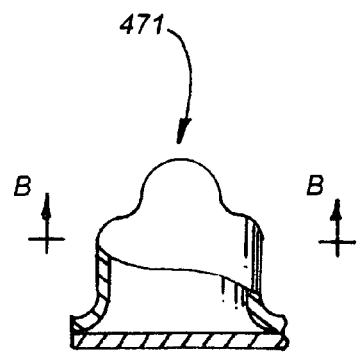
FIG. 43 is a side partial section view illustrating still another alternate module configuration in accordance with the invention.
Figure 44:
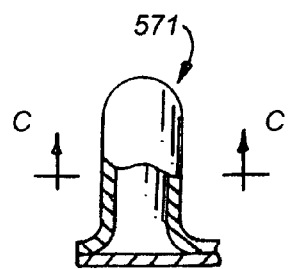
FIG. 44 is a side partial section view illustrating still a further alternate module configuration in accordance with the invention; and, FIG. 45 is a perspective view illustrating yet another embodiment of the invention.

The wrist splint apparatus illustrated in FIG. 41 includes an opposing pair of substantially rigid splints 286, 287 fabricated from a polymer, a metal, or other desired material. Splint 286 has aperture 288 formed therethrough. Aperture 288 can be formed through any desired portion of the wrist splint apparatus.

Splints 286 and 287 are interconnected by a pair of equal-sized pieces of elastic fabric indicated in ghost outline by dashed lines 291, 292 in FIG. 41. Fabric piece 291 extends between and interconnects one side of splints 286 and 287. Fabric piece 292 (which can if desired differ in shape and dimension from piece 291) is spaced apart from piece 291 and interconnects the other side of splints 286 and 287. Orthogonal, hollow fabric sleeve 289 is permanently or detachably secured to the outside of splint 286 and covers opening 288. Sleeve 289 includes mouth or opening 296. Sleeve 289 can, if desired, be provided with a flap (not shown) that can be used to open and close mouth 296. A cold pack 240 slides into sleeve 289 and functions to cool a user's wrist.

In FIG. 41, the splint apparatus is inverted. In use, prior to sliding the apparatus onto a user's hand the apparatus is rotated one hundred and eighty-degrees from the orientation in FIG. 41. After the apparatus is slid onto a user's hand, opening 288 is adjacent the bottom of the user's wrist and tongue 296A extends from the bottom of the user's wrist onto the central area of the user's palm. Accordingly, opening 288 enables the bottom of the user's wrist to contact or be positioned adjacent the bottom 297 of sleeve 289. The bottom 297 of sleeve 289 preferably has an opening or is fabricated from a mesh material or other material that facilitates the passage of heat from a user's wrist to a cold pack 240 positioned inside sleeve 289. In FIG. 41, tongue 296A is angled downwardly with respect to the remainder of splint 286. Tongue 295A can also, as indicated by dashed lines 293, be angled downwardly with respect to the remainder of splint 285. Consequently, when the apparatus of FIG. 41 is worn on a user's hand and associated wrist, tongue 296A angles upwardly into the palm of the hand and tongue 295A angles upwardly away from the back of the user's hand.

Fabric wrap 285 is wrapped in the direction of arrow A around splints 286 and 287 to secure the splints 286, 287 and sleeve 289 on a user's wrist. Cold pack 240 is inserted in sleeve 289. VELCRO™ fastening material 290 is utilized to secure wrap 285 in place after it has been wrapped around splints 286, 287.

In use, cold pack 240 is placed in sleeve 289, and an individual moves his hand in the direction of arrow A5 (FIG. 41) to slide his hand intermediate splints 286, 287 and elastic fabric pieces 291, 292 until opening 288 is positioned over the bottom (i.e., the palm side) of the user's wrist and tongue 296 extends into the central area of the user's palm. Tongue 295 extends into the central area of the top, or back, of the user's hand. Fabric wrap 285 is wrapped about splints 286, 287 and sleeve 289 to secure the splints 286, 287 on the user's wrist. If desired, a strip of material, indicated in FIG. 41 in ghost outline by dashed lines 286, can be wrapped and detachably fixed about tongues 295, 296 to secure more rigidly the splint apparatus in position on the wrist and hand of a user.

While any cold pack 240, 260 can be utilized in the various embodiments of the invention described herein, a cold pack of the general type described herein with reference to FIGS. 18, 19, 20, 24, 25 and other related Figs. is preferred because such a cold pack often maintains a temperature in the range of thirty-four to forty degrees for an unusually long period of time, typically in the range of one to four hours. It is, of course, understood that a cold pack of the type illustrated in FIGS. 26 to 28 and FIGS. 37 and 38 which comprises only a few modules likely will maintain a temperature in the range of thirty-four to forty degrees for a shorter period of time, typically at least thirty minutes and usually about one hour.

Opening 288 can, if desired, be formed in splint 287, in fabric piece 291, and/or in fabric piece 292 to permit a cold pack(s) 240 to apply cold to the top, and/or sides of a user's wrist.

In an alternate embodiment of the invention, the modular cold pack structure of FIG. 18 (or of FIG. 38) is utilized "as is", without utilizing a pan 78, 78A, 78B, 232 or a second liquid 94, 233 that is normally retained in the space intermediate the pan and modules 75 (or 271 and 272 in FIG. 38). In this alternate embodiment of the invention, the fluid, instead of comprising a liquid 94 or 233, comprises the ambient air. When the cold pack structure of FIG. 18 is applied to a location on an individual's skin with the rounded ends of the modules contacting the skin (or contacting a layer of fabric interposed between the rounded ends and the skin), the frozen or cooled liquid contained in the modules cools the air that is between the modules, typically to a temperature that is eight to ten degrees warmer than the temperature of the liquid in the modules. When the air is cooled, its density increases and slows movement of the air intermediate the modules. As a result, this alternate embodiment is useful in treating tennis elbow and other ailments earlier referred to herein.

In still another alternate embodiment of the invention, the modular cold pack structure of FIG. 18 (or of FIG. 38) is utilized with a pan 78, 78A, 78B, 232, but with air or a gas instead of the second liquid 94, 233 that is normally retained in the space intermediate the pan and modules 75 (or 271 and 272 in FIG. 38). In this alternate embodiment of the invention, instead of a liquid 94 or 233, the fluid utilized comprises air or another gas. When this cold pack structure is applied to a location on an individual's skin with the rounded ends of the modules contacting the portion of the pan that either contacts the skin or contacts a layer of fabric interposed between the pan and the skin, the frozen or cooled liquid contained in the modules cools the air that is between the modules and the pan, typically to a temperature that is at least eight to ten degrees warmer than the temperature of the liquid in the modules. As a result, this alternate embodiment is also useful in treating tennis elbow and other ailments earlier referred to herein.

Having described my invention in such terms as to enable those of skill in the art to make and practice it, and having described the presently preferred embodiments thereof, I claim:

1. A method of treating carpal tunnel syndrome in the wrists of an individual, comprising the steps of
    (a) providing a computer keyboard;
    (b) providing a substantially rigid hollow elongate cooling wrist support (275) comprising a heat conductive metal including a hollow inner space;
    (c) providing a cooling apparatus that maintains a temperature in the range of thirty-three degrees F. to forty degrees F. for at least thirty minutes, said cooling apparatus shaped and dimensioned to slide into at least a portion of said hollow inner space and contact at least a portion of said heat conductive metal and comprising
        (i) a pan housing with a cover (161), a substantially flat bottom,
        (ii) a plurality of spaced apart modules each
            inside and detached from said pan housing,
            with a substantially flat base adjacent said substantially flat bottom,
            with a generally circular cross section when taken parallel to said base,
            with a rounded top
                extending outwardly away from said substantially flat base and said substantially flat bottom, and
                contacting said cover,
        (iii) a first fluid in said modules having a first freezing temperature,
        (iv) a second fluid in said pan housing intermediate said housing and said modules, said second fluid having a second freezing temperature different from said first freezing temperature;
    (d) providing a fabric sleeve to cover said wrist support, said sleeve slidably mountable on said wrist support;
    (e) cooling said cooling apparatus to freeze at least one of said first and second fluids;
    (f) placing said cooled cooling apparatus and said foam sheet in said hollow inner space of said wrist support to contact and cool said wrist support, said foam sheet contacting said cover and intermediate said cover and said wrist support;
    (g) sliding said fabric sleeve on said wrist support;
    (h) placing said wrist support generally adjacent said key board such that an individual can place his wrists on said wrist support contacting said fabric sleeve and operate with his hands said keyboard;
    (i) positioning the wrists of the individual on said wrist support contacting said fabric sleeve such that the individual can operate said keyboard with the individual's hands.

2. The method of claim 1 wherein each of said modules have dimensional parity.

3. The method of claim 2 wherein said rounded tops are spaced apart a distance in the range of eight mm to twelve mm, and said modules each have a width and height each in the range of eighteen mm to thirty-two millimeters.

* * * * *